United States Patent
Yamanoi et al.

(10) Patent No.: US 9,233,958 B2
(45) Date of Patent: Jan. 12, 2016

(54) SUBSTITUTED PHENYLAZOLE DERIVATIVES

(71) Applicant: DAIICHI SANKYO COMPANY, LIMITED, Tokyo (JP)

(72) Inventors: Shigeo Yamanoi, Tokyo (JP); Hidenori Namiki, Tokyo (JP); Yuichi Ochiai, Tokyo (JP); Madoka Hoshino, Tokyo (JP); Koji Matsumoto, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 14/372,832

(22) PCT Filed: Jan. 17, 2013

(86) PCT No.: PCT/JP2013/050710
§ 371 (c)(1),
(2) Date: Jul. 17, 2014

(87) PCT Pub. No.: WO2013/108800
PCT Pub. Date: Jul. 25, 2013

(65) Prior Publication Data
US 2014/0357675 A1  Dec. 4, 2014

(30) Foreign Application Priority Data
Jan. 18, 2012 (JP) .................................. 2012-007840

(51) Int. Cl.
| | |
|---|---|
| *C07D 417/12* | (2006.01) |
| *C07D 403/12* | (2006.01) |
| *C07D 401/14* | (2006.01) |
| *C07D 401/12* | (2006.01) |
| *C07D 413/12* | (2006.01) |
| *C07D 249/06* | (2006.01) |
| *C07D 257/04* | (2006.01) |
| *C07D 263/32* | (2006.01) |
| *C07D 271/06* | (2006.01) |
| *C07D 277/20* | (2006.01) |
| *C07D 277/30* | (2006.01) |

(52) U.S. Cl.
CPC ............ *C07D 417/12* (2013.01); *C07D 249/06* (2013.01); *C07D 257/04* (2013.01); *C07D 263/32* (2013.01); *C07D 271/06* (2013.01); *C07D 277/20* (2013.01); *C07D 277/30* (2013.01); *C07D 401/12* (2013.01); *C07D 401/14* (2013.01); *C07D 403/12* (2013.01); *C07D 413/12* (2013.01)

(58) Field of Classification Search
CPC .................................................... C07D 417/12
See application file for complete search history.

(56) References Cited

U.S. PATENT DOCUMENTS

| | | | |
|---|---|---|---|
| 8,232,287 B2 | 7/2012 | Kaneko et al. | |
| 8,557,802 B2 | 10/2013 | Yamanoi et al. | |
| 8,722,711 B2 | 5/2014 | Yamanoi et al. | |
| 8,754,112 B2 | 6/2014 | Yamanoi et al. | |
| 2014/0221437 A1 | 8/2014 | Yamanoi et al. | |

FOREIGN PATENT DOCUMENTS

| | | |
|---|---|---|
| WO | WO 02/46174 A1 | 6/2002 |
| WO | WO 2005/061489 A1 | 7/2005 |
| WO | WO 2005/115383 A2 | 12/2005 |
| WO | WO 2007/003960 A1 | 1/2007 |
| WO | WO 2007/003962 A2 | 1/2007 |
| WO | WO 2007/039178 A2 | 4/2007 |
| WO | WO 2007/116229 A1 | 10/2007 |
| WO | WO 2009/051119 A1 | 4/2009 |
| WO | WO 2010/115751 A2 | 10/2010 |
| WO | WO 2010/119881 A1 | 10/2010 |
| WO | WO 2011/016469 A1 | 2/2011 |
| WO | WO 2011/016470 A1 | 2/2011 |
| WO | WO 2012/050151 A1 | 4/2012 |
| WO | WO 2013/018675 A1 | 2/2013 |

OTHER PUBLICATIONS

Johnson, A. W. Invitation to Organic Chemistry 1999 Jones and Bartlett: Mississauga, Canada, p. 24.*
Ogawa, et al., Life Sciences, vol. 65, No. 12, pp. 1287-1296 (1999).*
Vickers "The utility of animal models to evaluate novel anti-obesity agents" British Journal of Pharmacology (2011) 164 1248-1262.*
Lutz "Overview of Animal Models of Obesity" Curr Protoc Pharmacol. Sep. 2012; Chapter: Unit 5.61. 1-22.*
King "The use of animal models in diabetes research" British Journal of Pharmacology (2012) 166 877-894.*
International Search Report issued in PCT Application No. PCT/JP2013/050710 on Mar. 26, 2013, 4 pages.

* cited by examiner

*Primary Examiner* — David K O Dell
(74) *Attorney, Agent, or Firm* — Dorsey and Whitney LLP

(57) ABSTRACT

Compounds are provided having an excellent hypoglycemic effect and β cell- or pancreas-protecting effects, or pharmaceutically acceptable salts thereof, and a pharmaceutical composition having an excellent therapeutic effect and/or prophylactic effect on type 1 diabetes, type 2 diabetes, and the like, which cause hyperglycemia due to abnormal glucose metabolism. A compound represented by general formula (I), or a pharmaceutically acceptable salt thereof, is disclosed.

(I)

[Chemical Formula 1]

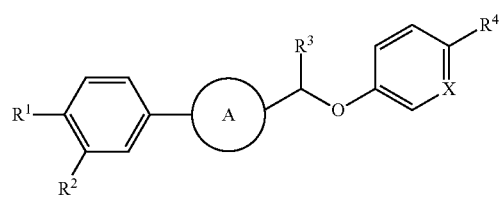

8 Claims, No Drawings

SUBSTITUTED PHENYLAZOLE DERIVATIVES

This application is a national stage application under 35 U.S.C. §371 of International Application No. PCT/JP2013/050710, filed Jan. 17, 2013, entitled "Substituted Phenylazole Derivative," which claims priority to Japanese Patent Application No. 2012-007840, filed Jan. 18, 2012.

TECHNICAL FIELD

The present invention relates to novel substituted phenylazole derivatives which have a hypoglycemic effect and/or a β cell- or pancreas-protecting effect, or pharmaceutically acceptable salts thereof, and pharmaceutical compositions containing those as an active ingredient.

BACKGROUND ART

Diabetes mellitus is a metabolic disease basically characterized by a chronic hyperglycemic state due to impaired insulin action. The treatment of diabetes is generally performed by drug therapy together with diet and exercise therapies. Oral hypoglycemic agents, which are one type of antidiabetic agent, include biguanides and thiazolidinediones that improve insulin resistance; sulfonylureas and glinides that promote insulin secretion from pancreatic β cells; and α-glucosidase inhibitors that inhibit sugar absorption.

However, it is reported that they have side effects: biguanides produce gastrointestinal symptoms and lactic acidosis; thiazolidinediones produce weight gain and edema; sulfonylureas and glinides produce hypoglycemia or secondary failure due to long-term use; and α-glucosidase inhibitors produce diarrhea etc. Therefore, development of an oral hypoglycemic agent which can address such problems is desired. In recent years, compounds having new structures have been developed as oral hypoglycemic agents (see, for example, Patent Literature 1 to 9).

CITATION LIST

Patent Literature

Patent Literature 1: WO 2007/116229
Patent Literature 2: WO 2007/003960
Patent Literature 3: WO 2007/003962
Patent Literature 4: WO 2005/061489
Patent Literature 5: WO 2009/051119
Patent Literature 6: WO 2010/119881
Patent Literature 7: WO 2011/016469
Patent Literature 8: WO 2011/016470
Patent Literature 9: WO 2012/050151

SUMMARY OF THE INVENTION

Problems to be Solved by the Invention

An object of the present invention is to provide a compound which has a new structure that is neither described nor suggested in the above patent literature and has an excellent hypoglycemic effect or a β cell- or pancreas-protecting effect, or a pharmaceutically acceptable salt thereof; a pharmaceutical composition having an excellent therapeutic effect and/or prophylactic effect on type 1 diabetes, type 2 diabetes and the like, which cause an increase in blood sugar levels due to abnormal glucose metabolism; and a pharmaceutical composition having a β cell- or pancreas-protecting effect.

Means for Solving the Problems

The present invention provides:
(1) a compound represented by general formula (I):

(I)

[Chemical Formula 1]

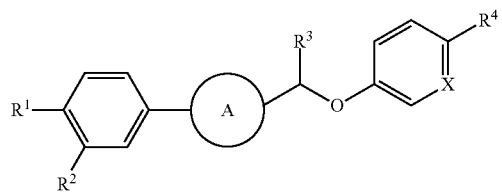

wherein the ring A represents

[Chemical Formula 2]

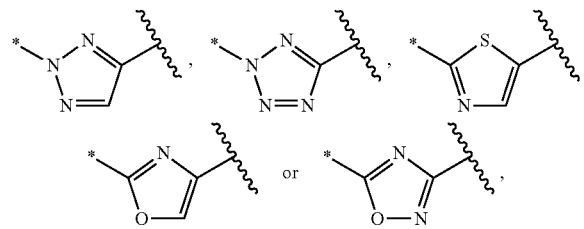

* represents the bonding site with the benzene ring, X represents CH or N, $R^1$ represents —C(=O)—NH—$R^5$, —NH—C(=O)—NH—$R^5$, or —S(=O)$_2$—$R^5$, $R^2$ represents —F or —H, $R^3$ represents —CH$_3$ or —C$_2$H$_5$, $R^4$ represents

[Chemical Formula 3]

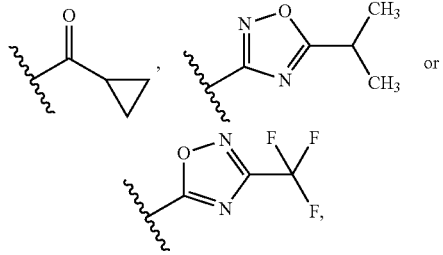

and
$R^5$ represents —H, or represents a C1-C6 alkyl group, a C3-C6 cycloalkyl group, or

[Chemical Formula 4]

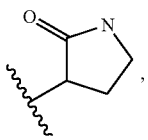

each of which may be substituted with 1 to 3 —OH, or a pharmaceutically acceptable salt thereof;

(2) the compound as set forth in item (1), wherein the ring A represents

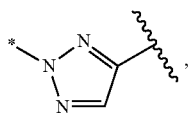
[Chemical Formula 5]

$R^1$ represents —C(=O)—NH—$R^5$ or —NH—C(=O)—NH—$R^5$, $R^2$ represents —F, and $R^4$ represents

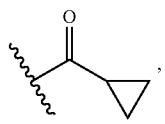
[Chemical Formula 6]

or a pharmaceutically acceptable salt thereof;

(3) the compound as set forth in item (1), wherein the ring A represents

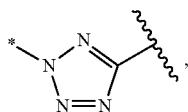
[Chemical Formula 7]

$R^1$ represents —C(=O)—NH—$R^5$, $R^2$ represents —F, $R^4$ represents

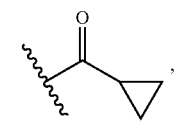
[Chemical Formula 8]

and
$R^5$ represents a hydroxyisopropyl group or a cyclopropyl group, or a pharmaceutically acceptable salt thereof;

(4) the compound as set forth in item (1), wherein the ring A represents

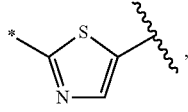
[Chemical Formula 9]

$R^1$ represents —C(=O)—NH—$R^5$ or —S(=O)$_2$—$R^5$, $R^3$ represents —CH$_3$, $R^4$ represents

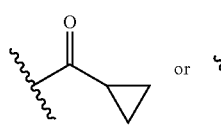
[Chemical Formula 10]

and
$R^5$ represents a C1-C6 alkyl group which may be substituted with 1 to 3 —OH,
or a pharmaceutically acceptable salt thereof;

(5) the compound as set forth in item (1), wherein the ring A represents

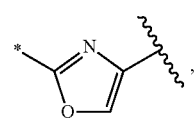
[Chemical Formula 11]

$R^1$ represents —C(=O)—NH—$R^5$ or —NH—C(=O)—NH—$R^5$, $R^2$ represents —F,
$R^3$ represents —CH$_3$, $R^4$ represents

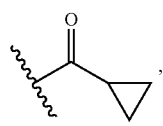
[Chemical Formula 12]

and
$R^5$ represents —H, or represents a C1-C6 alkyl group or a C3-C6 cycloalkyl group, each of which may be substituted with 1 to 3 —OH,
or a pharmaceutically acceptable salt thereof;

(6) the compound as set forth in item (1), wherein the ring A represents

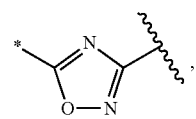
[Chemical Formula 13]

$R^1$ represents —C(=O)—NH—$R^5$ or —NH—C(=O)—NH—$R^5$, $R^2$ represents —F, $R^4$ represents

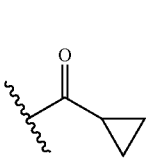
[Chemical Formula 14]

and
$R^5$ represents —H, or represents a C1-C6 alkyl group or a C3-C6 cycloalkyl group, each of which may be substituted with 1 to 3 —OH,
or a pharmaceutically acceptable salt thereof;

(7) a compound represented by general formula (II):

(II)

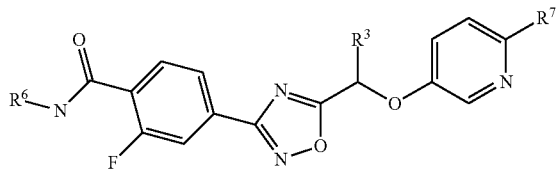

[Chemical Formula 15]

wherein $R^3$ represents —$CH_3$ or —$C_2H_5$, $R^6$ represents a C1-C6 alkyl group or a C3-C6 cycloalkyl group, each of which may be substituted with 1 to 3 —OH, $R^7$ represents

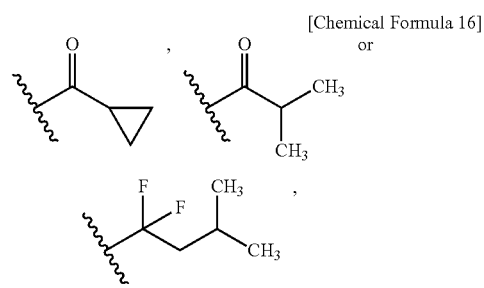

[Chemical Formula 16]

or a pharmaceutically acceptable salt thereof;

(8) a compound represented by general formula (III):

(III)

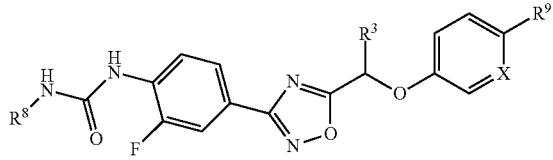

[Chemical Formula 17]

wherein X represents CH or N, $R^3$ represents —$CH_3$ or —$C_2H_5$, $R^8$ represents —H, or represents a C1-C6 alkyl group which may be substituted with 1 to 3 substituents selected from substituent subgroup α, $R^9$ represents

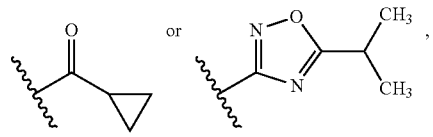

[Chemical Formula 18]

and substituent subgroup α is —OH, —O—C(=O)—O—$CH_3$, or —O—C(=O)—NH—$C_2H_5$, or a pharmaceutically acceptable salt thereof.

(9) a compound selected from the group consisting of the following compounds:
1-[4-(4-{1-[4-(cyclopropylcarbonyl)phenoxy]propyl}-2H-1,2,3-triazol-2-yl)-2-fluorophenyl]-3-(2-hydroxyethyl)urea;
4-{4-[(1R)-1-{[6-(cyclopropylcarbonyl)pyridin-3-yl]oxy}ethyl]-2H-1,2,3-triazol-2-yl}-N-[(1R,2R)-2,3-dihydroxy-1-methylpropyl]-2-fluorobenzamide;
1-(4-{4-[(1R)-1-{[6-(cyclopropylcarbonyl)pyridin-3-yl]oxy}ethyl]-2H-1,2,3-triazol-2-yl}-2-fluorophenyl)-3-(2-hydroxyethyl)urea;
4-(5-{1-[4-(cyclopropylcarbonyl)phenoxy]propyl}-2H-tetrazol-2-yl)-2-fluoro-N-[(1R)-2-hydroxy-1-methylethyl]benzamide;
4-(5-{1-[4-(cyclopropylcarbonyl)phenoxy]ethyl}-1,3-thiazol-2-yl)-2-fluoro-N-[(1R)-2-hydroxy-1-methylethyl]benzamide;
4-[4-(1-({[6-(cyclopropylcarbonyl)pyridin-3-yl]oxy}ethyl)-1,3-oxazol-2-yl]-2-fluoro-N-[(1R)-2-hydroxy-1-methylethyl]benzamide;
N-cyclopropyl-4-[4-(1-{[6-(cyclopropylcarbonyl)pyridin-3-yl]oxy}ethyl)-1,3-oxazol-2-yl]-2-fluorobenzamide;
1-{4-[4-(1-({[6-(cyclopropylcarbonyl)pyridin-3-yl]oxy}ethyl)-1,3-oxazol-2-yl]-2-fluorophenyl}-3-(2-hydroxyethyl)urea;
4-{5-[(1R)-1-{[6-(cyclopropylcarbonyl)pyridin-3-yl]oxy}ethyl]-1,2,4-oxadiazol-3-yl}-2-fluoro-N-[(1R)-2-hydroxy-1-methylethyl]benzamide;
1-{4-[5-(1-{[6-(cyclopropylcarbonyl)pyridin-3-yl]oxy}ethyl)-1,2,4-oxadiazol-3-yl]-2-fluorophenyl}-3-(2-hydroxyethyl)urea;
4-[3-(1-{[6-(cyclopropylcarbonyl)pyridin-3-yl]oxy}ethyl)-1,2,4-oxadiazol-5-yl]-2-fluoro-N-[2-hydroxy-1-(hydroxymethyl)ethyl]benzamide; and
1-{4-[3-(1-{[6-(cyclopropylcarbonyl)pyridin-3-yl]oxy}ethyl)-1,2,4-oxadiazol-5-yl]-2-fluorophenyl}-3-(2-hydroxyethyl)urea;
or a pharmaceutically acceptable salt thereof;

(10) a pharmaceutical composition containing, as an active ingredient, the compound as set forth in any one of items (1) to (9),
or a pharmaceutically acceptable salt thereof;

(11) the pharmaceutical composition as set forth in item (10), for treating type 1 diabetes, type 2 diabetes, or obesity;

(12) the pharmaceutical composition as set forth in item (10), for protecting β cells or the pancreas;

(13) use of the compound as set forth in any one of items (1) to (9), or a pharmaceutically acceptable salt thereof, for producing a pharmaceutical composition;

(14) a method for treating a disease, the method including administering to a mammal the compound as set forth in any one of items (1) to (9), or a pharmaceutically acceptable salt thereof; and

(15) the method as set forth in item (14), wherein the mammal is a human being.

Effects of the Invention

The present invention provides a substituted phenylazole derivative having an excellent hypoglycemic effect, or a β cell- or pancreas-protecting effect, or a pharmaceutically acceptable salt thereof; a pharmaceutical composition having an excellent therapeutic effect and/or prophylactic effect on type 1 diabetes, type 2 diabetes and the like, which cause an increase in blood sugar levels; and a pharmaceutical composition having a β cell- or pancreas-protecting effect.

BEST MODES FOR CARRYING OUT THE INVENTION

One embodiment of the present invention is a compound represented by general formula (II):

(III)

[Chemical Formula 19]

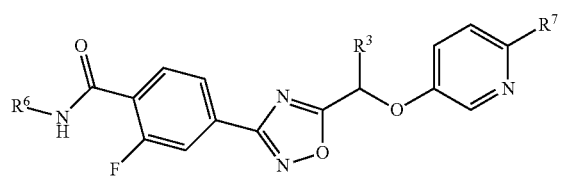

wherein $R^3$ represents —$CH_3$ or —$C_2H_5$, $R^6$ represents a C1-C6 alkyl group or a C3-C6 cycloalkyl group, each of which may be substituted with 1 to 3 —OH, and $R^7$ represents

[Chemical Formula 20]

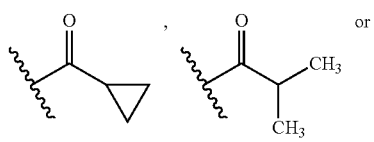

or a pharmaceutically acceptable salt thereof.

One embodiment of the present invention is a compound represented by general formula (III):

(III)

[Chemical Formula 21]

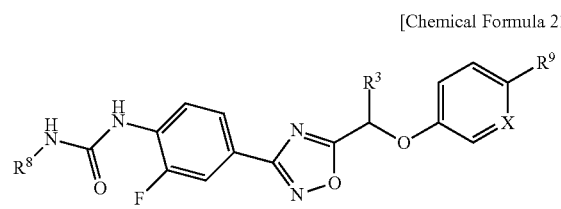

wherein X represents CH or N, $R^3$ represents —$CH_3$ or —$C_2H_5$, $R^8$ represents —H, or represents a C1-C6 alkyl group which may be substituted with 1 to 3 substituents selected from substituent subgroup α, $R^9$ represents

[Chemical Formula 22]

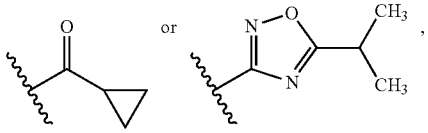

and
substituent subgroup α is —OH, —O—C(=O)—O—$CH_3$, or —O—C(=O)—NH—$C_2H_5$; or a pharmaceutically acceptable salt thereof.

One embodiment of the present invention is a compound represented by general formula (IV):

(IV)

[Chemical Formula 23]

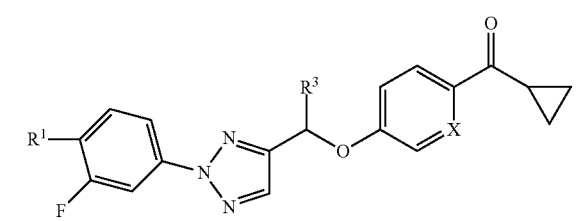

wherein X, $R^1$, and $R^3$ have the same meanings as defined above; or a pharmaceutically acceptable salt thereof.

One embodiment of the present invention is a compound represented by general formula (V):

(V)

[Chemical Formula 24]

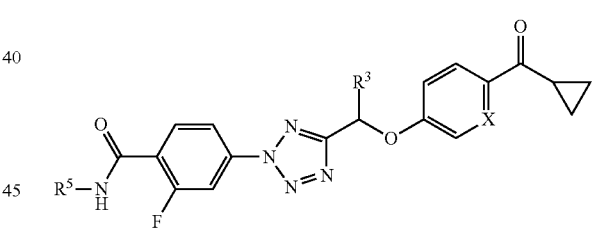

wherein X, $R^3$, and $R^5$ have the same meanings as defined above; or a pharmaceutically acceptable salt thereof.

One embodiment of the present invention is a compound represented by general formula (VI):

(VI)

[Chemical Formula 25]

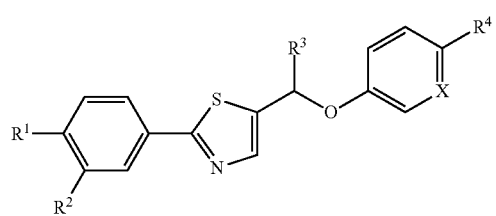

wherein X, $R^1$, $R^2$, $R^3$ and $R^4$ have the same meanings as defined above; or a pharmaceutically acceptable salt thereof.

One embodiment of the present invention is a compound represented by general formula (VII):

(VII)

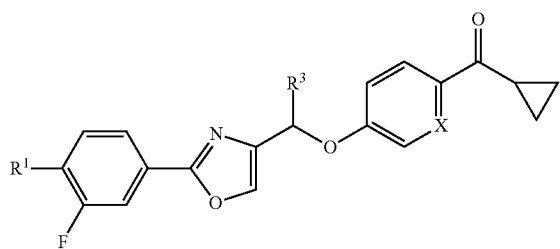

[Chemical Formula 26]

wherein X, $R^1$, and $R^3$ have the same meanings as defined above; or a pharmaceutically acceptable salt thereof.

One embodiment of the present invention is a compound represented by general formula (VIII):

(VIII)

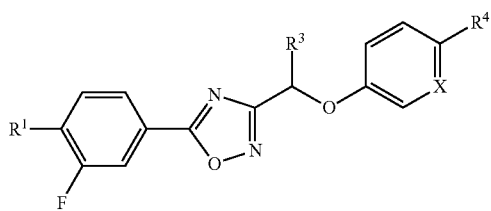

[Chemical Formula 27]

wherein X, $R^1$, $R^3$, and $R^4$ have the same meanings as defined above; or a pharmaceutically acceptable salt thereof.

A "C1-C6 alkyl group" as used in the present specification means a linear or branched alkyl group having 1 to 6 carbon atoms. Specific examples include a methyl group, an ethyl group, a propyl group, an isopropyl group, a butyl group, an isobutyl group, a sec-butyl group, and a tert-butyl group.

A "C3-C6 cycloalkyl group" as used in the present specification means a saturated cyclic hydrocarbon group having 3 to 6 carbon atoms, and examples include a cyclopropyl group, a cyclobutyl group, a cyclopentyl group, and a cyclohexyl group.

A "pharmaceutically acceptable salt" as used in the present specification means a salt formed by allowing the compound of the present invention to react with an acid or a base.

Examples of the salt include hydrohalogenic acid salts such as hydrofluorides, hydrochlorides, hydrobromides, and hydroiodides; inorganic acid salts such as nitrates, perchlorates, sulfates and phosphates; lower alkanesulfonic acid salts such as methanesulfonates, trifluoromethanesulfonates, and ethanesulfonates; arylsulfonic acid salts such as benzenesulfonates, and p-toluenesulfonates; organic acid salts such as acetates, malates, fumarates, succinates, citrates, ascorbates, tartrates, oxalates, and maleates; alkali metal salts such as sodium salts, potassium salts, and lithium salts; alkaline earth metal salts such as calcium salts and magnesium salts; metal salts such as aluminum salts and iron salts; inorganic salts such as ammonium salts; amine salts including organic salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethylammonium salts, and tris(hydroxymethyl)aminomethane salts; and amino acid salts such as glycine salts, lysine salts, arginine salts, ornithine salts, glutamates, and aspartates.

The compound of the present invention absorbs water when, for example, left to stand in the atmosphere, and a hydrate may be formed. Therefore, such a hydrate is also included in the concept of the salt of the present invention.

Since the compound of the present invention may have asymmetric carbon atoms in the molecule, the compound has optical isomers. These isomers and mixtures of these isomers are all represented by a single formula, that is, the general formula (I) to (VIII). Therefore, the present invention encompasses all of the optical isomers of the compound represented by the general formula (I) to (VIII), and mixtures of these optical isomers at any ratios. Such an optical isomer can be produced by, for example, using raw materials having optical activity instead of the raw materials shown in the Reference Examples and Examples that will be described below. Such an optical isomer can also be obtained by subjecting a compound that has been produced by making reference to the Reference Examples, Examples and the like that will be described below, to an optical resolution method that is known in the pertinent art, for example, a diastereomer method, an enzymatic reaction method, an optical resolution method based on chromatography or the like.

The present invention may also encompass compounds in which one or more of the atoms constituting the compound represented by the general formula (I) to (VIII) have been substituted with isotopes of the atoms. Isotopes include the two classes of radioactive isotopes and stable isotopes, and examples of the isotopes include, for example, isotopes of hydrogen ($^2$H and $^3$H), isotopes of carbon ($^{11}$C, $^{13}$C and $^{14}$C), isotopes of nitrogen ($^{13}$N and $^{18}$N), isotopes of oxygen and $^{18}$O), and isotopes of fluorine ($^{18}$F). A composition containing a compound labeled with an isotope is useful as, for example, a therapeutic agent, a prophylactic agent, a research reagent, an assay reagent, a diagnostic agent, or an in vivo diagnostic imaging agent. Compounds labeled with isotopes and mixtures of compounds labeled with isotopes at any ratios are all included in the present invention. A compound labeled with an isotope can be produced by a method that is known in the pertinent art, for example, using raw materials labeled with isotopes instead of the raw materials used in the production methods that will be described below.

The present invention may also encompass prodrugs of the compound represented by the general formula (I) to (VIII). A prodrug is a derivative of the compound represented by the general formula (I) to (VIII), and means a compound which is enzymatically or chemically converted to the compound of the present invention in the living body.

Examples of a prodrug include compounds in which an amino group in the molecule has been acylated, alkylated or phosphorylated; and compounds in which a hydroxyl group in the molecule has been acylated, alkylated or phosphorylated (see, for example, Povl Krogsgaard-Larsen, et al., "A Textbook of Drug Design and Development", Second Edition, Harwood Academic Publishers, 1996, pp. 351-385). Such a prodrug can be produced from the compound represented by the general formula (I) to (VIII) by a method known in the pertinent art.

The compound of the present invention can be easily produced from known compounds according to the Reference Examples and Examples that will be described below.

The compound of the present invention or a pharmaceutically acceptable salt thereof has an excellent hypoglycemic effect, and can therefore be used as an active ingredient of a pharmaceutical composition that can be used in the treatment and/or prevention of type 1 diabetes, type 2 diabetes, gestational diabetes, hyperglycemia due to other factors, impaired glucose tolerance (IGT), obesity, diabetes-associated diseases (for example, hyperlipidemia, hypercholesterolemia, abnormal lipid metabolism, hypertension, fatty liver, metabolic syndrome, edema, heart failure, angina pectoris, myocardial infarction, arteriosclerosis, hyperuricemia, and gout), or diabetic complications (for example, retinosis, kidney failure, neuropathy, cataract, gangrenous leg, infections, and ketosis).

The compound of the present invention or a pharmaceutically acceptable salt thereof has an excellent β cell- or pancreas-protecting effect, and can therefore be used as an active ingredient of a pharmaceutical composition that can be used for protecting β cells or the pancreas.

The compound of the present invention or a pharmaceutically acceptable salt thereof can also be used in combination with other therapeutic drugs for diabetes, diabetic complications, hyperlipidemia, hypertension, and the like.

When a pharmaceutical composition containing the compound of the present invention or a pharmaceutically acceptable salt thereof is administered to a mammal (for example, human, horse, cow or pig; preferably a human being), the pharmaceutical composition can be administered systemically or topically, and orally or parenterally.

Appropriate dosage forms of the pharmaceutical composition of the present invention can be selected in accordance with the administration mode. The pharmaceutical composition of the present invention can be prepared according to the preparation methods for various conventionally used formulations.

Examples of the dosage form of the pharmaceutical composition for oral use include tablets, pills, powders, granules, capsules, liquids, suspensions, emulsions, syrups, and elixirs. Pharmaceutical compositions of such dosage forms can be prepared according to conventional methods, by appropriately selecting, as necessary, excipients, binders, disintegrants, lubricating agents, swelling agents, swelling aids, coating agents, plasticizers, stabilizers, antiseptics, antioxidants, colorants, dissolution aids, suspending agents, emulsifiers, sweeteners, preservatives, buffers, diluents, wetting agents and the like, which are conventionally used as additives.

Examples of the dosage forms of a pharmaceutical composition for parenteral use include injections, ointments, gels, creams, poultices, patches, aerosols, inhalants, sprays, eye drops, nose drops, and suppositories. Pharmaceutical compositions of such dosage forms can be prepared according to conventional methods, by appropriately selecting as necessary, stabilizers, antiseptics, dissolution aids, moisturizers, preservatives, antioxidants, fragrances, gelling agents, neutralizing agents, buffers, isotonic agents, surfactants, colorants, buffering agents, thickeners, wetting agents, fillers, absorption promoting agents, suspending agents, binders, and the like, which are conventionally used as additives.

The administration amount of the compound of the present invention or a pharmaceutically acceptable salt thereof may vary with the symptoms, age, body weight or the like. However, in the case of oral administration, the compound or the salt is administered once to several times a day, in an amount of 1 to 2000 mg, and preferably 1 to 400 mg, in terms of the compound, per dose for an adult; and in the case of parenteral administration, the compound or the salt is administered once to several times a day, in an amount of 0.01 to 500 mg, and preferably 0.1 to 300 mg, in terms of the compound, per dose for an adult.

Hereinafter, the present invention will be described in more detail by way of Reference Examples, Examples, a Formulation Example and Test Examples, but the scope of the present invention is not intended to be limited to these.

EXAMPLES

Reference Example 1

Ethyl 2-[3-fluoro-4-(methoxycarbonyl)phenyl]-2H-1,2,3-triazol-4-carboxylate

[Chemical Formula 28]

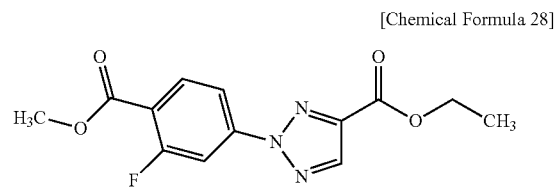 [SMILES: CCOC(=O)c1cnn(-c2ccc(C(=O)OC)c(F)c2)n1]

Methyl 4-amino-2-fluorobenzoate (Bioorg. Med. Chem. 2009, 17, 7042-7051.) (13.0 g, 76.9 mmol) was suspended in a 3 N aqueous hydrochloric acid solution (108 mL), and an aqueous (25 mL) solution of sodium nitrite (5.57 g, 80.7 mmol) was added to the resulting suspension over 10 minutes under ice cooling. The resulting mixture was stirred at the same temperature for 30 minutes, and then the obtained reaction mixture was added to a mixed water (412 mL) and ethanol (52 mL) suspension of sodium acetate (82.0 g) and 3-dimethylamino ethyl acrylate (14.3 mL) over 5 minutes under ice cooling. The resulting mixture was stirred at the same temperature for 90 minutes. Subsequently, water was added to the reaction mixture, and the resulting mixture was extracted twice with dichloromethane. The organic layer thus obtained was dried over anhydrous sodium sulfate. The resulting mixture was filtered, and then the solvent was distilled off under reduced pressure. The resulting residue was diluted with ethanol (228 mL) and water (114 mL), and then hydroxylamine hydrochloride (6.06 g, 84.5 mmol) and sodium acetate (13.9 g, 169 mmol) were added to the resulting mixture. The mixture was stirred at room temperature for 2.5 hours. Subsequently, water was added to the reaction mixture, and the resulting mixture was extracted with dichloromethane. The organic layer thus obtained was dried over anhydrous sodium sulfate. The resulting mixture was filtered, then the solvent was distilled off under reduced pressure, and the resulting residue was diluted with acetic acid (120 mL) and acetic anhydride (179 mL). The resulting mixture was stirred at 60° C. for 1 hour, and then the solvent in the reaction mixture was distilled off under reduced pressure. The resulting residue was diluted with tetrahydrofuran (239 mL), and then potassium carbonate (106 g, 0.769 mol) was added to the resulting mixture. The mixture was stirred at room temperature for 1 hour. Subsequently, water was added to the reaction mixture, and the resulting mixture was extracted twice with dichloromethane. The organic layer thus obtained was dried over anhydrous sodium sulfate. The resulting mixture was filtered, then the solvent was distilled off under reduced pressure, and the resulting residue was purified by silica gel column chromatography (dichloromethane) to give the title compound (15.9 g, yield: 71%).

$^1$H-NMR (400 MHz, CDCl$_3$) δ ppm:
8.27 (1H, s), 8.13-7.98 (3H, m), 4.49 (2H, q, J=7 Hz), 3.97 (3H, s), 1.45 (3H, t, J=7 Hz).

Reference Example 2

2-[3-Fluoro-4-(methoxycarbonyl)phenyl]-2H-1,2,3-triazol-4-carboxylic acid

[Chemical Formula 29]

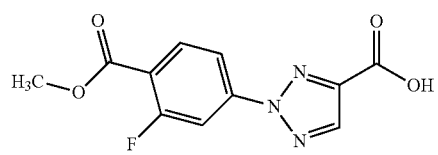

1 N Aqueous sodium hydroxide solution (59.6 mL) was added dropwise to a methanol (159 mL) and tetrahydrofuran (159 mL) mixed solution of the compound obtained in Reference Example 1 (15.9 g, 54.2 mmol) at room temperature over 5 minutes, and the mixture was stirred at the same temperature for 1.5 hours. Subsequently, water and diethyl ether were added to the reaction mixture, and the mixture was separated into two layers. 1 N Aqueous hydrochloric acid solution (59.6 mL) was added to the aqueous layer thus obtained, and the mixture was extracted with dichloromethane. The organic layer thus obtained was dried over anhydrous sodium sulfate. The resulting mixture was filtered, and then the solvent was distilled off under reduced pressure to give the title compound (12.6 g, yield: 88%).

$^1$H-NMR (400 MHz, DMSO-d$_6$) δ ppm:
13.80 (1H, m), 8.63 (1H, s), 8.16-7.92 (3H, m), 3.90 (3H, s).

Reference Example 3

Methyl 2-fluoro-4-{4-[methoxy(methyl)carbamoyl]-2H-1,2,3-triazol-2-yl}benzoate

[Chemical Formula 30]

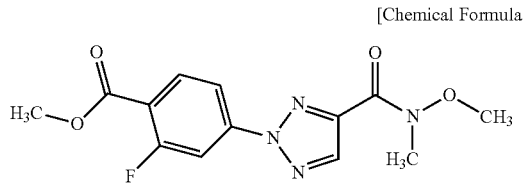

Triethylamine (15.9 mL, 0.114 mol) was added to a dichloromethane (189 mL) suspension of the compound obtained in Reference Example 2 (12.6 g, 47.5 mmol), N,O-dimethylhydroxylamine hydrochloride (5.56 g, 57.0 mmol), N-(3-dimethylaminopropyl)-N'-ethylcarbodiimide hydrochloride (10.9 g, 57.0 mmol), and 1-hydroxybenzotriazole monohydrate (8.73 g, 57.0 mmol) under ice cooling. The mixture was stirred at the same temperature for 15 minutes, and at room temperature for 18 hours. Subsequently, water was added to the reaction mixture, and the resulting mixture was extracted with dichloromethane. The organic layer thus obtained was dried over anhydrous sodium sulfate. The resulting mixture was filtered, then the solvent was distilled off under reduced pressure, and the resulting residue was purified by silica gel column chromatography (10% ethyl acetate/dichloromethane) to give the title compound (9.65 g, yield: 66%).

$^1$H-NMR (400 MHz, CDCl$_3$) δ ppm:
8.25 (1H, s), 8.13-7.95 (3H, m), 3.97 (3H, s), 3.85 (3H, s), 3.46 (3H, br s).

Reference Example 4

Methyl 2-fluoro-4-(4-propionyl-2H-1,2,3-triazol-2-yl)benzoate

[Chemical Formula 31]

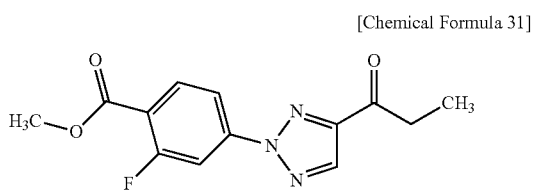 [SMILES: CCC(=O)c1cnn(-c2ccc(C(=O)OC)c(F)c2)n1]

Ethylmagnesium chloride (containing 10 mol % zinc chloride as an activator, 1.0 mol/L tetrahydrofuran solution, 7.04 mL, 7.04 mmol) was added dropwise to a tetrahydrofuran (33 mL) suspension of the compound obtained in Reference Example 3 (1.67 g, 5.42 mmol) under ice cooling. The mixture was stirred at the same temperature for 35 minutes, and then ethylmagnesium chloride (the same as the above, 3.52 mL, 3.52 mmol) was further added. The mixture was stirred at the same temperature for 20 minutes, and then ethylmagnesium chloride (the same as the above, 3.52 mL, 3.52 mmol) was further added. The mixture was stirred at the same temperature for 10 minutes. Subsequently, water was added to the reaction mixture, and the resulting mixture was extracted with ethyl acetate. The organic layer thus obtained was dried over anhydrous sodium sulfate. The resulting mixture was filtered, then the solvent was distilled off under reduced pressure, and the resulting residue was purified by silica gel column chromatography (dichloromethane) to give the title compound (0.921 g, yield: 61%).

$^1$H-NMR (400 MHz, CDCl$_3$) δ ppm:
8.27 (1H, s), 8.14-8.10 (1H, m), 8.02-7.95 (2H, m), 3.98 (3H, s), 3.16-3.11 (2H, m), 1.29-1.25 (3H, m).

Reference Example 5

Methyl 2-fluoro-4-[4-(1-hydroxypropyl)-2H-1,2,3-triazol-2-yl]benzoate

[Chemical Formula 32]

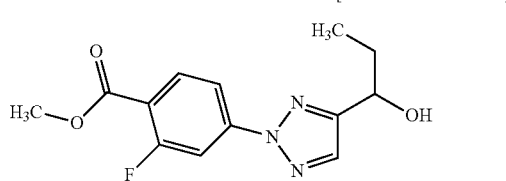

Sodium borohydride (49.8 mg) was added to a mixed methanol (5 mL) and tetrahydrofuran (5 mL) suspension of the compound obtained in Reference Example 4 (0.231 g, 0.833 mmol) under ice cooling. The mixture was stirred at the same temperature for 2 hours. Subsequently, water was added to the reaction mixture, and the resulting mixture was extracted with ethyl acetate. The organic layer thus obtained was dried over anhydrous sodium sulfate. The resulting mixture was filtered, then the solvent was distilled off under reduced pressure, and the resulting residue was purified by silica gel column chromatography (25% ethyl acetate/hexane) to give the title compound (0.213 g, yield: 92%).

$^1$H-NMR (400 MHz, CDCl$_3$) δ ppm:
8.09-8.05 (1H, m), 7.93-7.85 (2H, m), 7.81 (1H, s), 4.94-4.89 (1H, m), 3.96 (3H, s), 2.20-2.19 (1H, m), 2.01-1.88 (2H, m), 1.05-1.02 (3H, m).

Reference Example 6

Methyl 4-(4-{1-[4-(cyclopropylcarbonyl)phenoxy]propyl}-2H-1,2,3-triazol-2-yl)-2-fluorobenzoate

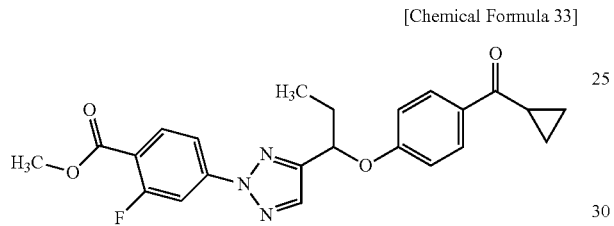

[Chemical Formula 33]

Di-tert-butyl azodicarboxylate (0.187 g, 0.811 mmol) was added to a tetrahydrofuran (5 mL) solution of the compound obtained in Reference Example 5 (0.206 g, 0.738 mmol), cyclopropyl(4-hydroxyphenyl)methanone (0.132 g, 0.811 mmol), and triphenylphosphine (0.213 g, 0.811 mmol) at room temperature. The mixture was stirred at room temperature for 5.5 hours. Subsequently, the solvent in the reaction mixture was distilled off under reduced pressure. The resulting residue was purified by silica gel column chromatography (20% ethyl acetate/hexane) to give the title compound (0.295 g, yield: 94%).

$^1$H-NMR (400 MHz, CDCl$_3$) δ ppm:
8.10-8.06 (1H, m), 7.98-7.86 (4H, m), 7.76 (1H, s), 7.01-6.99 (2H, m), 5.52-5.49 (1H, m), 3.96 (3H, s), 2.62-2.56 (1H, m), 2.21-2.07 (2H, m), 1.20-1.17 (2H, m), 1.10-1.06 (3H, m), 1.00-0.97 (2H, m).

Reference Example 7

4-(4-{1-[4-(Cyclopropylcarbonyl)phenoxy]propyl}-2H-1,2,3-triazol-2-yl)-2-fluorobenzoic acid

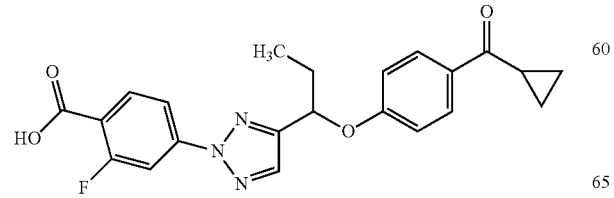

[Chemical Formula 34]

1 N Aqueous sodium hydroxide solution (0.73 mL) was added to a tetrahydrofuran (5.6 mL) solution of the compound obtained in Reference Example 6 (0.282 g, 0.666 mmol) at room temperature. The mixture was stirred at 60° C. for 1 hour, and then 1 N aqueous sodium hydroxide solution (0.73 mL) was further added. The mixture was stirred at 60° C. for 1 hour, and then returned to room temperature. Subsequently, water and diethyl ether were added to the reaction mixture, and the mixture was separated into two layers. 1 N Aqueous hydrochloric acid solution (1.46 mL) was added to the aqueous layer thus obtained, and the mixture was extracted twice with dichloromethane. The organic layer thus obtained was dried over anhydrous sodium sulfate. The resulting mixture was filtered, and then the solvent was distilled off under reduced pressure to give the title compound (0.243 g, yield: 89%).

$^1$H-NMR (400 MHz, CDCl$_3$) δ ppm:
8.19-8.15 (1H, m), 7.99-7.89 (4H, m), 7.78 (1H, s), 7.03-6.99 (2H, m), 5.53-5.50 (1H, m), 2.63-2.56 (1H, m), 2.22-2.06 (2H, m), 1.21-1.17 (2H, m), 1.11-1.07 (3H, m), 1.01-0.96 (2H, m).

Reference Example 8

Methyl 4-(4-acetyl-2H-1,2,3-triazol-2-yl)-2-fluorobenzoate

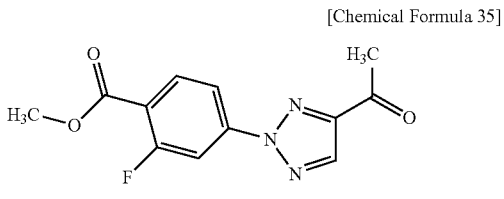 [SMILES: COC(=O)c1ccc(-n2ncc(C(C)=O)n2)cc1F]

[Chemical Formula 35]

Methylmagnesium bromide (0.99 mol/L tetrahydrofuran solution, 34.6 mL, 34.3 mmol) was added dropwise to a tetrahydrofuran (132 mL) suspension of the compound obtained in Reference Example 3 (6.60 g, 21.4 mmol) under ice cooling. The mixture was stirred at the same temperature for 1 hour. Subsequently, water was added to the reaction mixture, and the resulting mixture was extracted with ethyl acetate. The organic layer thus obtained was dried over anhydrous sodium sulfate. The resulting mixture was filtered, then the solvent was distilled off under reduced pressure, and the resulting residue was purified by silica gel column chromatography (dichloromethane) to give the title compound (4.63 g, yield: 82%).

$^1$H-NMR (400 MHz, CDCl$_3$) δ ppm:
8.26 (1H, s), 8.15-8.11 (1H, m), 8.03-7.95 (2H, m), 3.98 (3H, s), 2.71 (3H, s).

Reference Example 9

Methyl 2-fluoro-4-[4-(1-hydroxyethyl)-2H-1,2,3-triazol-2-yl]benzoate

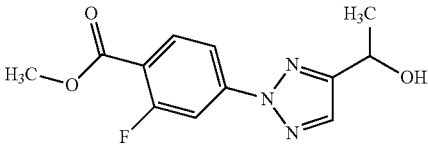

[Chemical Formula 36]

Sodium borohydride (42.0 mg) was added to a methanol (4 mL) suspension of the compound obtained in Reference Example 8 (0.185 g, 0.703 mmol) under ice cooling. The mixture was stirred at the same temperature for 5 hours. Subsequently, water was added to the reaction mixture, and the resulting mixture was extracted with ethyl acetate. The organic layer thus obtained was dried over anhydrous sodium sulfate. The resulting mixture was filtered, then the solvent was distilled off under reduced pressure, and the resulting residue was purified by silica gel column chromatography (15% ethyl acetate/dichloromethane) to give the title compound (0.174 g, yield: 93%).

$^1$H-NMR (400 MHz, CDCl$_3$) δ ppm:
8.10-8.05 (1H, m), 7.93-7.86 (2H, m), 7.83 (1H, s), 5.19-5.12 (1H, m), 3.96 (3H, s), 1.65 (3H, d, J=7 Hz).

Reference Example 10

Methyl 4-(4-{1-[4-(cyclopropylcarbonyl)phenoxy]ethyl}-2H-1,2,3-triazol-2-yl)-2-fluorobenzoate

[Chemical Formula 37]

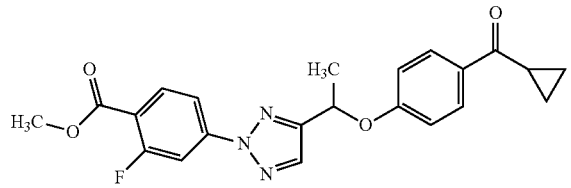

Di-tert-butyl azodicarboxylate (0.165 g, 0.717 mmol) was added to a tetrahydrofuran (4 mL) solution of the compound obtained in Reference Example 9 (0.173 g, 0.652 mmol), cyclopropyl(4-hydroxyphenyl)methanone (0.116 g, 0.717 mmol), and triphenylphosphine (0.188 g, 0.717 mmol) at room temperature. The mixture was stirred at room temperature for 1 hour. Subsequently, the solvent in the reaction mixture was distilled off under reduced pressure. The resulting residue was purified by silica gel column chromatography (20% ethyl acetate/hexane) to give the title compound (0.293 g, quantitative).

$^1$H-NMR (400 MHz, CDCl$_3$) δ ppm:
8.10-8.06 (1H, m), 7.99-7.97 (2H, m), 7.93-7.86 (2H, m), 7.80 (1H, s), 7.04-7.00 (2H, m), 5.77-5.73 (1H, m), 3.96 (3H, s), 2.63-2.57 (1H, m), 1.80 (3H, d, J=7 Hz), 1.21-1.18 (2H, m), 1.01-0.96 (2H, m).

Reference Example 11

4-(4-{1-[4-(Cyclopropylcarbonyl)phenoxy]ethyl}-2H-1,2,3-triazol-2-yl)-2-fluorobenzoic acid

[Chemical Formula 38]

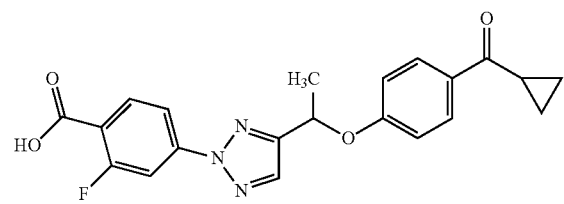

1 N Aqueous sodium hydroxide solution (1.43 mL) was added to a tetrahydrofuran (5.8 mL) solution of the compound obtained in Reference Example 10 (0.290 g) at room temperature. The mixture was stirred at 60° C. for 1 hour, and then returned to room temperature. Subsequently, water and diethyl ether were added to the reaction mixture, and the mixture was separated into two layers. 1 N Aqueous hydrochloric acid solution (1.43 mL) was added to the aqueous layer thus obtained, and the mixture was extracted twice with dichloromethane. The organic layer thus obtained was dried over anhydrous sodium sulfate. The resulting mixture was filtered, and then the solvent was distilled off under reduced pressure to give the title compound (0.226 g, yield: 88%).

$^1$H-NMR (400 MHz, DMSO-d$_6$) δ ppm:
8.32 (1H, s), 8.12-8.01 (3H, m), 7.94-7.85 (2H, m), 7.18-7.16 (2H, m), 6.02-5.97 (1H, m), 2.87-2.80 (1H, m), 1.75 (3H, d, J=6 Hz), 0.98-0.96 (4H, m).

Reference Example 12

2-Fuoro-4-(4-propionyl-2H-1,2,3-triazol-2-yl)benzoic acid

[Chemical Formula 39]

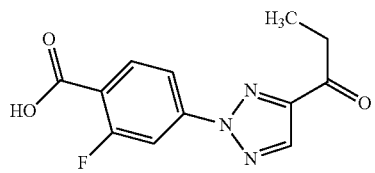

1 N Aqueous sodium hydroxide solution (7.30 mL) was added to a tetrahydrofuran (18 mL) solution of the compound obtained in Reference Example 4 (0.920 g, 3.32 mmol) at room temperature. The mixture was stirred at 60° C. for 1.5 hours, and then returned to room temperature. Subsequently, water and diethyl ether were added to the reaction mixture, and the mixture was separated into two layers. 1 N Aqueous hydrochloric acid solution (7.30 mL) was added to the aqueous layer thus obtained, and the mixture was extracted twice with dichloromethane. The organic layer thus obtained was dried over anhydrous sodium sulfate. The resulting mixture was filtered, and then the solvent was distilled off under reduced pressure to give the title compound (0.830 g, yield: 95%).

$^1$H-NMR (400 MHz, DMSO-d$_6$) δ ppm:
13.54 (1H, br s), 8.67 (1H, s), 8.15-8.11 (1H, m), 8.04-7.97 (2H, m), 3.16-3.10 (2H, m), 1.15-1.12 (3H, m).

Reference Example 13 tert-Butyl 2-fluoro-4-(4-propionyl-2H-1,2,3-triazol-2-yl)benzoate

[Chemical Formula 40]

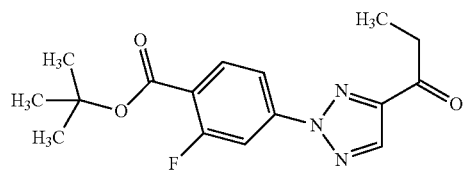

N,N-Dimethylformamide di-tert-butylacetal (1.50 mL, 6.27 mmol) was added to a dichloromethane (16.5 mL) suspension of the compound obtained in Reference Example 12 (0.920 g, 3.13 mmol) at room temperature. The mixture was stirred at room temperature for 19 hours, and then N,N-dimethylformamide di-tert-butylacetal (6.00 mL, 25.1 mmol) was further added. The mixture was stirred at room temperature for 22 hours. Subsequently, the solvent in the reaction mixture was distilled off under reduced pressure. The resulting residue was purified by silica gel column chromatography (dichloromethane) to give the title compound (0.370 g, yield: 37%).

¹H-NMR (400 MHz, CDCl₃) δ ppm:

8.26 (1H, s), 8.06-8.02 (1H, m), 7.98-7.90 (2H, m), 3.14 (2H, q, J=7 Hz), 1.62 (9H, s), 1.27 (3H, t, J=7 Hz).

Reference Example 14 tert-Butyl 2-fluoro-4-[4-(1-hydroxypropyl)-2H-1,2,3-triazol-2-yl]benzoate

[Chemical Formula 41]

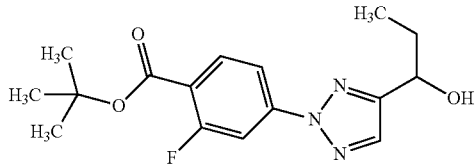

Sodium borohydride (100 mg, 2.52 mmol) was added to a methanol (7 mL) and tetrahydrofuran (7 mL) solution of the compound obtained in Reference Example 13 (0.366 g, 1.15 mmol) under ice cooling. The mixture was stirred at the same temperature for 1 hour. Subsequently, water was added to the reaction mixture, and the resulting mixture was extracted with ethyl acetate. The organic layer thus obtained was dried over anhydrous sodium sulfate. The resulting mixture was filtered, then the solvent was distilled off under reduced pressure, and the resulting residue was purified by silica gel column chromatography (25% ethyl acetate/hexane) to give the title compound (0.381 g, quantitative).

¹H-NMR (400 MHz, CDCl₃) δ ppm:

8.00-7.96 (1H, m), 7.89-7.81 (3H, m), 7.80 (3H, s), 4.93-4.89 (1H, m), 2.21-2.20 (1H, m), 2.01-1.88 (2H, m), 1.61 (9H, s), 1.06-1.02 (3H, m).

Reference Example 15 tert-Butyl 2-fluoro-4-{4-[(1S)-1-hydroxypropyl]-2H-1,2,3-triazol-2-yl}benzoate

[Chemical Formula 42]

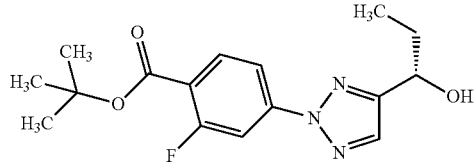

Lipase (acrylic resin support, from *Candida antarctica*) (45.4 mg), and vinyl acetate (0.138 mL, 1.49 mmol) were added to a toluene (5.70 mL) solution of the compound obtained in Reference Example 14 (0.369 g) at room temperature. The mixture was stirred at room temperature for 24 hours. Subsequently, lipase (acrylic resin support, from *Candida antarctica*) (45.4 mg), and vinyl acetate (0.138 mL, 1.49 mmol) were further added. The mixture was stirred at room temperature for 24 hours. Subsequently, the solid in the reaction mixture was filtered. The solvent in the filtrate thus obtained was distilled off under reduced pressure. The resulting residue was purified by silica gel column chromatography (15%-25% ethyl acetate/hexane) to give an ingredient, which was diluted with toluene (2.90 mL). Lipase (the same as the above) (24.0 mg), and vinyl acetate (0.0722 mL, 0.781 mmol) were added to the resulting mixture at room temperature. The mixture was stirred at room temperature for 67 hours. Subsequently, the solid in the reaction mixture was filtered. The solvent in the filtrate thus obtained was distilled off under reduced pressure. The resulting residue was purified by silica gel column chromatography (15%-25% ethyl acetate/hexane) to give the title compound (0.179 g, yield: 49%).

¹H-NMR (400 MHz, CDCl₃) δ ppm:

8.00-7.96 (1H, m), 7.89-7.81 (3H, m), 7.80 (3H, s), 4.93-4.89 (1H, m), 2.17-2.16 (1H, m), 2.00-1.90 (2H, m), 1.62 (9H, s), 1.06-1.02 (3H, m).

Reference Example 16 tert-Butyl 4-(4-{(1R)-1-[4-(cyclopropylcarbonyl)phenoxy]propyl}-2H-1,2,3-triazol-2-yl)-2-fluorobenzoate

[Chemical Formula 43]

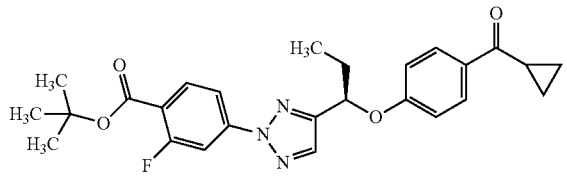

Di-tert-butyl azodicarboxylate (0.136 g, 0.589 mmol) was added to a tetrahydrofuran (4 mL) solution of the compound obtained in Reference Example 15 (0.172 g, 0.535 mmol), cyclopropyl(4-hydroxyphenyl)methanone (95.5 mg, 0.589 mmol), and triphenylphosphine (0.154 g, 0.589 mmol) at room temperature. The mixture was stirred at room temperature for 22 hours. Subsequently, the solvent in the reaction mixture was distilled off under reduced pressure. The resulting residue was purified by silica gel column chromatography (12% ethyl acetate/hexane) to give the title compound (0.293 g, yield: 74%).

¹H-NMR (400 MHz, CDCl₃) δ ppm:

8.02-7.94 (3H, m), 7.89-7.81 (2H, m), 7.75 (1H, s), 7.03-6.99 (2H, m), 5.52-5.49 (1H, m), 2.62-2.56 (1H, m), 2.21-2.07 (2H, m), 1.62 (9H, s), 1.20-1.17 (2H, m), 1.10-1.07 (3H, m), 1.00-0.96 (2H, m).

Reference Example 17

4-(4-{(1R)-1-[4-(Cyclopropylcarbonyl)phenoxy]propyl}-2H-1,2,3-triazol-2-yl)-2-fluorobenzoic acid

[Chemical Formula 44]

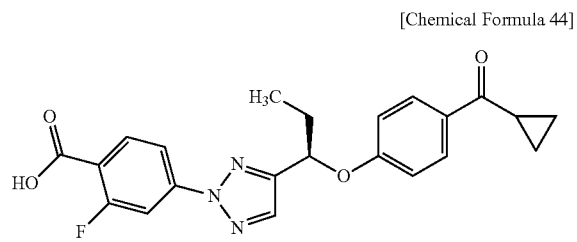 [SMILES: CC[C@@H](Oc1ccc(C(=O)C2CC2)cc1)c1cnn(-c2ccc(C(=O)O)c(F)c2)n1]

Trifluoroacetic acid (1.80 mL) was added to a dichloromethane (5.40 mL) solution of the compound obtained in Reference Example 16 (0.180 g, 0.387 mmol) at room temperature. The mixture was stirred at room temperature for 2 hours. Subsequently, the solvent in the reaction mixture was distilled off under reduced pressure. Diethyl ether and hexane were added to the resulting residue, and the precipitated solid was filtered to give the title compound (0.114 g, yield: 72%).

$^1$H-NMR (400 MHz, CDCl$_3$) δ ppm:
8.19-8.15 (1H, m), 7.99-7.89 (4H, m), 7.78 (1H, s), 7.03-6.99 (2H, m), 5.53-5.50 (1H, m), 2.63-2.56 (1H, m), 2.22-2.06 (2H, m), 1.21-1.17 (2H, m), 1.11-1.07 (3H, m), 1.01-0.96 (2H, m).

Reference Example 18

4-(4-Acetyl-2H-1,2,3-triazol-2-yl)-2-fluorobenzoic acid

[Chemical Formula 45]

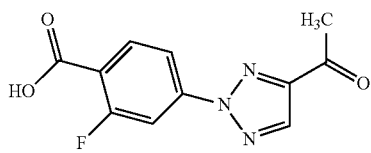

1 N Aqueous sodium hydroxide solution (25.1 mL) was added to a tetrahydrofuran (60 mL) solution of the compound obtained in Reference Example 8 (3.00 g, 11.4 mmol) at room temperature. The mixture was stirred at 60° C. for 1 hour, and then returned to room temperature. Subsequently, water and diethyl ether were added to the reaction mixture, and the mixture was separated into two layers. 1 N Aqueous hydrochloric acid solution (25.1 mL) was added to the aqueous layer thus obtained, and the mixture was extracted twice with dichloromethane. The organic layer thus obtained was dried over anhydrous sodium sulfate. The resulting mixture was filtered, and then the solvent was distilled off under reduced pressure to give the title compound (3.02 g).

$^1$H-NMR (400 MHz, CDCl$_3$) δ ppm:
8.26 (1H, s), 8.15-8.11 (1H, m), 8.03-7.95 (2H, m), 3.98 (3H, s).

Reference Example 19 tert-Butyl 4-(4-acetyl-2H-1,2,3-triazol-2-yl)-2-fluorobenzoate

[Chemical Formula 46]

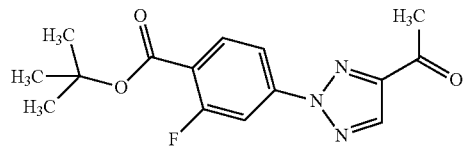

N,N-Dimethylformamide di-tert-butylacetal (16.4 mL, 68.4 mmol) was added to a dichloromethane (60 mL) suspension of the compound obtained in Reference Example 18 (3.01 g) at room temperature. The mixture was stirred at room temperature for 2.5 hours. Subsequently, the solvent in the reaction mixture was distilled off under reduced pressure. The resulting residue was purified by silica gel column chromatography (dichloromethane) to give the title compound (2.64 g, yield: 76%).

$^1$H-NMR (400 MHz, CDCl$_3$) δ ppm:
8.26 (1H, s), 8.06-7.91 (3H, m), 2.71 (3H, s), 1.63 (9H, s).

Reference Example 20 tert-Butyl 2-fluoro-4-[4-(1-hydroxyethyl)-2H-1,2,3-triazol-2-yl]benzoate

[Chemical Formula 47]

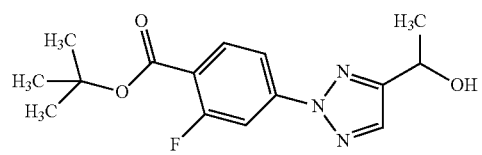

Sodium borohydride (0.756 g, 19.0 mmol) was added to a methanol (52 mL) and tetrahydrofuran (52 mL) solution of the compound obtained in Reference Example 19 (2.63 g, 8.63 mmol) under ice cooling. The mixture was stirred at the same temperature for 1 hour. Subsequently, water was added to the reaction mixture, and the resulting mixture was extracted with ethyl acetate. The organic layer thus obtained was dried over anhydrous sodium sulfate. The resulting mixture was filtered, then the solvent was distilled off under reduced pressure, and the resulting residue was purified by silica gel column chromatography (30% ethyl acetate/hexane) to give the title compound (1.59 g, yield: 60%).

$^1$H-NMR (400 MHz, CDCl$_3$) δ ppm:
8.01-7.97 (1H, m), 7.89-7.81 (3H, m), 5.18-5.12 (1H, m), 1.65 (3H, d, J=6 Hz), 1.62 (9H, s).

Reference Example 21 tert-Butyl 2-fluoro-4-{4-[(1S)-1-hydroxyethyl]-2H-1,2,3-triazol-2-yl}benzoate

[Chemical Formula 48]

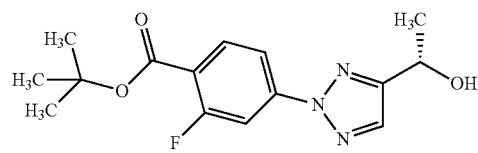

Lipase (acrylic resin support, from *Candida antarctica*) (0.195 g), and vinyl acetate (0.618 mL, 6.68 mmol) were added to a toluene (24 mL) solution of the compound obtained in Reference Example 20 (1.58 g) at room temperature. The mixture was stirred at room temperature for 42 hours. Subsequently, the solid in the reaction mixture was filtered. The solvent in the filtrate thus obtained was distilled off under reduced pressure. The resulting residue was purified by silica gel column chromatography (20%-28% ethyl acetate/hexane) to give the title compound (0.710 g, yield: 45%).

$^1$H-NMR (400 MHz, CDCl$_3$) δ ppm:
$^1$H-NMR (CDCl$_3$) δ: 8.01-7.97 (1H, m), 7.89-7.81 (3H, m), 5.18-5.12 (1H, m), 1.65 (4H, d, J=6.4 Hz), 1.62 (9H, s).

Reference Example 22

5-(Methoxymethoxy)pyridin-2-carbonitrile

[Chemical Formula 49]

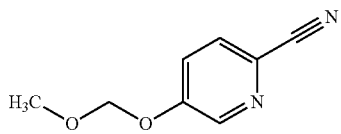

60% sodium hydride (3.62 g, 90.4 mmol) was added to an N,N-dimethylformamide (70 mL) solution of 5-hydroxypyridin-2-carbonitrile (7.24 g, 60.3 mmol) at 0° C., and the mixture was stirred at the same temperature for 15 minutes. Subsequently, chloromethyl methyl ether (9.16 ml, 121 mmol) was added to the mixture little by little, and the resulting mixture was further stirred at the same temperature for 45 minutes. A saturated aqueous solution of ammonium chloride and water were added to the reaction mixture, and the mixture was extracted twice with ethyl acetate. The organic layer thus obtained was washed with brine, and then dried over anhydrous sodium sulfate. The solvent was distilled off under reduced pressure, and the resulting residue was purified by silica gel column chromatography (hexane:ethyl acetate=75:25, v/v) to give the title compound (8.63 g, yield: 87%).

$^1$H-NMR (400 MHz, CDCl$_3$) δ ppm:
8.46 (1H, dd, J=3, 1 Hz), 7.65 (1H, dd, J=9, 1 Hz), 7.45 (1H, dd, J=9, 3 Hz), 5.28 (2H, s), 3.50 (3H, s).

Reference Example 23

Cyclopropyl[5-(methoxymethoxy)pyridin-2-yl]methanone

[Chemical Formula 50]

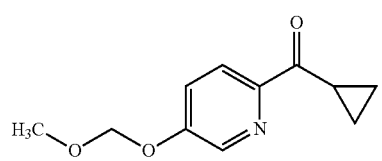

0.7 M Cyclopropylmagnesium bromide-tetrahydrofuran solution (72.9 mL, 51.0 mmol) was added to a tetrahydrofuran (68 mL) solution of the compound obtained in Reference Example 22 (5.58 g, 34.0 mmol) at 0° C. over 20 minutes, and the mixture was stirred at the same temperature for 20 minutes. A saturated aqueous solution of ammonium chloride and water were added to the reaction mixture, and the mixture was extracted twice with ethyl acetate. The organic layer thus obtained was washed with brine, and then dried over anhydrous sodium sulfate. The solvent was distilled off under reduced pressure to give the crude title compound (11.5 g).

Reference Example 24

Cyclopropyl(5-hydroxypyridin-2-yl)methanone

[Chemical Formula 51]

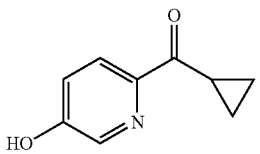

1 M Sulfuric acid (20 mL) was added to a tetrahydrofuran (20 mL) solution of the crude compound obtained in Reference Example 23 (5.72 g) at room temperature, and the mixture was stirred at 60° C. for 2.5 hours. The reaction mixture was cooled to room temperature, and then 5 M aqueous sodium hydroxide solution was added to the reaction mixture to adjust the pH to 6. Subsequently, the resulting mixture was extracted twice with ethyl acetate. The organic layer thus obtained was washed with brine, and then dried over anhydrous sodium sulfate. The solvent was distilled off under reduced pressure, and the resulting residue was purified by silica gel column chromatography (hexane:ethyl acetate=80:20→50:50, v/v) to give the title compound (2.77 g, yield: 52%).

$^1$H-NMR (400 MHz, CDCl$_3$) δ ppm:
8.32 (1H, dd, J=3, 1 Hz), 8.00 (1H, d, J=9, 1 Hz), 7.27 (1H, dd, J=9, 3 Hz), 3.43-3.35 (1H, m), 1.26-1.21 (2H, m), 1.12-1.06 (2H, m).

Reference Example 25 tert-Butyl 4-{4-[(1R)-1-{[6-(cyclopropylcarbonyl)pyridin-3-yl]oxy}ethyl]-2H-1,2,3-triazol-2-yl}-2-fluorobenzoate

[Chemical Formula 52]

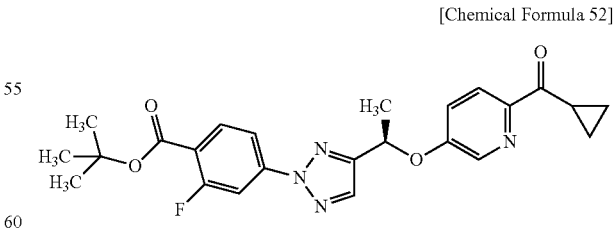

Di-tert-butyl azodicarboxylate (0.583 g, 2.53 mmol) was added to a tetrahydrofuran (14 mL) solution of the compound obtained in Reference Example 21 (0.707 g, 2.30 mmol), the compound obtained in Reference Example 24 (0.413 g, 2.53 mmol), and triphenylphosphine (0.664 g, 2.53 mmol) at room temperature. The mixture was stirred at room temperature for 18 hours. Subsequently, the solvent in the reaction mixture was distilled off under reduced pressure. The resulting residue was purified by silica gel column chromatography (20% ethyl acetate/hexane) to give the title compound (1.08 g, quantitative).

$^1$H-NMR (400 MHz, CDCl$_3$) δ ppm:
8.42 (1H, d, J=3 Hz), 8.02-7.98 (2H, m), 7.89-7.81 (3H, m), 7.37-7.34 (1H, m), 5.81-5.76 (1H, m), 3.45-3.38 (1H, m), 1.84 (3H, d, J=7 Hz), 1.62 (9H, s), 1.22-1.18 (2H, m), 1.08-1.03 (2H, m).

Reference Example 26

4-{4-[(1R)-1-{[6-(Cyclopropylcarbonyl)pyridin-3-yl]oxy}ethyl]-2H-1,2,3-triazol-2-yl}-2-fluorobenzoic acid

[Chemical Formula 53]

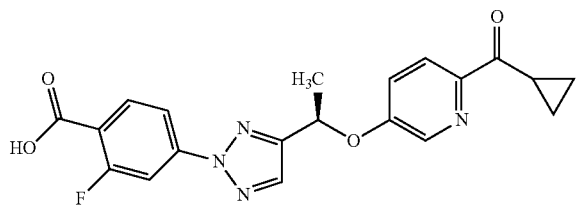

Trifluoroacetic acid (10.7 mL) was added to a dichloromethane (21.4 mL) solution of the compound obtained in Reference Example 25 (0.108 g) at room temperature. The mixture was stirred at room temperature for 1 hour. Subsequently, the solvent in the reaction mixture was distilled off under reduced pressure. A small amount of a saturated aqueous solution of sodium hydrogen carbonate was added to the resulting residue, then a 10% aqueous citric acid solution was added to the mixture, and the mixture was extracted twice with dichloromethane. The organic layer thus obtained was dried over anhydrous sodium sulfate. The resulting mixture was filtered, and then the solvent was distilled off under reduced pressure to give the title compound (0.879 g, yield: 93%).

$^1$H-NMR (400 MHz, CDCl$_3$) δ ppm:
8.45 (1H, d, J=3 Hz), 8.18-8.14 (1H, m), 8.01 (1H, d, J=9 Hz), 7.97-7.89 (2H, m), 7.85 (1H, s), 7.38-7.35 (1H, m), 5.83-5.78 (1H, m), 3.43-3.37 (1H, m), 1.85 (3H, d, J=6 Hz), 1.22-1.19 (2H, m), 1.09-1.04 (2H, m).

Reference Example 27

(4-{1-[2-(4-Amino-3-fluorophenyl)-2H-1,2,3-triazol-4-yl]propoxy}phenyl)(cyclopropyl)methanone

[Chemical Formula 54]

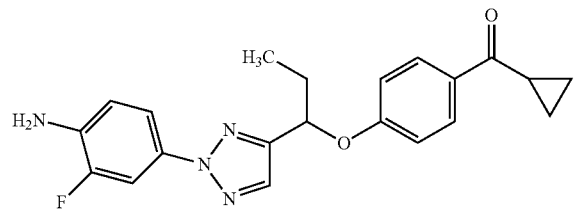

Diphenylphosphoryl azide (0.395 mL, 1.83 mmol) was added to a tert-butanol (10 mL) solution of the compound obtained in Reference Example 7 (0.500 g, 1.22 mmol) and triethylamine (0.340 mL, 2.44 mmol) at room temperature. The mixture was stirred at 90° C. for 3.5 hours, and then returned to room temperature. The solvent in the reaction mixture was distilled off under reduced pressure, and the resulting residue was purified by silica gel column chromatography (20% ethyl acetate/hexane) to give a mixture (0.616 g) containing tert-butyl[4-(4-{1-[4-(cyclopropylcarbonyl)phenoxy]propyl}-2H-1,2,3-triazol-2-yl)-2-fluorophenyl]carbamate.

Trifluoroacetic acid (6 mL) was added to a dichloromethane (12 mL) solution of the mixture (0.610 g) described above at room temperature. The mixture was stirred at room temperature for 2 hours. Subsequently, the solvent in the reaction mixture was distilled off under reduced pressure. A saturated aqueous solution of sodium hydrogen carbonate and water were added to the resulting residue, and the mixture was extracted with dichloromethane. The organic layer thus obtained was dried over anhydrous sodium sulfate. The resulting mixture was filtered, then the solvent was distilled off under reduced pressure, and the resulting residue was purified by silica gel column chromatography (25% ethyl acetate/hexane) to give the title compound (242 mg, yield: 52%).

$^1$H-NMR (400 MHz, CDCl$_3$) δ ppm:
7.97-7.93 (2H, m), 7.72-7.69 (1H, m), 7.64-7.61 (2H, m), 7.03-6.99 (2H, m), 6.86-6.82 (1H, m), 5.49-5.45 (1H, m), 3.85 (2H, br s), 2.62-2.56 (1H, m), 2.20-2.04 (2H, m), 1.20-1.16 (2H, m), 1.09-1.05 (3H, m), 1.00-0.95 (2H, m).

Reference Example 28

(5-{(1R)-1-[2-(4-Amino-3-fluorophenyl)-2H-1,2,3-triazol-4-yl]ethoxy}pyridin-2-yl)(cyclopropyl)methanone

[Chemical Formula 55]

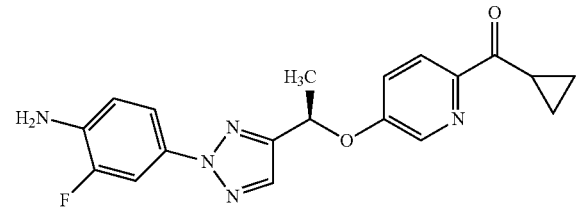

Diphenylphosphoryl azide (0.169 mL, 0.783 mmol) was added to a tert-butanol (5 mL) solution of the compound obtained in Reference Example 26 (0.207 g, 0.522 mmol) and triethylamine (0.146 mL, 1.04 mmol) at room temperature. The mixture was stirred at 90° C. for 2.5 hours, and then returned to room temperature. The solvent in the reaction mixture was distilled off under reduced pressure, and the resulting residue was purified by silica gel column chromatography (15% ethyl acetate/hexane) to give a mixture (0.287 g) containing tert-butyl (4-{4-[(1R)-1-{[6-(cyclopropylcarbonyl)pyridin-3-yl]oxy}ethyl]-2H-1,2,3-triazol-2-yl}-2-fluorophenyl)carbamate.

Trifluoroacetic acid (3 mL) was added to a dichloromethane (6 mL) solution of the mixture (0.282 g) described above at room temperature. The mixture was stirred at room temperature for 1 hour. Subsequently, the solvent in the reaction mixture was distilled off under reduced pressure. A saturated aqueous solution of sodium hydrogen carbonate and water were added to the resulting residue, and the mixture was extracted with dichloromethane. The organic layer thus obtained was dried over anhydrous sodium sulfate. The resulting mixture was filtered, then the solvent was distilled off under reduced pressure, and the resulting residue was purified by silica gel column chromatography (30% ethyl acetate/hexane) to give the title compound (190 mg, yield: 99%).

¹H-NMR (400 MHz, CDCl₃) δ ppm:
8.42 (1H, d, J=3 Hz), 8.00-7.98 (1H, m), 7.72-7.68 (2H, m), 7.64-7.61 (1H, m), 7.39-7.36 (1H, m), 6.87-6.83 (1H, m), 5.78-5.73 (1H, m), 3.44-3.37 (1H, m), 1.82 (3H, d, J=6 Hz), 1.21-1.18 (2H, m), 1.08-1.03 (2H, m).

Reference Example 29

Ethyl 2-[3-fluoro-4-(methoxycarbonyl)phenyl]-2H-tetrazol-5-carboxylate

[Chemical Formula 56]

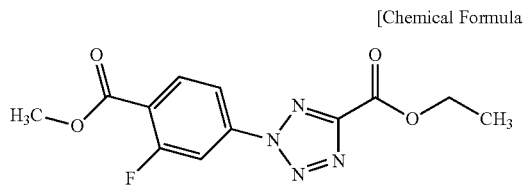

Benzene sulfonyl hydrazide (2.55 g, 14.8 mmol) was added to an ethanol (86 mL) solution of ethyl glyoxalate (50% toluene solution, 4.53 g, 22.2 mmol) at room temperature. The mixture was stirred at room temperature for 45 minutes. Subsequently, the solvent in the reaction mixture was distilled off under reduced pressure. The resulting residue was diluted with pyridine (86 mL). This mixture was designated reaction mixture A. On the other hand, methyl 4-amino-2-fluorobenzoate (Bioorg. Med. Chem. 2009, 17, 7042-7051.) (2.50 g, 14.8 mmol) was suspended in a 4 N aqueous hydrochloric acid solution (18 mL), and an aqueous (4 mL) solution of sodium nitrite (1.12 g, 16.3 mmol) was added dropwise to the resulting suspension under ice cooling. The mixture was stirred at the same temperature for 15 minutes, and then the obtained reaction mixture was added dropwise to the reaction mixture A under ice cooling. The mixture was stirred at the same temperature for 4 hours. Subsequently, water was added to the reaction mixture, and the resulting mixture was extracted with ethyl acetate. The organic layer thus obtained was dried over anhydrous sodium sulfate. The resulting mixture was filtered, then the solvent was distilled off under reduced pressure, and the resulting residue was purified by silica gel column chromatography (dichloromethane) to give the title compound (2.01 g, yield: 46%).
¹H-NMR (400 MHz, CDCl₃) δ ppm:
8.22-8.18 (1H, m), 8.13-8.06 (2H, m), 4.62-4.57 (2H, m), 3.99 (3H, s), 1.52-1.49 (3H, m).

Reference Example 30

2-[3-Fluoro-4-(methoxycarbonyl)phenyl]-2H-tetrazol-5-carboxylic acid

[Chemical Formula 57]

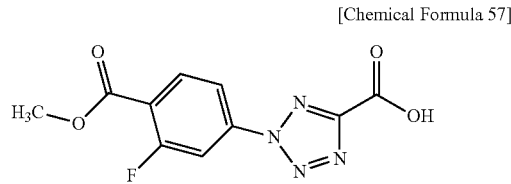

An aqueous (20 mL) solution of lithium hydroxide monohydrate (0.314 g, 7.48 mmol) was added to a mixed solution containing tetrahydrofuran (40 mL) and the compound obtained in Reference Example 29 (2.00 g, 6.80 mmol) under ice cooling. The mixture was stirred at the same temperature for 18 hours. Subsequently, water and diethyl ether were added to the reaction mixture, and the mixture was separated into two layers. 1 N Aqueous hydrochloric acid solution (7.48 mL) was added to the aqueous layer thus obtained, and the mixture was extracted four times with dichloromethane. The organic layer thus obtained was dried over anhydrous sodium sulfate. The resulting mixture was filtered, and then the solvent was distilled off under reduced pressure to give the title compound (1.32 g, yield: 73%).
¹H-NMR (400 MHz, DMSO-d₆) δ ppm:
8.23-8.10 (3H, m), 3.92 (3H, s).

Reference Example 31

Methyl 2-fluoro-4-{5-[methoxy(methyl)carbamoyl]-2H-tetrazol-2-yl}benzoate

[Chemical Formula 58]

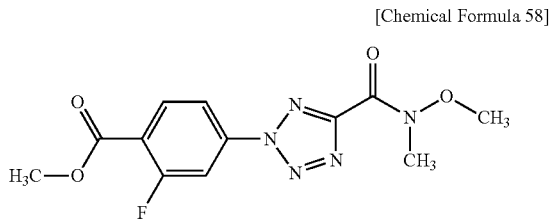

Triethylamine (1.63 mL, 11.7 mmol) was added to a dichloromethane (26 mL) suspension of the compound obtained in Reference Example 30 (1.30 g, 4.88 mmol), N,O-dimethylhydroxylamine hydrochloride (0.572 g, 5.86 mmol), N-(3-dimethylaminopropyl)-N'-ethylcarbodiimide hydrochloride (1.12 g, 5.86 mmol), and 1-hydroxybenzotriazole monohydrate (0.897 g, 5.86 mmol). The mixture was stirred at room temperature for 58 hours. Subsequently, water was added to the reaction mixture, and the resulting mixture was extracted with dichloromethane. The organic layer thus obtained was dried over anhydrous sodium sulfate. The resulting mixture was filtered, then the solvent was distilled off under reduced pressure, and the resulting residue was purified by silica gel column chromatography (10% ethyl acetate/dichloromethane) to give the title compound (1.18 g, yield: 78%).
¹H-NMR (400 MHz, CDCl₃) δ ppm:
8.21-8.18 (1H, m), 8.11-8.02 (2H, m), 3.99 (3H, s), 3.93 (3H, s), 3.46 (3H, br s).

Reference Example 32

Methyl 2-fluoro-4-(5-propionyl-2H-tetrazol-2-yl)benzoate

[Chemical Formula 59]

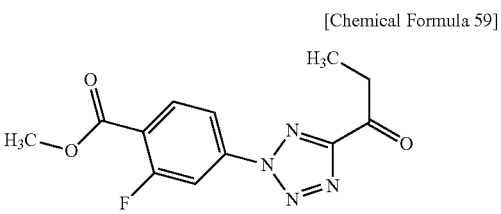 [SMILES: CCC(=O)c1nnn(-c2ccc(C(=O)OC)c(F)c2)n1]

Ethylmagnesium chloride (as an activator, 10 mol % zinc chloride is contained, 1.0 mol/L tetrahydrofuran solution, 2.52 mL, 2.52 mmol) was added dropwise to a tetrahydrofuran (12 mL) solution of the compound obtained in Reference Example 31 (0.600 g, 1.94 mmol) under ice cooling. The mixture was stirred at the same temperature for 200 minutes, and then ethylmagnesium chloride (the same as the above, 2.52 mL, 2.52 mmol) was further added. The mixture was stirred at the same temperature for 1 hour. Subsequently, water was added to the reaction mixture, and the resulting mixture was extracted with ethyl acetate. The organic layer thus obtained was dried over anhydrous sodium sulfate. The resulting mixture was filtered, then the solvent was distilled off under reduced pressure, and the resulting residue was purified by silica gel column chromatography (dichloromethane) to give the title compound (0.420 g, yield: 78%).

$^1$H-NMR (400 MHz, CDCl$_3$) δ ppm:
8.22-8.18 (1H, m), 8.13-8.06 (2H, m), 4.00 (3H, s), 3.30-3.25 (2H, m), 1.34-1.31 (3H, m).

Reference Example 33

Methyl 2-fluoro-4-[5-(1-hydroxypropyl)-2H-tetrazol-2-yl]benzoate

[Chemical Formula 60]

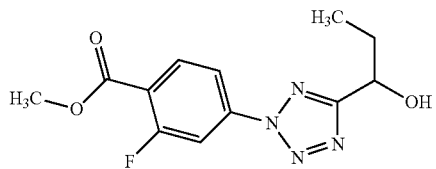

Sodium borohydride (0.756 g, 19.0 mmol) was added to a methanol (8.5 mL) suspension of the compound obtained in Reference Example 32 (0.419 g, 1.51 mmol) under ice cooling. The mixture was stirred at the same temperature for 2 hours. Subsequently, water was added to the reaction mixture, and the resulting mixture was extracted with ethyl acetate. The organic layer thus obtained was dried over anhydrous sodium sulfate. The resulting mixture was filtered, then the solvent was distilled off under reduced pressure, and the resulting residue was purified by silica gel column chromatography (10% ethyl acetate/dichloromethane) to give the title compound (0.340 g, yield: 81%).

$^1$H-NMR (400 MHz, CDCl$_3$) δ ppm:
8.18-8.14 (1H, m), 8.05-7.97 (2H, m), 5.11-5.06 (1H, m), 3.99 (3H, s), 2.65-2.63 (1H, m), 2.18-1.99 (2H, m), 1.08-1.05 (3H, m).

Reference Example 34

Methyl 4-(5-{1-[4-(cyclopropylcarbonyl)phenoxy]propyl}-2H-tetrazol-2-yl)-2-fluorobenzoate

[Chemical Formula 61]

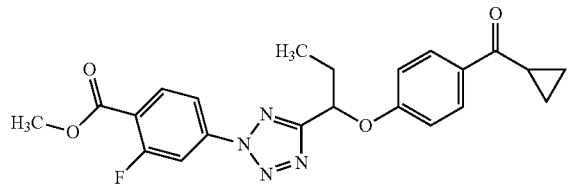

Di-tert-butyl azodicarboxylate (0.298 g, 1.30 mmol) was added to a tetrahydrofuran (7 mL) solution of the compound obtained in Reference Example 33 (0.330 g, 1.18 mmol), cyclopropyl(4-hydroxyphenyl)methanone (0.210 g, 1.30 mmol), and triphenylphosphine (0.340 g, 1.30 mmol) at room temperature. The mixture was stirred at room temperature for 21 hours. Subsequently, the solvent in the reaction mixture was distilled off under reduced pressure. The resulting residue was purified by silica gel column chromatography (23% ethyl acetate/hexane) to give the title compound (0.414 g, yield: 83%).

$^1$H-NMR (400 MHz, CDCl$_3$) δ ppm:
8.17-8.13 (1H, m), 8.03-7.95 (4H, m), 7.08-7.05 (2H, m), 5.67-5.64 (1H, m), 3.98 (3H, s), 2.62-2.56 (1H, m), 2.38-2.21 (2H, m), 1.20-1.16 (2H, m), 1.13-1.09 (3H, m), 1.00-0.97 (2H, m).

Reference Example 35

4-(5-{1-[4-(Cyclopropylcarbonyl)phenoxy]propyl}-2H-tetrazol-2-yl)-2-fluorobenzoic acid

[Chemical Formula 62]

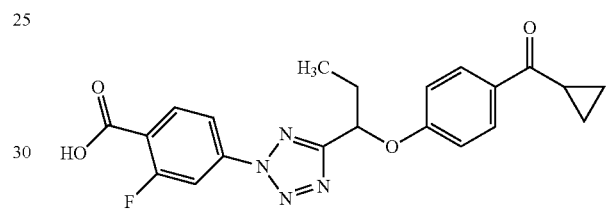

1 N Aqueous sodium hydroxide solution (2.13 mL) was added to a tetrahydrofuran (8.2 mL) solution of the compound obtained in Reference Example 34 (0.410 g, 0.966 mmol) at room temperature. The mixture was stirred at 60° C. for 3 hours, and then returned to room temperature. Subsequently, water and diethyl ether were added to the reaction mixture, and the mixture was separated into two layers. 1 N Aqueous hydrochloric acid solution (2.13 mL) was added to the aqueous layer thus obtained, and the mixture was extracted twice with dichloromethane. The organic layer thus obtained was dried over anhydrous sodium sulfate. The resulting mixture was filtered, and then the solvent was distilled off under reduced pressure to give the title compound (0.396 g, yield: 100%).

$^1$H-NMR (400 MHz, CDCl$_3$) δ ppm:
8.25-8.21 (1H, m), 8.06-7.96 (4H, m), 7.08-7.06 (2H, m), 5.68-5.65 (1H, m), 2.62-2.56 (1H, m), 2.39-2.22 (2H, m), 1.21-1.17 (2H, m), 1.13-1.10 (3H, m), 1.00-0.97 (2H, m).

Reference Example 36

Methyl 4-(5-acetyl-2H-tetrazol-2-yl)-2-fluorobenzoate

[Chemical Formula 63]

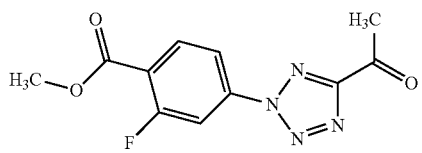

Methylmagnesium bromide (0.99 mol/L tetrahydrofuran solution, 3.00 mL, 2.97 mmol) was added dropwise to a tetrahydrofuran (11.5 mL) solution of the compound obtained in Reference Example 31 (0.575 g, 1.86 mmol) under ice cooling. The mixture was stirred at the same temperature for 45 minutes. Subsequently, water was added to the reaction mixture, and the resulting mixture was extracted with ethyl acetate. The organic layer thus obtained was dried over anhydrous sodium sulfate. The resulting mixture was filtered, then the solvent was distilled off under reduced pressure, and the resulting residue was purified by silica gel column chromatography (dichloromethane) to give the title compound (0.295 g, yield: 60%).

$^1$H-NMR (400 MHz, CDCl$_3$) δ ppm:
8.23-8.06 (3H, m), 4.00 (3H, s), 2.86 (3H, s).

Reference Example 37

Methyl 2-fluoro-4-[5-(1-hydroxyethyl)-2H-tetrazol-2-yl]benzoate

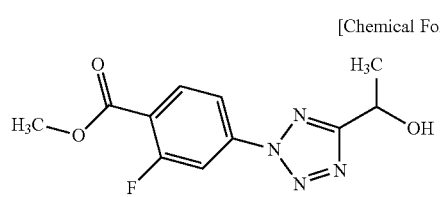

[Chemical Formula 64]

Sodium borohydride (97.5 mg, 2.45 mmol) was added to a mixed methanol (4.4 mL) and tetrahydrofuran (4.4 mL) suspension of the compound obtained in Reference Example 36 (0.294 g, 1.11 mmol) under ice cooling. The mixture was stirred at the same temperature for 30 minutes. Subsequently, water was added to the reaction mixture, and the resulting mixture was extracted with ethyl acetate. The organic layer thus obtained was dried over anhydrous sodium sulfate. The resulting mixture was filtered, then the solvent was distilled off under reduced pressure, and the resulting residue was purified by silica gel column chromatography (12% ethyl acetate/dichloromethane) to give the title compound (0.258 g, yield: 87%).

$^1$H-NMR (400 MHz, CDCl$_3$) δ ppm:
8.19-8.15 (1H, m), 8.05-7.97 (2H, m), 5.34-5.28 (1H, m), 3.99 (3H, s), 1.76 (3H, d, J=7 Hz).

Reference Example 38

Methyl 4-[5-(1-{[6-(cyclopropylcarbonyl)pyridin-3-yl]oxy}ethyl)-2H-tetrazol-2-yl]-2-fluorobenzoate

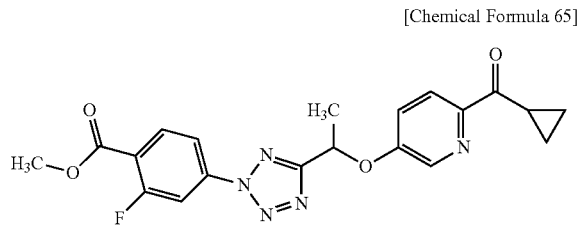 [SMILES: COC(=O)c1ccc(-n2nnc(C(C)Oc3ccc(C(=O)C4CC4)nc3)n2)cc1F]

[Chemical Formula 65]

Di-tert-butyl azodicarboxylate (0.276 g, 1.05 mmol) was added to a tetrahydrofuran (7 mL) solution of the compound obtained in Reference Example 37 (0.255 g, 0.958 mmol), the compound obtained in Reference Example 24 (0.172 g, 1.05 mmol), and triphenylphosphine (0.340 g, 1.30 mmol) at room temperature. The mixture was stirred at room temperature for 18 hours. Subsequently, the solvent in the reaction mixture was distilled off under reduced pressure. The resulting residue was purified by silica gel column chromatography (20% ethyl acetate/hexane) to give the title compound (0.345 g, yield: 88%).

$^1$H-NMR (400 MHz, CDCl$_3$) δ ppm:
8.47-8.46 (1H, m), 8.18-8.14 (1H, m), 8.03-7.95 (3H, m), 7.45-7.42 (1H, m), 5.96-5.91 (1H, m), 3.98 (3H, s), 3.45-3.38 (1H, m), 1.97 (3H, d, J=7 Hz), 1.21-1.18 (2H, m), 1.08-1.03 (2H, m).

Reference Example 39

4-[5-(1-{[6-(Cyclopropylcarbonyl)pyridin-3-yl]oxy}ethyl)-2H-tetrazol-2-yl]-2-fluorobenzoic acid

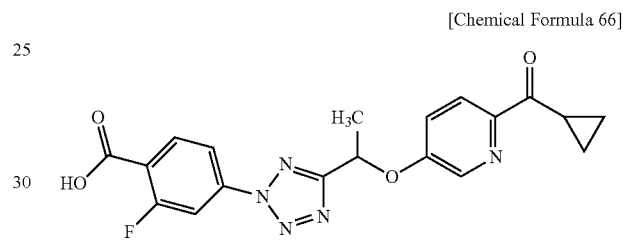

[Chemical Formula 66]

1 N Aqueous sodium hydroxide solution (1.80 mL) was added to a tetrahydrofuran (6.7 mL) solution of the compound obtained in Reference Example 38 (0.337 g, 0.819 mmol) at room temperature. The mixture was stirred at 60° C. for 75 minutes and then returned to room temperature. Subsequently, water and diethyl ether were added to the reaction mixture, and the mixture was separated into two layers. 1 N Aqueous hydrochloric acid solution (1.80 mL) was added to the aqueous layer thus obtained, and the mixture was extracted twice with dichloromethane. The organic layer thus obtained was dried over anhydrous sodium sulfate. The resulting mixture was filtered, and then the solvent was distilled off under reduced pressure to give the title compound (0.283 g, yield: 87%).

$^1$H-NMR (400 MHz, CDCl$_3$) δ ppm:
8.49 (1H, d, J=3 Hz), 8.24-8.20 (1H, m), 8.06-7.98 (3H, m), 7.45 (1H, dd, J=9, 3 Hz), 5.97-5.92 (1H, m), 3.42-3.36 (1H, m), 1.98 (3H, d, J=7 Hz), 1.23-1.19 (2H, m), 1.09-1.04 (2H, m).

Reference Example 40

Methyl 4-(aminocarbonothioyl)-2-fluorobenzoate

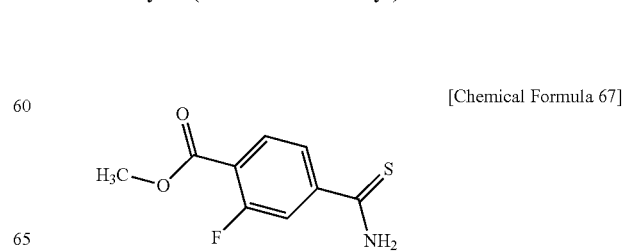

[Chemical Formula 67]

A sodium hydrogensulfide hydrate (9.22 g, 0.165 mol) was added to an N,N-dimethylformamide (74 mL) suspension of methyl 4-cyano-2-fluorobenzoate (WO 2010/115751) (7.37 g, 41.1 mmol) and magnesium chloride hexahydrate (10.0 g, 49.4 mmol) at room temperature. The mixture was stirred at room temperature for 4 hours. Subsequently, water (148 mL) was added to the reaction mixture, and the precipitated solid was filtered. The solid thus obtained was added to 1 N aqueous hydrochloric acid solution (148 mL), and the mixture was stirred for 20 minutes. The solid in the reaction mixture was filtered to give the title compound (7.63 g, yield: 87%).

$^1$H-NMR (500 MHz, DMSO-$d_6$) δ ppm:
10.21 (1H, s), 9.75 (1H, s), 7.94-7.90 (1H, m), 7.79-7.72 (2H, m), 3.88-3.87 (3H, m).

Reference Example 41

Methyl 2-fluoro-4-(5-formyl-1,3-thiazol-2-yl)benzoate

[Chemical Formula 68]

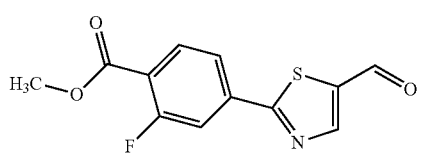

2-Bromomalonaldehyde (5.31 g, 35.2 mmol) was added to a tetrahydrofuran (100 mL) suspension of the compound obtained in Reference Example 40 (5.00 g, 23.5 mmol) and sodium hydrogen carbonate (5.91 g, 70.4 mmol) at room temperature. The mixture was stirred at 60° C. for 5 hours, and then air-cooled. Subsequently, water (1 L) was added to the reaction mixture, and the precipitated solid was filtered. The solid thus obtained was diluted with dichloromethane (300 mL), and stirred. Subsequently, the solid in the reaction mixture was filtered. The solvent in the filtrate thus obtained was distilled off under reduced pressure, and the resulting residue was diluted with ethyl acetate (150 mL). The mixture was stirred under reflux, then cooled on ice, and the precipitated solid was filtered to give the title compound (4.08 g, yield: 66%).

$^1$H-NMR (500 MHz, DMSO-$d_6$) δ ppm:
10.12 (1H, m), 8.86-8.85 (1H, m), 8.05-8.02 (3H, m), 3.90-3.89 (3H, m).

Reference Example 42

Methyl 2-fluoro-4-[5-(1-hydroxyethyl)-1,3-thiazol-2-yl]benzoate

[Chemical Formula 69]

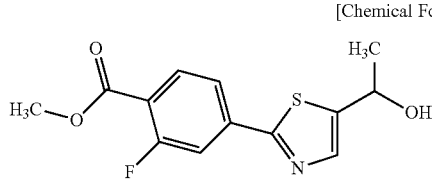

Methylmagnesium bromide (1.12 mol/L tetrahydrofuran solution, 8.75 mL, 9.80 mmol) was added dropwise to a tetrahydrofuran (40 mL) suspension of the compound obtained in Reference Example 41 (2.00 g, 7.54 mmol) under ice cooling. The mixture was stirred at the same temperature for 2 hours. Subsequently, a saturated aqueous solution of ammonium chloride was added to the mixture to quench the reaction. Water was added to the reaction mixture, and the resulting mixture was extracted with ethyl acetate. The organic layer thus obtained was dried over anhydrous sodium sulfate. The resulting mixture was filtered, then the solvent was distilled off under reduced pressure, and the resulting residue was purified by silica gel column chromatography (50% ethyl acetate/hexane) to give the title compound (1.75 g, yield: 83%).

$^1$H-NMR (500 MHz, CDCl$_3$) δ ppm:
8.01-7.98 (1H, m), 7.73-7.71 (3H, m), 5.25-5.20 (1H, m), 3.96-3.95 (3H, m), 2.34-2.32 (1H, m), 1.67-1.65 (3H, m).

Reference Example 43

Methyl 4-(5-{1-[4-(cyclopropylcarbonyl)phenoxy]ethyl}-1,3-thiazol-2-yl)-2-fluorobenzoate

[Chemical Formula 70]

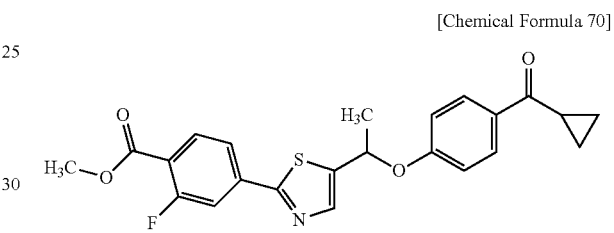

Di-tert-butyl azodicarboxylate (0.783 g, 3.40 mmol) was added to a tetrahydrofuran (17 mL) solution of the compound obtained in Reference Example 42 (0.870 g, 3.09 mmol), cyclopropyl(4-hydroxyphenyl)methanone (0.552 g, 3.40 mmol), and triphenylphosphine (0.892 g, 3.40 mmol) at room temperature. The mixture was stirred at room temperature for 4 hours. Subsequently, the solvent in the reaction mixture was distilled off under reduced pressure. The resulting residue was purified by silica gel column chromatography (33%-43% ethyl acetate/hexane) to give the title compound (0.464 g, yield: 35%).

$^1$H-NMR (500 MHz, CDCl$_3$) δ ppm:
8.01-7.96 (3H, m), 7.82 (1H, m), 7.72-7.71 (1H, m), 7.70-7.69 (1H, m), 7.02-6.98 (2H, m), 5.81-5.77 (1H, m), 3.95 (3H, s), 2.63-2.57 (1H, m), 1.83 (3H, d, J=6 Hz), 1.21-1.18 (2H, m), 1.02-0.97 (2H, m).

Reference Example 44

4-(5-{1-[4-(Cyclopropylcarbonyl)phenoxy]ethyl}-1,3-thiazol-2-yl)-2-fluorobenzoic acid

[Chemical Formula 71]

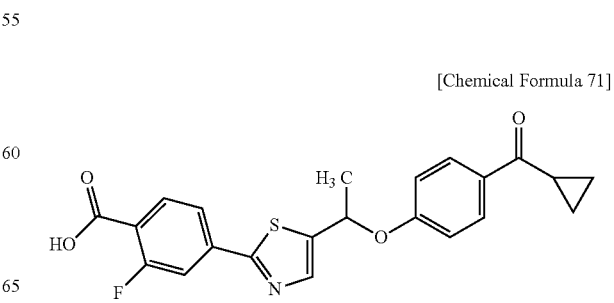

1 N Aqueous sodium hydroxide solution (5.36 mL) was added to a tetrahydrofuran (9.1 mL) solution of the compound obtained in Reference Example 43 (0.456 g, 1.07 mmol) at room temperature. The mixture was stirred at 80° C. for 135 minutes, and then returned to room temperature. Subsequently, water and diethyl ether were added to the reaction mixture, and the mixture was separated into two layers. 1 N Aqueous hydrochloric acid solution (5.36 mL) was added to the aqueous layer thus obtained, and the mixture was extracted with ethyl acetate. The organic layer thus obtained was dried over anhydrous sodium sulfate. The resulting mixture was filtered, then the solvent was distilled off under reduced pressure, and thus the title compound (0.440 g, yield: 100%) was obtained.

$^1$H-NMR (400 MHz, DMSO-$d_6$) δ ppm:
13.44 (1H, br s), 8.10 (1H, s), 8.02-7.93 (3H, m), 7.83-7.79 (2H, m), 7.19-7.15 (2H, m), 6.20-6.15 (1H, m), 2.86-2.80 (1H, m), 1.75-1.74 (3H, m), 0.98-0.96 (4H, m).

Reference Example 45

Methyl 4-[5-(1-{[6-(cyclopropylcarbonyl)pyridin-3-yl]oxy}ethyl)-1,3-thiazol-2-yl]-2-fluorobenzoate

[Chemical Formula 72]

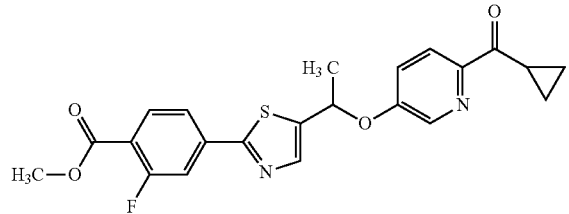

Triphenylphosphine (102 mg, 0.391 mmol) and di-tert-butyl azodicarboxylate (90.0 mg, 0.391 mmol) were added to a tetrahydrofuran (1.8 mL) solution of the compound obtained in Reference Example 42 (100 mg, 0.355 mmol) and the compound obtained in Reference Example 24 (63.8 mg, 0.391 mmol) at room temperature, and the mixture was stirred at the same temperature for 30 minutes. The reaction mixture was concentrated under reduced pressure, and the resulting residue was purified by silica gel column chromatography (hexane:ethyl acetate=90:10→75:25, v/v) to give the title compound (89.6 mg, yield: 59%).

$^1$H-NMR (400 MHz, CDCl$_3$) δ ppm:
8.40 (1H, d, J=3 Hz), 8.03-7.97 (2H, m), 7.84 (1H, s), 7.73-7.69 (2H, m), 7.32 (1H, dd, J=9, 3 Hz), 5.82 (1H, q, J=6 Hz), 3.95 (3H, s), 3.45-3.37 (1H, m), 1.86 (4H, d, J=6 Hz), 1.22-1.17 (2H, m), 1.09-1.03 (2H, m).

Reference Example 46

2-[3-Fluoro-4-(methylthio)phenyl]-1,3-thiazol-5-carbaldehyde

[Chemical Formula 73]

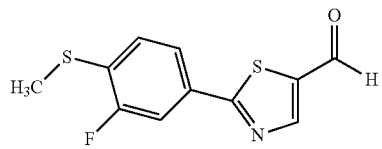

Sodium hydrogen carbonate (2.06 g, 24.6 mmol) and bromomalonaldehyde (1.85 g, 12.3 mmol) were added to a tetrahydrofuran (40 mL) solution of 4-(methylthio)thiobenzamide (1.50 g, 8.18 mmol) at room temperature. The mixture was stirred at 60° C. for 1.5 hours. After the reaction mixture was cooled to room temperature, water was added to the reaction mixture, and the resulting mixture was extracted twice with ethyl acetate. The organic layer thus obtained was washed with brine, and then dried over anhydrous sodium sulfate. The solvent was distilled off under reduced pressure, and the resulting residue was washed with a hexane-ethyl acetate mixture (5:1, v/v) to give the title compound (1.74 g, yield: 90%).

$^1$H-NMR (400 MHz, CDCl$_3$) δ ppm:
10.03 (1H, s), 7.94 (2H, d, J=9 Hz), 7.31 (2H, d, J=9 Hz), 7.26 (1H, s), 2.54 (3H, s).

Reference Example 47

1-{2-[3-Fluoro-4-(methylthio)phenyl]-1,3-thiazol-5-yl}propan-1-ol

[Chemical Formula 74]

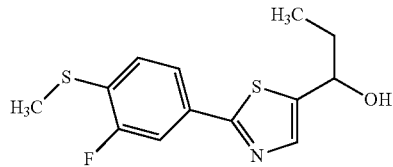

Zinc chloride (403 mg, 2.96 mmol) was added to a tetrahydrofuran (37 mL) solution of the compound obtained in Reference Example 46 (1.74 g, 7.39 mmol) at 0° C., subsequently, 1.00 M ethylmagnesium bromide-tetrahydrofuran solution (8.87 mL, 8.87 mmol) was slowly added, and the mixture was stirred at the same temperature for 30 minutes. Further, 1.00 M ethylmagnesium bromide-tetrahydrofuran solution (8.87 mL, 8.87 mmol) was slowly added to the mixture, and the mixture was stirred at the same temperature for 30 minutes. A saturated aqueous solution of ammonium chloride was added to the reaction mixture, and the mixture was extracted twice with ethyl acetate. The organic layer thus obtained was washed with brine, and then dried over anhydrous sodium sulfate. The solvent was distilled off under reduced pressure, and the resulting residue was washed with diisopropyl ether to give the title compound (1.51 g, yield: 77%).

$^1$H-NMR (500 MHz, CDCl$_3$) δ ppm:
7.83 (2H, d, J=9 Hz), 7.64 (1H, s), 7.28 (2H, d, J=9 Hz), 4.90 (1H, dd, J=7, 6 Hz), 2.52 (3H, s), 2.18 (1H, br s), 1.97-1.84 (2H, m), 1.00 (3H, t, J=7 Hz).

Reference Example 48

N-(4-Bromo-3-fluorobenzoyl)-L-serine methyl ester

[Chemical Formula 75]

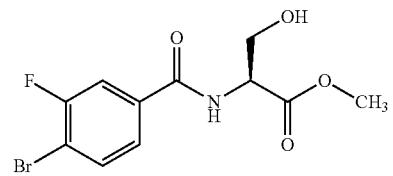

1-Hydroxybenzotriazole monohydrate (839 mg, 5.48 mmol) and N-(3-dimethylaminopropyl)-N'-ethylcarbodiimide hydrochloride (1.05 g, 5.48 mmol) were added to an N,N-dimethylformamide (34 mL) solution of 4-bromo-3-fluorobenzoic acid (1.00 g, 4.57 mmol) at room temperature. The mixture was stirred at the same temperature for 30 minutes, and then L-serine methyl ester hydrochloride (1.42 g, 9.13 mmol) and triethylamine (1.27 mL, 9.13 mmol) were added to the mixture. The resulting mixture was further stirred at the same temperature for 15 minutes. Water was added to the reaction mixture, and the resulting mixture was extracted twice with ethyl acetate. The organic layer thus obtained was washed with a saturated aqueous solution of sodium hydrogen carbonate and brine, and then dried over anhydrous sodium sulfate. The solvent was distilled off under reduced pressure to give the crude title compound (1.63 g).

Reference Example 49

Methyl (4S)-2-(4-bromo-3-fluorophenyl)-4,5-dihydro-1,3-oxazol-4-carboxylate

[Chemical Formula 76]

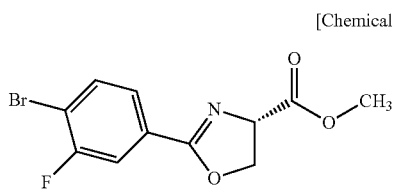

The crude compound obtained in Reference Example 48 (1.00 g) was dissolved in dichloromethane (16 mL), and N,N-diethylaminosulfur trifluoride (614 µL, 4.69 mmol) was added to the mixture at −78° C. The mixture was stirred at the same temperature for 1 hour, and then potassium carbonate (1.30 g, 9.37 mmol) was added to the mixture. The resulting mixture was heated to room temperature over 40 minutes. Water was added to the reaction mixture, and the resulting mixture was extracted twice with dichloromethane. The organic layer thus obtained was dried over anhydrous sodium sulfate. The solvent was distilled off under reduced pressure, and the resulting residue was purified by silica gel column chromatography (hexane:ethyl acetate=80:20→30:70, v/v) to give the title compound (625 mg, yield: 74%).

$^1$H-NMR (500 MHz, CDCl$_3$) δ ppm:
7.73 (1H, dd, J=9, 1 Hz), 7.66 (1H, dd, J=8, 1 Hz), 7.61 (1H, dd, J=8, 6 Hz), 4.95 (1H, dd, J=11, 8 Hz), 4.72 (1H, dd, J=9, 8 Hz), 4.62 (1H, dd, J=11, 9 Hz), 3.83 (3H, s).

Reference Example 50

Methyl 2-(4-bromo-3-fluorophenyl)-1,3-oxazol-4-carboxylate

[Chemical Formula 77]

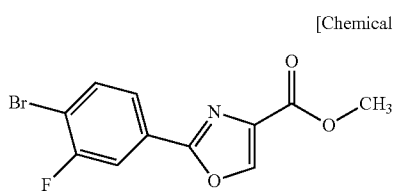

The compound obtained in Reference Example 49 (400 mg, 1.32 mmol) was dissolved in dichloromethane (6.6 mL), and 1,8-diazabicyclo[5.4.0]undec-7-ene (613 µL, 4.10 mmol) and bromotrichloromethane (404 µL, 4.10 mmol) were added to the mixture at room temperature. The mixture was stirred at the same temperature for 30 minutes. Water was added to the reaction mixture, and the resulting mixture was extracted twice with dichloromethane. The organic layer thus obtained was dried over anhydrous sodium sulfate. The solvent was distilled off under reduced pressure, and the resulting residue was purified by silica gel column chromatography (hexane:ethyl acetate=70:30→30:70, v/v) to give the title compound (368 mg, yield: 93%).

$^1$H-NMR (400 MHz, CDCl$_3$) δ ppm:
8.31 (1H, s), 7.87 (1H, dd, J=9, 2 Hz), 7.80 (1H, td, J=8, 2 Hz), 7.68 (1H, dd, J=8, 7 Hz), 3.97 (3H, s).

Reference Example 51

[2-(4-Bromo-3-fluorophenyl)-1,3-oxazol-4-yl]methanol

[Chemical Formula 78]

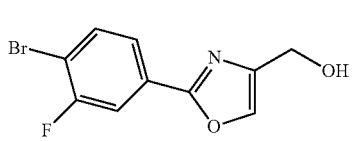

The compound obtained in Reference Example 50 (363 mg, 1.21 mmol) was dissolved in dichloromethane (12 mL), and 1.02 M diisobutylaluminium hydride-hexane solution (1.19 mL, 1.21 mmol) was added to the mixture at −78° C. The mixture was stirred at the same temperature for 30 minutes. Further, 1.02 M diisobutylaluminium hydride-hexane solution (1.19 mL, 1.21 mmol) was added to the mixture, and the resulting mixture was stirred at the same temperature for 1 hour. Subsequently, a saturated aqueous solution of ammonium chloride (600 µL) was added to the mixture at room temperature, and the mixture was stirred at the same temperature for 1 hour. The generated insoluble material was removed by filtration through Celite, then the solvent was distilled off under reduced pressure, and the resulting residue was purified by silica gel column chromatography (hexane:ethyl acetate=75:25→50:50, v/v) to give the title compound (195 mg, yield: 59%).

$^1$H-NMR (500 MHz, CDCl$_3$) δ ppm:
7.78 (1H, dd, J=9, 2 Hz), 7.71 (1H, dd, J=8, 2 Hz), 7.68 (1H, s), 7.65 (1H, dd, J=8, 7 Hz), 4.69 (2H, d, J=6 Hz), 2.06 (1H, br s).

Reference Example 52

1-[2-(4-Bromo-3-fluorophenyl)-1,3-oxazol-4-yl]ethanol

[Chemical Formula 79]

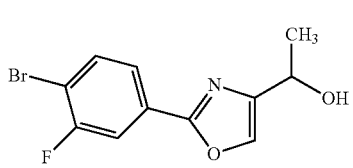

The compound obtained in Reference Example 51 (1.55 g, 5.70 mmol) was dissolved in dichloromethane (15 mL), and Dess-Martin periodinane (3.62 g, 8.55 mmol) was added to the mixture at room temperature. The mixture was stirred at the same temperature for 15 minutes. A saturated aqueous solution of sodium hydrogen carbonate and 1 M aqueous sodium sulfite solution were added to the reaction mixture. The mixture was stirred at room temperature for 5 minutes, and then extracted twice with ethyl acetate. The organic layer thus obtained was washed with a saturated aqueous solution of sodium hydrogen carbonate and brine, and then dried over anhydrous sodium sulfate. The solvent was distilled off under reduced pressure, and the resulting residue (1.61 g) was dissolved in tetrahydrofuran (50 mL). Subsequently, 1.10 M methylmagnesium bromide-tetrahydrofuran solution (5.70 mL, 6.27 mmol) was added to the mixture at 0° C. over 10 minutes, and the mixture was stirred at the same temperature for 30 minutes. 1 M hydrochloric acid was added to the reaction mixture, and the mixture was extracted twice with ethyl acetate. The organic layer thus obtained was washed with brine, and then dried over anhydrous sodium sulfate. The solvent was distilled off under reduced pressure, and the resulting residue was purified by silica gel column chromatography (hexane:ethyl acetate=70:30→50:50, v/v) to give the title compound (1.37 g, yield: 84%).

$^1$H-NMR (500 MHz, CDCl$_3$) δ ppm:
7.78 (1H, dd, J=9, 2 Hz), 7.71 (1H, dd, J=8, 2 Hz), 7.64 (1H, dd, J=8, 7 Hz), 7.61 (1H, s), 4.95-4.88 (1H, m), 2.27 (1H, br s), 1.58 (3H, d, J=6 Hz).

Reference Example 53

Methyl 2-fluoro-4-[4-(1-hydroxymethyl)-1,3-oxazol-2-yl]benzoate

[Chemical Formula 80]

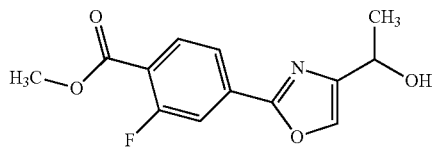

Triethylamine (2.00 mL, 14.4 mmol) and a [1,1'-bis(diphenylphosphino)ferrocene]palladium(II) dichloride-dichloromethane adduct (782 mg, 0.958 mmol) were added to a dimethylformamide (25 mL)-methanol (25 mL) solution of the compound obtained in Reference Example 52 (1.37 g, 4.79 mmol) at room temperature, and the mixture was stirred at 80° C. for 5 hours under carbon monoxide flow. The reaction mixture was cooled to room temperature, then ethyl acetate and water were added to the reaction mixture, and the mixture was vigorously stirred at room temperature. The generated insoluble material was removed by filtration through Celite, and then the mixture was extracted twice with ethyl acetate. The organic layer thus obtained was washed with brine, and then dried over anhydrous sodium sulfate. The solvent was distilled off under reduced pressure, and the resulting residue was purified by silica gel column chromatography (hexane:ethyl acetate=50:50, v/v) to give the title compound (1.06 g, yield: 83%).

$^1$H-NMR (500 MHz, CDCl$_3$) δ ppm:
8.03 (1H, dd, J=8, 7 Hz), 7.87 (1H, dd, J=8, 1 Hz), 7.81 (1H, dd, J=11, 1 Hz), 7.65 (1H, s), 4.97-4.90 (1H, m), 3.96 (3H, s), 2.27 (1H, d, J=5 Hz), 1.59 (3H, d, J=8 Hz).

Reference Example 54

4-(4-{1-[4-(Cyclopropylcarbonyl)phenoxyethyl}-1,3-oxazol-2-yl)-2-fluorobenzoic acid

[Chemical Formula 81]

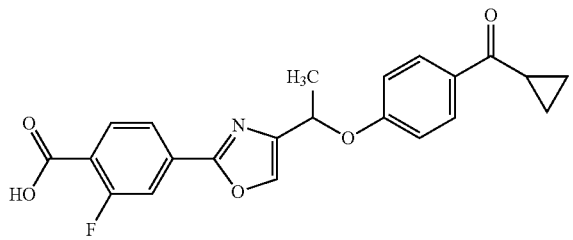

Triphenylphosphine (442 mg, 1.68 mmol) and di-tert-butyl azodicarboxylate (388 mg, 1.68 mmol) were added to a tetrahydrofuran solution (15 mL) of the compound obtained in Reference Example 53 (406 mg, 1.53 mmol) and cyclopropyl (4-hydroxyphenyl)methanone (273 mg, 1.68 mmol) at room temperature. The mixture was stirred at the same temperature for 30 minutes. The solvent was distilled off under reduced pressure, and the resulting residue was purified by silica gel column chromatography (hexane:ethyl acetate=9:1→1:1, v/v). Subsequently, the compound thus obtained was dissolved in tetrahydrofuran (4 mL) and methanol (4 mL), then 2 M aqueous sodium hydroxide solution (0.765 mL, 1.53 mmol) was added to the mixture, and the resulting mixture was stirred at room temperature for 30 minutes. Water and a saturated aqueous solution of ammonium chloride were added to the reaction mixture, and the mixture was extracted three times with ethyl acetate. The extract was dried over anhydrous sodium sulfate. The solvent was distilled off under reduced pressure, and the resulting residue was purified by silica gel column chromatography (hexane:ethyl acetate=4:1→1:4, v/v) to give the title compound (311 mg, yield: 51%).

$^1$H-NMR (400 MHz, CDCl$_3$) δ ppm:
8.18-8.05 (1H, m), 8.00 (2H, d, J=9 Hz), 7.95-7.80 (2H, m), 7.66 (1H, s), 7.02 (2H, d, J=9 Hz), 5.55 (1H, q, J=6 Hz), 2.66-2.57 (1H, m), 1.76 (3H, d, J=7 Hz), 1.23-1.18 (2H, m), 1.03-0.98 (2H, m).

Reference Example 55

4-[4-(1-{[6-(Cyclopropylcarbonyl)pyridin-3-yl]oxy}ethyl)-1,3-oxazol-2-yl]-2-fluorobenzoic acid

[Chemical Formula 82]

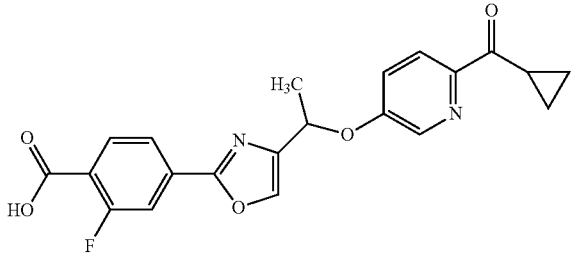

Triphenylphosphine (1.14 g, 4.35 mmol) and di-tert-butyl azodicarboxylate (1.00 g, 4.35 mmol) were added to a tetrahydrofuran (20 mL) solution of the compound obtained in Reference Example 53 (1.05 mg, 3.96 mmol) and the compound obtained in Reference Example 24 (646 mg, 3.96 mmol) at 0° C., and the mixture was stirred at the same temperature for 5 minutes, and then further stirred at room temperature for 30 minutes. The solvent was distilled off under reduced pressure, the resulting residue was purified by silica gel column chromatography (hexane:ethyl acetate=90:10→75:25, v/v) to give a product, and the product (1.16 g) thus obtained was dissolved in tetrahydrofuran (4.0 mL)-methanol (4.0 mL) mixture. Subsequently, 1 M aqueous sodium hydroxide solution (4.0 mL) was added to the resulting mixture at room temperature, and the mixture was stirred at the same temperature for 15 minutes. The reaction mixture was concentrated under reduced pressure, then water was added to the resulting reaction mixture, and the aqueous layer was washed with diethyl ether. 1 M Sulfuric acid was added to the mixture to adjust the pH to 6, and then the resulting mixture was extracted twice with ethyl acetate. The organic layer thus obtained was washed with brine, and then dried over anhydrous sodium sulfate. The solvent was distilled off under reduced pressure, and the resulting residue was washed with a hexane-diisopropyl ether (2:1, v/v) mixture to give the title compound (904 mg, yield: 58%).

$^1$H-NMR (500 MHz, CDCl$_3$) δ ppm:
8.45 (1H, d, J=3 Hz), 8.12 (1H, dd, J=8, 7 Hz), 8.02 (1H, d, J=9 Hz), 7.90 (1H, dd, J=8, 2 Hz), 7.84 (1H, dd, J=11, 2 Hz), 7.71 (1H, d, J=1 Hz), 7.37 (1H, dd, J=9, 3 Hz), 5.58 (1H, q, J=7 Hz), 3.45-3.37 (1H, m), 1.81 (3H, d, J=7 Hz), 1.24-1.19 (2H, m), 1.10-1.04 (2H, m).

Reference Example 56

(4-{1-[2-(4-Amino-3-fluorophenyl)-1,3-oxazol-4-yl]ethoxy}phenyl)(cyclopropyl)methanone

[Chemical Formula 83]

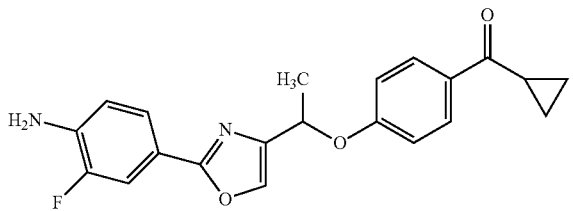

Triethylamine (0.121 mL, 0.865 mmol) and diphenylphosphoryl azide (0.186 mL, 0.865 mmol) were added to a tert-butanol (15 mL) solution of the compound obtained in Reference Example 54 (311 mg, 0.786 mmol) at room temperature, and the mixture was heated at 60° C. for 5 hours. After the reaction mixture was cooled to room temperature, water was added to the reaction mixture, and the resulting mixture was extracted three times with ethyl acetate, and then dried over anhydrous sodium sulfate. The solvent was distilled off under reduced pressure, and the resulting residue was purified by silica gel column chromatography (hexane:ethyl acetate=9:1→1:1, v/v). Subsequently, a methylene chloride (1 mL) solution of trifluoroacetic acid (1 mL) was added to a methylene chloride (2 mL) solution of the compound thus obtained at room temperature, and the resulting mixture was stirred at the same temperature for 30 minutes. The solvent was distilled off under reduced pressure, and the resulting residue was purified by silica gel column chromatography (hexane:ethyl acetate=9:1→1:2, v/v) to give the title compound (123 mg, yield: 44%).

$^1$H-NMR (400 MHz, CDCl$_3$) δ ppm:
7.98 (2H, d, J=9 Hz), 7.67-7.61 (2H, m), 7.51 (1H, s), 7.02 (2H, d, J=7 Hz), 6.81 (1H, dd, J=9, 8 Hz), 5.52 (1H, q, J=6 Hz), 3.27 (2H, bs), 2.64-2.56 (1H, m), 1.74 (3H, d, J=6 Hz), 1.22-1.18 (2H, m), 1.02-0.96 (2H, m).

Reference Example 57

(5-{1-[2-(4-Amino-3-fluorophenyl)-1,3-oxazol-4-yl]ethoxy}pyridin-2-yl)(cyclopropyl)methanone

[Chemical Formula 84]

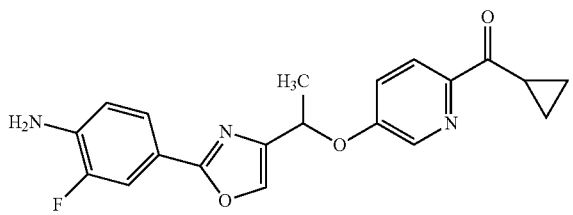

Triethylamine (0.174 mL, 1.25 mmol) and diphenylphosphoryl azide (0.268 mL, 1.25 mmol) were added to a tert-butanol (5 mL) solution of the compound obtained in Reference Example 55 (411 mg, 1.04 mmol) at room temperature, and the mixture was heated at 90° C. for 6 hours. After the reaction mixture was cooled to room temperature, water was added to the reaction mixture, and the resulting mixture was extracted three times with ethyl acetate, and then dried over anhydrous sodium sulfate. The solvent was distilled off under reduced pressure, and the resulting residue was purified by silica gel column chromatography (hexane:ethyl acetate=9:1→1:1, v/v). Subsequently, trifluoroacetic acid (2 mL) was added to a methylene chloride (2 mL) solution of the compound thus obtained at room temperature, and the mixture was stirred at the same temperature for 30 minutes. The solvent was distilled off under reduced pressure, and the resulting residue was purified by silica gel column chromatography (hexane:ethyl acetate=9:1→1:2, v/v) to give the title compound (326 mg, yield: 86%).

$^1$H-NMR (400 MHz, CDCl$_3$) δ ppm:
8.49-8.48 (1H, m), 8.02 (1H, d, J=9 Hz), 7.65-7.60 (2H, m), 7.57 (1H, s), 7.43-7.39 (1H, m), 6.81 (1H, dd, J=9, 9 Hz), 5.57 (1H, q, J=6 Hz), 3.45-3.38 (1H, m), 1.78 (3H, d, J=6 Hz), 1.25-1.20 (2H, m), 1.10-1.06 (2H, m).

Reference Example 58 tert-Butyl 2-fluoro-4-{5-[(1S)-1-hydroxyethyl]-1,2,4-oxadiazol-3-yl}benzoate

[Chemical Formula 85]

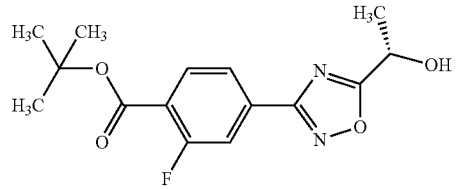

1-Hydroxybenzotriazole monohydrate (16.7 g, 109 mmol) and N-(3-dimethylaminopropyl)-N'-ethylcarbodiimide hydrochloride (41.8 g, 218 mmol) were added to a dimethylformamide (540 mL) solution of (2S)-2-acetoxy propionic acid (14.4 g, 109 mmol) at room temperature, and the mixture was stirred at the same temperature for 30 minutes. Subsequently, tert-butyl 4-amino(hydroxyimino)methyl-2-fluorobenzoate (WO 2011/016469) (27.7 g, 109 mmol) was added to the mixture. The resulting mixture was stirred at the same temperature for 10 minutes, and then further stirred at 90° C. for 3 hours. The reaction mixture was cooled to room temperature, then water and a 10% aqueous solution of sodium chloride were added to the reaction mixture, and the mixture was extracted twice with ethyl acetate. The organic layer thus obtained was washed with a 10% aqueous solution of sodium chloride and a saturated aqueous solution of sodium hydrogen carbonate, and then dried over anhydrous sodium sulfate. The solvent was distilled off under reduced pressure, and the resulting residue was purified by silica gel column chromatography (hexane:ethyl acetate=95:5→85:15, v/v) to give a compound, and then the compound (32.1 g, 91.6 mmol) thus obtained was dissolved in methanol (360 mL). Potassium carbonate (12.7 g, 91.6 mmol) was added to the mixture under ice cooling, and the resulting mixture was stirred at the same temperature for 30 minutes. 2 M Hydrochloric acid was added to the reaction mixture to adjust the pH to 6.0, and then the solvent was distilled off under reduced pressure. Water was added to the residue, and the mixture was extracted twice with ethyl acetate. The organic layer thus obtained was dried over anhydrous sodium sulfate. The solvent was distilled off under reduced pressure, and the resulting residue was washed with hexane to give the title compound (26.4 g, yield: 93%).

$^1$H-NMR (400 MHz, CDCl$_3$) δ ppm:
7.97 (1H, t, J=8 Hz), 7.90 (1H, d, J=8 Hz), 7.84 (1H, d, J=5 Hz), 5.18 (1H, q, J=7 Hz), 1.73 (4H, d, J=7 Hz), 1.60 (9H, s); MS (FAB) m/z: 309 [M+H]$^+$.

Reference Example 59

4-{5-[(1R)-1-{[6-(Cyclopropylcarbonyl)pyridin-3-yl]oxy}ethyl]-1,2,4-oxadiazol-3-yl}-2-fluorobenzoic acid

[Chemical Formula 86]

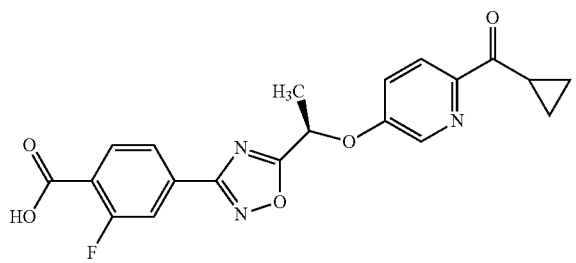

Triphenylphosphine (468 mg, 1.78 mmol) and di-tert-butyl azodicarboxylate (411 mg, 1.78 mmol) were added to a tetrahydrofuran (8.0 mL) solution of the compound obtained in Reference Example 58 (500 mg, 1.62 mmol) and the compound obtained in Reference Example 24 (291 mg, 1.78 mmol) at room temperature, and the mixture was stirred at the same temperature for 1 hour. The solvent was distilled off under reduced pressure, and the resulting residue was purified by silica gel column chromatography (hexane:ethyl acetate=90:10→75:25, v/v) to give a crude product, and then the crude product (1.18 g) thus obtained was dissolved in acetonitrile (5.0 mL). Subsequently, concentrated sulfuric acid (400 μL) was added to the mixture at room temperature, and the resulting mixture was stirred at 80° C. for 30 minutes. After the reaction mixture was cooled to room temperature, water was added to the reaction mixture, and the pH of the resulting mixture was adjusted to 6 by using a saturated aqueous solution of sodium hydrogen carbonate. The mixture was extracted twice with ethyl acetate. The organic layer thus obtained was washed with brine, and then dried over anhydrous sodium sulfate. The solvent was distilled off under reduced pressure, and the resulting residue was purified by silica gel column chromatography (hexane:ethyl acetate=70:30→0:100, v/v) to give the title compound (431 mg, yield: 67%).

$^1$H-NMR (400 MHz, CDCl$_3$) δ ppm:
8.48 (1H, d, J=3 Hz), 8.13 (1H, dd, J=8, 7 Hz), 8.04 (1H, d, J=9 Hz), 7.95 (1H, dd, J=8, 2 Hz), 7.90 (1H, dd, J=11, 2 Hz), 7.40 (1H, dd, J=9, 3 Hz), 5.80 (1H, q, J=7 Hz), 3.44-3.37 (1H, m), 1.97 (3H, d, J=7 Hz), 1.24-1.19 (2H, m), 1.11-1.05 (2H, m).

Reference Example 60

1-(5-Hydroxypyridin-2-yl)-2-methylpropan-1-one

[Chemical Formula 87]

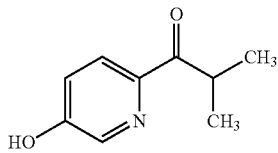

1.0 M Isopropylmagnesium chloride-tetrahydrofuran solution (104 mL, 104 mmol) was slowly added to a tetrahydrofuran (80 mL) solution of 5-hydroxypyridin-2-carbonitrile (5.00 g, 41.6 mmol) at 0° C., and the mixture was stirred at the same temperature for 3 hours. 1 M Hydrochloric acid was added to the reaction mixture, subsequently, a saturated aqueous solution of sodium hydrogen carbonate was added to the resulting mixture to adjust the pH to 6, and then the mixture was extracted twice with ethyl acetate. The organic layer thus obtained was washed with brine, and then dried over anhydrous sodium sulfate. The solvent was distilled off under reduced pressure, and the resulting residue was purified by silica gel column chromatography (hexane:ethyl acetate=80:20→50:50, v/v) to give the title compound (3.35 g, yield: 49%).

$^1$H-NMR (400 MHz, CDCl$_3$) δ ppm:
8.31 (1H, d, J=3 Hz), 8.00 (1H, d, J=9 Hz), 7.31 (1H, dd, J=9, 3 Hz), 4.05-3.98 (1H, m), 1.20 (6H, d, J=7 Hz).

Reference Example 61

2-[(6-Isobutyrylpyridin-3-yl)oxy]butyric acid

[Chemical Formula 88]

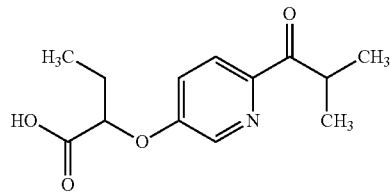

Potassium carbonate (4.81 g, 34.8 mmol) was added to an acetonitrile (23 mL) solution of the compound obtained in Reference Example 60 (2.83 g, 17.1 mmol) and ethyl 2-bromobutyrate (4.97 g, 25.5 mmol) at room temperature, and the mixture was stirred at 80° C. for 45 minutes. After the reaction mixture was cooled to room temperature, water was added to the reaction mixture, and the resulting mixture was extracted twice with ethyl acetate. The organic layer thus obtained was washed with brine, and then dried over anhydrous sodium sulfate. The solvent was distilled off under reduced pressure, the resulting residue was purified by silica gel column chromatography (hexane:ethyl acetate=100:0→85:15, v/v) to give a compound, and the compound (4.89 g) thus obtained was dissolved in tetrahydrofuran (20 mL)-methanol (20 mL). Subsequently, 1 M aqueous sodium hydroxide solution (20.6 mL) was added to the resulting mixture at room temperature, and the mixture was stirred at the same temperature for 1.5 hours. The reaction mixture was concentrated under reduced pressure, and water was added to the reaction mixture, and then the aqueous layer was washed with diethyl ether. 2 M Hydrochloric acid was added to the resulting mixture to adjust the pH to acidic, and then the mixture was extracted twice with ethyl acetate. The organic layer thus obtained was washed with brine, and then dried over anhydrous sodium sulfate. The solvent was distilled off under reduced pressure, and the resulting residue was washed with hexane to give the title compound (4.36 g, yield: 100%).

$^1$H-NMR (400 MHz, CDCl$_3$) δ ppm:
8.35 (1H, d, J=3 Hz), 8.05 (1H, d, J=9 Hz), 7.26 (1H, d, J=9, 3 Hz), 4.74 (1H, dd, J=7, 5 Hz), 4.04-3.95 (1H, m), 2.17-2.03 (2H, m), 1.19 (6H, d, J=7 Hz), 1.14 (3H, t, J=7 Hz).

Reference Example 62

Methyl 2-fluoro-4-(5-{1-[(6-isobutyrylpyridin-3-yl)oxy]propyl}-1,2,4-oxadiazol-3-yl)benzoate

[Chemical Formula 89]

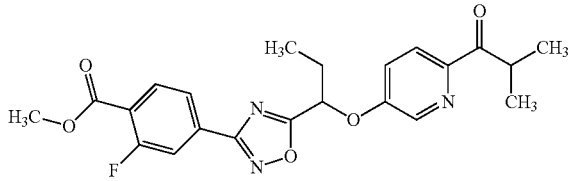

1-Hydroxybenzotriazole monohydrate (722 mg, 4.71 mmol) and N-(3-dimethylaminopropyl)-N'-ethylcarbodiimide hydrochloride (1.81 g, 9.43 mmol) were added to an N,N-dimethylformamide (10 mL) solution of the compound obtained in Reference Example 61 (1.18 g, 4.71 mmol) at room temperature, and the mixture was stirred at the same temperature for 15 minutes. Subsequently, methyl 4-amino(hydroxyimino)methyl-2-fluorobenzoate (WO 2011/016469), (1.00 g, 4.71 mmol) was added to the mixture, and the resulting mixture was stirred at the same temperature for 15 minutes, and then further stirred at 100° C. for 2.5 hours. After the reaction mixture was cooled to room temperature, water was added to the reaction mixture, and the resulting mixture was extracted twice with ethyl acetate. The organic layer thus obtained was washed with a saturated aqueous solution of sodium hydrogen carbonate and brine, and then dried over anhydrous sodium sulfate. The solvent was distilled off under reduced pressure, and the resulting residue was purified by silica gel column chromatography (hexane:ethyl acetate=100:0→70:30, v/v) to give the title compound (1.68 g, yield: 84%).

$^1$H-NMR (500 MHz, CDCl$_3$) δ ppm:
8.42 (1H, d, J=3 Hz), 8.05 (1H, dd, J=8, 7 Hz), 8.03 (1H, d, J=9 Hz), 7.92 (1H, dd, J=8, 2 Hz), 7.86 (1H, dd, J=11, 2 Hz), 7.36 (1H, dd, J=9, 3 Hz), 5.54 (1H, dd, J=7, 6 Hz), 4.07-4.00 (1H, m), 3.97 (3H, s), 2.38-2.24 (2H, m), 1.18 (6H, d, J=7 Hz), 1.16 (3H, t, J=7 Hz).

Reference Example 63

2-Fluoro-4-(5-{1-[(6-isobutyrylpyridin-3-yl)oxy]propyl}-1,2,4-oxadiazol-3-yl)benzoic acid

[Chemical Formula 90]

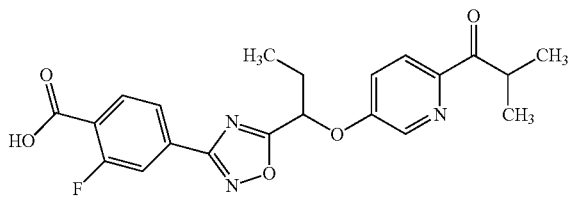

1 M Aqueous sodium hydroxide solution (4.72 mL, 4.72 mmol) was added to a tetrahydrofuran (5.0 mL)-methanol (5.0 mL) solution of the compound obtained in Reference Example 62 (1.68 g, 3.93 mmol) at room temperature, and the mixture was stirred at the same temperature for 15 minutes. The reaction mixture was concentrated under reduced pressure, then water was added to the reaction mixture, and the aqueous layer was washed with diethyl ether. 1 M Hydrochloric acid was added to the resulting mixture to adjust the pH to acidic, and then the mixture was extracted twice with ethyl acetate. The organic layer thus obtained was washed with brine, and then dried over anhydrous sodium sulfate. The solvent was distilled off under reduced pressure, and the resulting residue was washed with a hexane-diisopropyl ether mixture to give the title compound (1.50 g, yield: 93%).

$^1$H-NMR (500 MHz, CDCl$_3$) δ ppm:
8.45 (1H, d, J=3 Hz), 8.14 (1H, dd, J=8, 7 Hz), 8.05 (1H, d, J=9 Hz), 7.96 (1H, dd, J=8, 1 Hz), 7.90 (1H, dd, J=11, 1 Hz), 7.38 (1H, dd, J=9, 3 Hz), 5.56 (1H, dd, J=7, 6 Hz), 4.08-3.98 (1H, m), 2.41-2.23 (2H, m), 1.18 (6H, d, J=7 Hz), 1.17 (3H, t, J=7 Hz).

Reference Example 64

1-[5-(Methoxymethoxy)pyridin-2-yl]-3-methylbutan-1-one

[Chemical Formula 91]

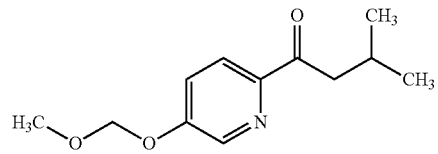

1.0 M Isobutylmagnesium bromide-tetrahydrofuran solution (9.14 mL, 9.14 mmol) was slowly added to a tetrahydrofuran (12 mL) solution of the compound obtained in Reference Example 22 (1.00 g, 6.09 mmol) at 0° C., and the mixture was stirred at the same temperature for 1.5 hours. 2 M Hydrochloric acid was added to the reaction mixture, subsequently, a saturated aqueous solution of sodium hydrogen carbonate was added to the reaction mixture to adjust the pH to basic, and then the resulting mixture was extracted twice with ethyl acetate. The organic layer thus obtained was washed with brine, and then dried over anhydrous sodium sulfate. The solvent was distilled off under reduced pressure, and the resulting residue was purified by silica gel column chromatography (hexane:ethyl acetate=100:0→80:20, v/v) to give the title compound (1.24 g, yield: 91%).

$^1$H-NMR (500 MHz, CDCl$_3$) δ ppm:
8.41 (1H, d, J=3 Hz), 8.03 (1H, d, J=9 Hz), 7.44 (1H, dd, J=9, 3 Hz), 5.27 (2H, s), 3.50 (3H, s), 3.05 (2H, d, J=7 Hz), 2.36-2.26 (1H, m), 0.99 (6H, d, J=6 Hz).

Reference Example 65

2-(1,1-Difluoro-3-methylbutyl)-5-(methoxymethoxy)pyridine

[Chemical Formula 92]

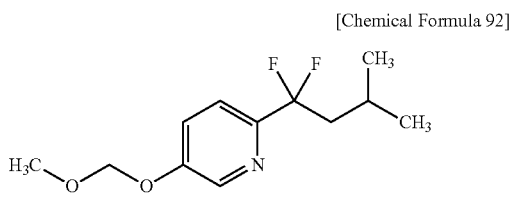 [SMILES: COCOc1ccc(C(F)(F)CC(C)C)nc1]

N,N-Diethylaminosulfur trifluoride (868 μL, 6.62 mmol) and ethanol (single drop) were added to the compound obtained in Reference Example 64 (493 mg, 2.21 mmol) at room temperature, and the mixture was stirred at the same temperature for 6 days. A saturated aqueous solution of sodium hydrogen carbonate was added to the reaction mixture, and the mixture was extracted twice with dichloromethane. The organic layer thus obtained was dried over anhydrous sodium sulfate. The solvent was distilled off under reduced pressure, and the resulting residue was purified by silica gel column chromatography (hexane:ethyl acetate=100:0→85:15, v/v) to give the title compound (144 mg, yield: 27%).

$^1$H-NMR (500 MHz, CDCl$_3$) δ ppm:
8.42 (1H, d, J=3 Hz), 7.56 (1H, d, J=9 Hz), 7.43 (1H, dd, J=9, 3 Hz), 5.23 (2H, s), 3.50 (3H, s), 2.22 (2H, td, J=18, 7 Hz), 1.93-1.84 (1H, m), 0.95 (6H, d, J=7 Hz).

Reference Example 66

6-(1,1-Difluoro-3-methylbutyl)pyridin-3-ol

[Chemical Formula 93]

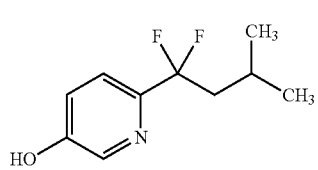

2 M Hydrochloric acid (2.0 mL) was added to a tetrahydrofuran (2.0 mL) solution of the compound obtained in Reference Example 65 (137 mg, 0.559 mmol) at room temperature, and the mixture was stirred at 50° C. for 3 hours. The reaction mixture was cooled to room temperature, and then 1 M aqueous sodium hydroxide solution was added to the reaction mixture to adjust the pH to 7. Subsequently, the resulting mixture was extracted three times with ethyl acetate. The organic layer thus obtained was washed with brine, and then dried over anhydrous sodium sulfate. The solvent was distilled off under reduced pressure, and the resulting residue was washed with a hexane-dichloromethane mixture to give the title compound (88.0 mg, yield: 79%).

$^1$H-NMR (500 MHz, CDCl$_3$) δ ppm:
8.27 (1H, d, J=2 Hz), 7.54 (1H, d, J=9 Hz), 7.25 (1H, dd, J=9, 2 Hz), 2.20 (2H, td, J=18, 7 Hz), 1.92-1.83 (1H, m), 0.94 (6H, d, J=7 Hz).

Reference Example 67

(2S)-2-Acetoxy butyric acid

[Chemical Formula 94]

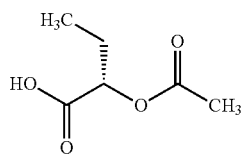

Sodium acetate (11.9 g, 146 mmol) and tert-butyl nitrite (15.0 g, 146 mmol) were added to an acetic acid (300 mL) solution of (2S)-2-aminobutyric acid (10.0 g, 97.0 mmol) under ice cooling, and the mixture was stirred at 60° C. for 2 hours. After the reaction mixture was cooled to room temperature, the solvent was distilled off under reduced pressure, then water was added to the reaction mixture, and the resulting mixture was extracted twice with ethyl acetate. The organic layer thus obtained was washed with water and brine, and then dried over anhydrous sodium sulfate. The solvent was distilled off under reduced pressure, and further, the resulting residue was azeotropically boiled twice with 1,4-dioxane (50 mL) to give the title compound (8.4 g, yield: 60%).

$^1$H-NMR (400 MHz, CDCl$_3$) δ ppm:
5.00 (1H, m), 2.15 (3H, s), 1.94-1.90 (2H, m), 1.03 (3H, t, J=7 Hz);
MS (FAB) m/z: 147 [M+H]$^+$.

Reference Example 68 tert-Butyl 4-{5-[(1S)-1-acetoxypropyl]-1,2,4-oxadiazol-3-yl}-2-fluorobenzoate

[Chemical Formula 95]

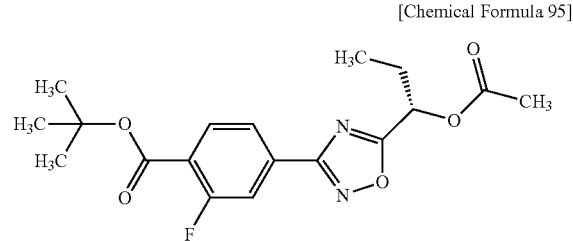 [SMILES: CC[C@H](OC(C)=O)c1nc(-c2ccc(C(=O)OC(C)(C)C)c(F)c2)no1]

1-Hydroxybenzotriazole monohydrate (7.2 g, 53.0 mmol) and N-(3-dimethylaminopropyl)-N'-ethylcarbodiimide hydrochloride (20.3 g, 159 mmol) were added to an N,N-dimethylformamide (200 mL) solution of the compound obtained in Reference Example 67 (7.8 g, 53.0 mmol) at room temperature, and the mixture was stirred at the same temperature for 30 minutes. The compound obtained in Reference Example 2 (13.5 g, 53.0 mmol) was added, and the mixture was stirred for 30 minutes, and further stirred at 100° C. for 3 hours. After the reaction mixture was returned to room temperature, water was added to the reaction mixture, and the resulting mixture was extracted twice with ethyl acetate. The organic layer thus obtained was washed with water and a 10% aqueous solution of sodium chloride, and then dried over anhydrous sodium sulfate. The solvent was distilled off under reduced pressure, and the resulting residue was purified by silica gel column chromatography (hexane:ethyl acetate=95:5→85:15, v/v) to give the title compound (14.7 g, yield: 76%).

$^1$H-NMR (400 MHz, CDCl$_3$) δ ppm:

7.96 (1H, t, J=8 Hz), 7.90 (1H, dd, J=8, 2 Hz), 7.84 (1H, dd, J=11, 2 Hz), 5.92 (1H, t, J=7 Hz), 2.21 (3H, s), 2.16-2.08 (2H, m), 1.62 (9H, s), 1.05 (3H, t, J=7 Hz);

MS (FAB) m/z: 365 [M+H]$^+$.

Reference Example 69 tert-Butyl 2-fluoro-4-{5-[(1S)-1-hydroxypropyl]-1,2,4-oxadiazol-3-yl}benzoate

[Chemical Formula 96]

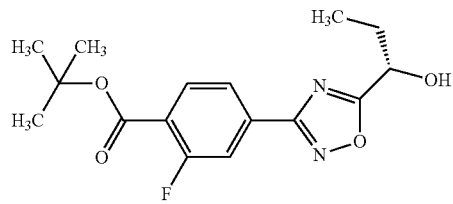

Potassium carbonate (8.4 g, 61 mmol) was added to a methanol (100 mL) solution of the compound obtained in Reference Example 68 (14.7 g, 40.3 mmol) under ice cooling, and the mixture was stirred at the same temperature for 30 minutes. 2 N Hydrochloric acid was added to the reaction mixture at the same temperature until a pH value of 6.0 was obtained. The reaction mixture was extracted twice with ethyl acetate, and the organic layer thus obtained was washed with water and brine, and then dried over anhydrous sodium sulfate. The solvent was distilled off under reduced pressure, and the resulting residue was purified by silica gel column chromatography (hexane:ethyl acetate=95:5→80:20, v/v) to give the title compound (12.9 g, yield: 84%).

$^1$H-NMR (400 MHz, CDCl$_3$) δ ppm:

7.97 (1H, t, J=8 Hz), 7.91 (1H, d, J=8 Hz), 7.85 (1H, d, J=11 Hz), 4.98 (1H, q, J=6 Hz), 2.54 (1H, brs), 2.14-1.96 (2H, m), 1.62 (9H, s), 1.08 (3H, t, J=7 Hz);

MS (FAB$^+$) m/z: 323 [M+H]$^+$.

Reference Example 70 tert-Butyl 4-{5-[(1R)-1-{[6-(1,1-difluoro-3-methylbutyl)pyridin-3-yl]oxy}propyl]-1,2,4-oxadiazol-3-yl}-2-fluorobenzoate

[Chemical Formula 97]

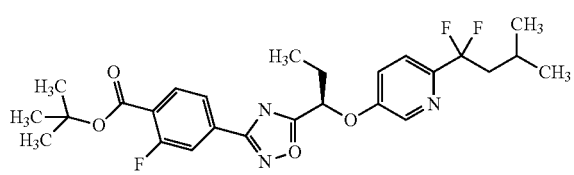

Triphenylphosphine (57.4 mg, 0.219 mmol) and di-tert-butyl azodicarboxylate (50.4 mg, 0.219 mmol) were added to a tetrahydrofuran (1.0 mL) solution of the compound obtained in Reference Example 69 (70.5 mg, 0.219 mmol) and the compound obtained in Reference Example 66 (40.0 mg, 0.199 mmol) at 0° C., and the mixture was stirred at the same temperature for 10 minutes, and then further stirred at room temperature for 3 hours. The reaction mixture was concentrated under reduced pressure, and the resulting residue was purified by silica gel column chromatography (hexane:ethyl acetate=100:0→90:10, v/v) to give the title compound (87.0 mg, yield: 87%).

$^1$H-NMR (400 MHz, CDCl$_3$) δ ppm:

8.46 (1H, d, J=3 Hz), 8.12 (1H, dd, J=8, 7 Hz), 7.96 (1H, d, J=8 Hz), 7.90 (1H, d, J=11 Hz), 7.58 (1H, d, J=9 Hz), 7.37 (1H, dd, J=9, 3 Hz), 5.49 (1H, dd, J=7, 6 Hz), 2.38-2.13 (4H, m), 1.91-1.82 (1H, m), 1.16 (3H, t, J=7 Hz), 0.94 (6H, d, J=7 Hz).

Reference Example 71

4-Amino-3-fluoro-N'-hydroxybenzenecarboxyimidamide

[Chemical Formula 98]

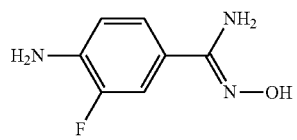

A 50% aqueous solution of Hydroxylamine (2.18 mL, 33.1 mmol) was added to a 2-propanol (44 mL) solution of 4-amino-3-fluorobenzonitrile (3.00 g, 22.0 mmol) at room temperature, and the mixture was stirred at 70° C. for 5 hours. After the reaction mixture was cooled to room temperature, the solvent was distilled off under reduced pressure, and the resulting residue was washed with a hexane-ethyl acetate (4:1, v/v) mixture to give the title compound (3.67 g, yield: 98%).

$^1$H-NMR (500 MHz, DMSO-d$_6$) δ ppm:

9.35 (1H, s), 7.27 (1H, dd, J=13, 2 Hz), 7.21 (1H, dd, J=8, 2 Hz), 6.71 (1H, dd, J=9, 8 Hz), 5.63 (2H, s), 5.33 (2H, s).

Reference Example 72

Acetic acid (1S)-1-[3-(4-amino-3-fluorophenyl)-1,2,4-oxadiazol-5-yl]propyl

[Chemical Formula 99]

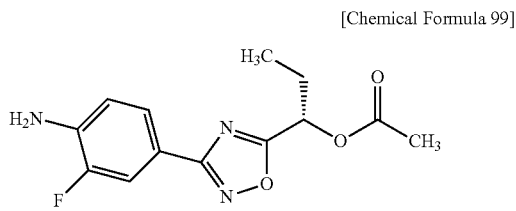 [SMILES: CC[C@H](OC(C)=O)c1nc(-c2ccc(N)c(F)c2)no1]

1-Hydroxybenzotriazole monohydrate (577 mg, 3.77 mmol) and N-(3-dimethylaminopropyl)-N'-ethylcarbodiimide hydrochloride (1.44 g, 7.53 mmol) were added to a N,N-dimethylformamide (19 mL) solution of the compound obtained in Reference Example 67 (550 mg, 3.77 mmol) at room temperature, and the mixture was stirred at the same temperature for 30 minutes. Subsequently, the compound obtained in Reference Example 71 (637 mg, 3.77 mmol) was added to the mixture, and the resulting mixture was stirred at the same temperature for 15 minutes, and then further stirred at 100° C. for 1 hour. The reaction mixture was cooled to room temperature. Subsequently, water was added to the reaction mixture, and the resulting mixture was extracted twice with ethyl acetate. The organic layer thus obtained was washed with a saturated aqueous solution of sodium hydrogen carbonate and brine, and then dried over anhydrous sodium sulfate. The solvent was distilled off under reduced pressure, and the resulting residue was purified by silica gel column chromatography (hexane:ethyl acetate=90:10→60:40, v/v) to give the title compound (563 mg, yield: 62%).

$^1$H-NMR (500 MHz, CDCl$_3$) δ ppm:
7.74-7.66 (2H, m), 6.82 (1H, dd, J=9, 8 Hz), 5.90 (1H, dd, J=7, 6 Hz), 4.03 (1H, s), 2.19 (3H, d, J=4 Hz), 2.16-2.04 (2H, m), 1.03 (2H, t, J=8 Hz).

Reference Example 73

(1S)-1-[3-(4-Amino-3-fluorophenyl)-1,2,4-oxadiazol-5-yl]propan-1-ol

[Chemical Formula 100]

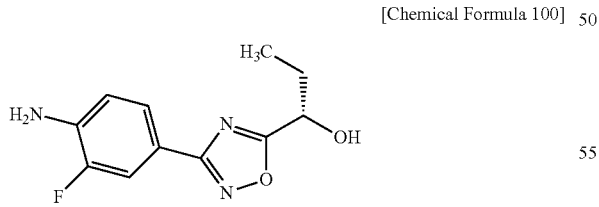

Potassium carbonate (417 mg, 3.02 mmol) was added to a methanol (10 mL) solution of the compound obtained in Reference Example 72 (562 mg, 2.01 mmol) at room temperature, and the mixture was stirred at the same temperature for 15 minutes. 1 M Hydrochloric acid was added to the reaction mixture, and the mixture was extracted twice with ethyl acetate. The organic layer thus obtained was washed with brine, and then dried over anhydrous sodium sulfate. The solvent was distilled off under reduced pressure, and the resulting residue was washed with a hexane-ethyl acetate mixture to give the title compound (438 mg, yield: 92%).

$^1$H-NMR (500 MHz, CDCl$_3$) δ ppm:
7.74-7.66 (2H, m), 6.83 (1H, dd, J=9, 8 Hz), 4.92 (1H, dd, J=7, 6 Hz), 4.04 (2H, br s), 2.64 (1H, br s), 2.11-1.93 (2H, m), 1.06 (3H, t, J=8 Hz).

Reference Example 74

[4-({(1R)-1-[3-(4-Amino-3-fluorophenyl)-1,2,4-oxadiazol-5-yl]propyl}oxy)phenyl](cyclopropyl)methanone

[Chemical Formula 101]

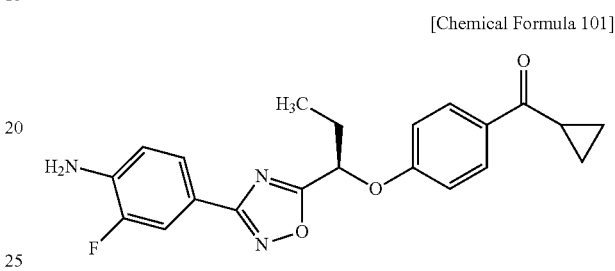

Triphenylphosphine (243 mg, 0.927 mmol) and di-tert-butyl azodicarboxylate (214 mg, 0.927 mmol) were added to a tetrahydrofuran (4.2 mL) solution of the compound obtained in Reference Example 73 (200 mg, 0.843 mmol) and cyclopropyl(4-hydroxyphenyl)methanone (150 mg, 0.927 mmol) at 0° C., and the mixture was stirred at the same temperature for 5 minutes, and then further stirred at room temperature for 1.5 hours. The solvent was distilled off under reduced pressure, and the resulting residue was purified by silica gel column chromatography (hexane:ethyl acetate=85:15→70:30, v/v) to give the title compound (279 mg, yield: 87%).

$^1$H-NMR (500 MHz, CDCl$_3$) δ ppm:
7.98 (2H, d, J=9 Hz), 7.72-7.65 (2H, m), 7.03 (2H, d, J=9 Hz), 6.81 (1H, dd, J=9, 8 Hz), 5.47 (1H, dd, J=7, 6 Hz), 4.04 (2H, s), 2.62-2.56 (1H, m), 2.33-2.16 (2H, m), 1.22-1.17 (2H, m), 1.12 (3H, t, J=7 Hz), 1.01-0.96 (2H, m).

Reference Example 75

2-{[6-(Cyclopropylcarbonyl)pyridin-3-yl]propionic acid

[Chemical Formula 102]

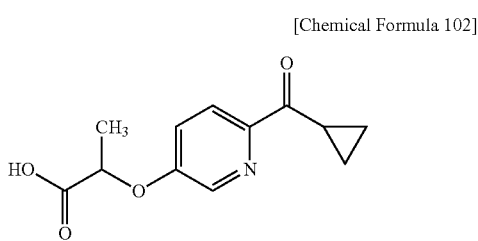 [SMILES: CC(Oc1ccc(C(=O)C2CC2)nc1)C(=O)O]

Potassium carbonate (1.27 g, 9.19 mmol) was added to an acetonitrile (10 mL) solution of the compound obtained in Reference Example 24 (1.00 g, 6.13 mmol) and methyl 2-bromopropionate (1.02 g, 6.13 mmol) at room temperature, and the mixture was stirred at 80° C. for 3 hours. After the reaction mixture was cooled to room temperature, water was added to the reaction mixture, and the resulting mixture was extracted once with toluene. The organic layer thus obtained was washed with 1 M aqueous sodium hydroxide solution and brine, and then dried over anhydrous sodium sulfate. The solvent was distilled off under reduced pressure, and the resulting residue (1.44 g) was dissolved in tetrahydrofuran (7.0 mL)-methanol (7.0 mL). 1 M Aqueous sodium hydroxide solution (6.93 mL, 6.93 mmol) was added to the mixture at room temperature, and the mixture was stirred at the same temperature for 30 minutes. The reaction mixture was concentrated under reduced pressure, then water was added to the resulting reaction mixture, and the aqueous layer was washed with diethyl ether. 1 M Sulfuric acid was added to the mixture to adjust the pH to 6, and then the resulting mixture was extracted twice with ethyl acetate. The organic layer thus obtained was washed with brine, and then dried over anhydrous sodium sulfate. The solvent was distilled off under reduced pressure, and the resulting residue was washed with a hexane-diisopropyl ether (10:1, v/v) mixture to give the title compound (1.27 g, yield: 88%).

$^1$H-NMR (400 MHz, CDCl$_3$) δ ppm:
8.38 (1H, d, J=3 Hz), 8.03 (1H, d, J=9 Hz), 7.26 (1H, dd, J=9, 2 Hz), 4.93 (1H, q, J=7 Hz), 3.41-3.35 (1H, m), 1.74 (3H, d, J=7 Hz), 1.25-1.20 (2H, m), 1.10-1.05 (2H, m).

Reference Example 76

(5-{1-[3-(4-Amino-3-fluorophenyl)-1,2,4-oxadiazol-5-yl]ethoxy}pyridin-2-yl)(cyclopropyl)methanone

[Chemical Formula 103]

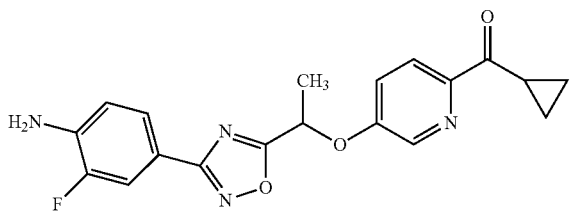

1-Hydroxybenzotriazole monohydrate (215 mg, 1.40 mmol) and N-(3-dimethylaminopropyl)-N'-ethylcarbodiimide hydrochloride (489 mg, 2.55 mmol) were added to a N,N-dimethylformamide (6.4 mL) solution of the compound obtained in Reference Example 75 (300 mg, 1.28 mmol) at room temperature, and the mixture was stirred at the same temperature for 30 minutes. Subsequently, the compound obtained in Reference Example 71 (216 mg, 1.28 mmol) was added to the mixture, and the resulting mixture was stirred at the same temperature for 15 minutes, and then further stirred at 100° C. for 1 hour. The reaction mixture was cooled to room temperature. Subsequently, water was added to the reaction mixture, and the resulting mixture was extracted twice with ethyl acetate. The organic layer thus obtained was washed with a saturated aqueous solution of sodium hydrogen carbonate and brine, and then dried over anhydrous sodium sulfate. The solvent was distilled off under reduced pressure, and the resulting residue was purified by silica gel column chromatography (hexane:ethyl acetate=90:10→50:50, v/v) to give the title compound (401 mg, yield: 85%).

$^1$H-NMR (400 MHz, CDCl$_3$) δ ppm:
8.46 (1H, d, J=3 Hz), 8.02 (1H, d, J=9 Hz), 7.69 (1H, dd, J=12, 2 Hz), 7.67 (1H, dd, J=8, 2), 7.38 (1H, dd, J=9, 3 Hz), 6.82 (1H, dd, J=9, 8 Hz), 5.73 (1H, q, J=7 Hz), 4.06 (2H, s), 3.46-3.93 (1H, m), 1.93 (3H, d, J=7 Hz), 1.23-1.19 (2H, m), 1.10-1.04 (2H, m).

Reference Example 77

2-Fluoro-4-(5-{1-[4-(5-isopropyl-1,2,4-oxadiazol-3-yl)phenoxy]propyl}-1,2,4-oxadiazol-3-yl)aniline

[Chemical Formula 104]

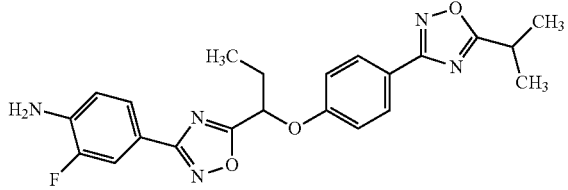

N-(3-Dimethylaminopropyl)-N'-ethylcarbodiimide hydrochloride (2.66 g, 14.3 mmol) was added to a N,N-dimethylformamide (60 mL) solution of 2-[4-(5-isopropyl-1,2,4-oxadiazol-3-yl)phenoxy]butyric acid (WO 2011/016469) (4.16 g, 14.3 mmol) at room temperature, and the mixture was stirred at the same temperature for 20 minutes. The compound obtained in Reference Example 71 (2.35 g, 14.3 mmol) was added, and then the mixture was heated at 100° C. for 3.5 hours. After the reaction mixture was cooled to room temperature, water was added to the reaction mixture, and the resulting mixture was extracted three times with ethyl acetate, and then dried over anhydrous sodium sulfate. The solvent was distilled off under reduced pressure, and the resulting residue was purified by silica gel column chromatography (hexane:ethyl acetate=9:1→1:2, v/v) to give the title compound (2.06 g, yield: 35%).

$^1$H-NMR (400 MHz, CDCl$_3$) δ ppm:
8.03 (2H, d, J=9 Hz), 7.76-7.68 (2H, m), 7.10 (2H, d, J=9 Hz), 6.85 (1H, dd, J=9, 8 Hz), 5.49 (1H, t, J=7 Hz), 4.08 (2H, bs), 3.34-3.24 (m, 1H), 2.38-2.20 (2H, m), 1.47 (6H, d, J=7 Hz), 1.13 (3H, t, J=8 Hz).

Reference Example 78

2-Fluoro-4-(5-{(1R)-1-[4-(5-isopropyl-1,2,4-oxadiazol-3-yl)phenoxy]propyl}-1,2,4-oxadiazol-3-yl)aniline

[Chemical Formula 105]

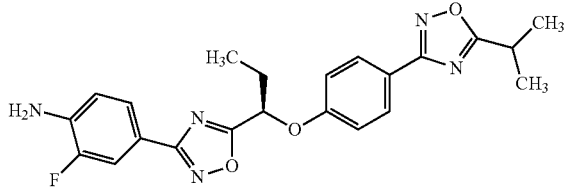

N-(3-Dimethylaminopropyl)-N'-ethylcarbodiimide hydrochloride (2.53 g, 13.2 mmol) was added to a N,N-dimethylformamide (50 mL) solution of (2R)-2-[4-(5-isopropyl-1,2,4-oxadiazol-3-yl)phenoxy]butyric acid (WO 2011/016469) (1.49 g, 8.80 mmol) at room temperature, and the mixture was stirred at the same temperature for 15 minutes. The compound obtained in Reference Example 71 (2.55 g, 8.80 mmol) was added to the mixture, and then the mixture was heated at 100° C. for 3 hours. After the reaction mixture was cooled to room temperature, water was added to the reaction mixture, and the resulting mixture was extracted three times with ethyl acetate. The organic layer thus obtained was washed with water, and then dried over anhydrous sodium sulfate. The solvent was distilled off under reduced pressure, and the resulting residue was purified by silica gel column chromatography (hexane:ethyl acetate=9:1→1:2, v/v) to give the title compound (1.69 g, yield: 45%).

$^{1}$H-NMR (400 MHz, CDCl$_{3}$) δ ppm:

8.00 (2H, d, J=9 Hz), 7.73-7.65 (2H, m), 7.06 (2H, d, J=9 Hz), 6.81 (1H, dd, J=9, 8 Hz), 5.46 (1H, t, J=7 Hz), 3.30-3.19 (m, 1H), 2.32-2.17 (2H, m), 1.43 (6H, d, J=7 Hz), 1.13 (3H, t, J=8 Hz).

Reference Example 79 tert-Butyl 2-fluoro-4-formylbenzoate

[Chemical Formula 106]

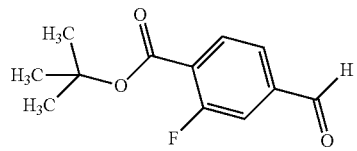

tert-Butyl 4-amino(hydroxyimino)methyl-2-fluorobenzoate (WO 2011/016469) (3.90 g, 17.6 mmol) was dissolved in ethanol (40 mL) and acetic acid (40 mL). Raney nickel (ca. 10 g) was added to the mixture at room temperature, and the resulting mixture was stirred for 1 hour under hydrogen flow. After the insoluble material was removed by filtration through Celite, water was added to the filtrate, and the resulting mixture was extracted three times with ethyl acetate, and then dried over anhydrous sodium sulfate. The solvent was distilled off under reduced pressure, and then water and a saturated aqueous solution of sodium hydrogen carbonate were added to the mixture. The resulting mixture was extracted with ethyl acetate, and dried over anhydrous sodium sulfate. The solvent was distilled off under reduced pressure, and the resulting residue was purified by silica gel column chromatography (hexane:ethyl acetate=95:5→2:1, v/v) to give the title compound (2.21 g, yield: 56%).

$^{1}$H-NMR (400 MHz, CDCl$_{3}$) δ ppm:

10.0 (1H, d, J=2 Hz), 8.01 (1H, dd, J=8, 7 Hz), 7.69 (1H, d, J=8, 2 Hz), 7.61 (1H, dd, J=10, 2 Hz), 1.61 (9H, s).

Reference Example 80

4-(tert-Butoxycarbonyl)-3-fluorobenzoic acid

[Chemical Formula 107]

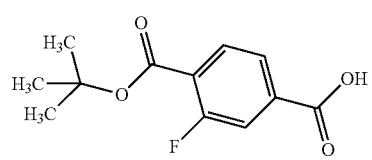

The compound obtained in Reference Example 79 (1.54 g, 6.87 mmol) was dissolved in tert-butanol (15 mL) and water (15 mL), then sodium dihydrogen phosphate dihydrate (5.36 g, 34.3 mmol), 2-methyl-2-butene (7.30 mL, 68.7 mmol), and sodium chlorite (2.35 g, 20.6 mmol) were added to the mixture at room temperature, and the resulting mixture was stirred at room temperature for 30 minutes. Water was added to the reaction mixture, and the resulting mixture was extracted three times with ethyl acetate. The organic layer thus obtained was washed with water, and then dried over anhydrous sodium sulfate. The solvent was distilled off under reduced pressure, and the resulting residue was washed with hexane to give the title compound (1.16 g, yield: 70%).

$^{1}$H-NMR (400 MHz, CDCl$_{3}$) δ ppm:

7.97-7.89 (2H, m), 7.83 (1H, dd, J=11, 1 Hz), 1.62 (9H, s).

Reference Example 81

2-[4-(Cyclopropylcarbonyl)phenoxy]propionic acid

[Chemical Formula 108]

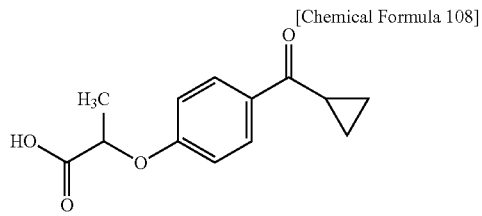 [SMILES: CC(Oc1ccc(C(=O)C2CC2)cc1)C(=O)O]

Potassium carbonate (6.39 g, 46.2 mmol) was added to an acetonitrile (200 mL) solution of cyclopropyl(4-hydroxyphenyl)methanone (5.00 g, 30.8 mmol) and methyl 2-bromopropionate (5.66 g, 33.9 mmol) at room temperature, and the mixture was stirred at 80° C. for 2.5 hours. After the reaction mixture was cooled to room temperature, ethyl acetate was added to the reaction mixture, and the insoluble material was removed by filtration through Celite. The filtrate was concentrated to around half volume under reduced pressure, then water was added to the filtrate, and the resulting mixture was extracted once with ethyl acetate. The organic layer thus obtained was washed with water, and then dried over anhydrous magnesium sulfate. The solvent was distilled off under reduced pressure, and a mixture containing methyl 2-[4-(cyclopropylcarbonyl)phenoxy]propionate (7.99 g) was obtained. The mixture (7.99 g) thus obtained was dissolved in methanol (100 mL), then 2 M aqueous sodium hydroxide solution (31 mL, 62 mmol) was added to the mixture at room temperature, and the resulting mixture was stirred at the same temperature for 1 hour. The reaction mixture was concentrated under reduced pressure, then water was added to the reaction mixture, and 2 M sulfuric acid was added to the resulting mixture to adjust the pH to 2. The resulting mixture was extracted twice with ethyl acetate. The organic layer thus obtained was washed with brine, and then dried over anhydrous magnesium sulfate. The solvent was distilled off under reduced pressure, and the resulting residue was purified by silica gel column chromatography (methylene chloride:methanol=9:1→8:1, v/v) to give the title compound (7.03 g, yield: 98%).

$^{1}$H-NMR (400 MHz, CDCl$_{3}$) δ ppm:

8.01-7.99 (2H, m), 6.95-6.93 (2H, m), 4.88 (2H, q, J=7 Hz), 2.65-2.59 (1H, m), 1.70 (3H, d, J=7 Hz), 1.24-1.20 (2H, m), 1.03-1.01 (2H, m).

Reference Example 82

2-[4-(Cyclopropylcarbonyl)phenoxy]propanenitrile

[Chemical Formula 109]

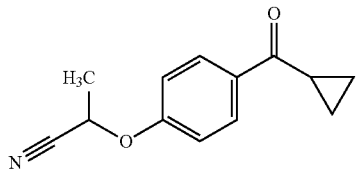

Carbonyldiimidazole (1.07 g, 6.60 mmol) was added to a tetrahydrofuran (15 mL) solution of the compound obtained in Reference Example 81 (1.03 g, 4.40 mmol) at room temperature, and the mixture was stirred at the same temperature for 40 minutes. A 28% aqueous ammonia solution (7 mL, excess amount) was added to the mixture at room temperature, and the resulting mixture was stirred at the same temperature for 20 minutes. Water was added to the reaction mixture, and the resulting mixture was extracted three times with ethyl acetate, and then dried over anhydrous sodium sulfate. The solvent was distilled off under reduced pressure, and the resulting residue was purified by silica gel column chromatography (hexane:ethyl acetate=1:1→ethyl acetate, v/v). Subsequently, trifluoroacetic anhydride (0.612 mL, 4.40 mmol) was added to a methylene chloride (20 mL) solution of the compound thus obtained and pyridine (0.708 mL, 8.79 mmol) at 0° C., and the mixture was stirred at the same temperature for 20 minutes. Water and a saturated aqueous solution of ammonium chloride were added to the reaction mixture at 0° C., and the mixture was extracted three times with methylene chloride. The organic layer thus obtained was washed with water and a 1 M aqueous sodium hydroxide solution sequentially, and then dried over anhydrous sodium sulfate. The solvent was distilled off under reduced pressure, and the resulting residue was purified by silica gel column chromatography (hexane:ethyl acetate=9:1→2:1, v/v) to give the title compound (867 mg, yield: 92%).

$^1$H-NMR (400 MHz, CDCl$_3$) δ ppm:
8.06 (2H, d, J=9 Hz), 7.06 (2H, d, J=9 Hz), 4.99 (1H, q, J=7 Hz), 2.67-2.58 (1H, m), 1.84 (3H, d, J=7 Hz), 1.39-1.32 (2H, m), 1.06-1.01 (2H, m).

Reference Example 83

(1Z)-2-[4-(Cyclopropylcarbonyl)phenoxy]-N'-hydroxypropanimidamide

[Chemical Formula 110]

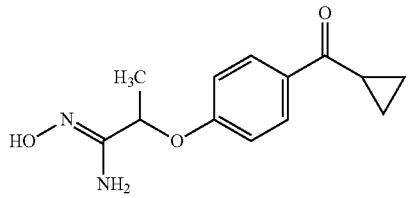

A 50% aqueous hydroxylamine solution (0.328 mL, 5.52 mmol) was added to an ethanol (4 mL) solution of the compound obtained in Reference Example 82 (594 mg, 2.76 mmol) at room temperature, and the mixture was stirred at the same temperature for 30 minutes. The solvent was distilled off under reduced pressure to give the title compound (648 mg, yield: 95%).

$^1$H-NMR (400 MHz, CDCl$_3$) δ ppm:
8.00 (2H, d, J=9 Hz), 7.06 (2H, d, J=9 Hz), 4.87 (1H, q, J=7 Hz), 4.68 (2H, bs), 2.64-2.57 (2H, m), 1.64 (3H, d, J=7 Hz), 1.25-1.18 (2H, m), 1.04-0.98 (2H, m).

Reference Example 84

4-(3-{1-[4-(Cyclopropylcarbonyl)phenoxy]ethyl}-1,2,4-oxadiazol-5-yl)-2-fluorobenzoic acid

[Chemical Formula 111]

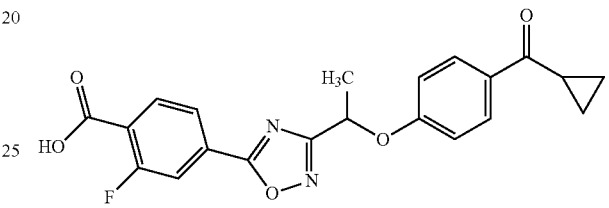

1-Hydroxybenzotriazole monohydrate (574 mg, 3.75 mmol) and N-(3-dimethylaminopropyl)-N'-ethylcarbodiimide hydrochloride (1.44 g, 7.49 mmol) were added to an N,N-dimethylformamide (20 mL) solution of the compound obtained in Reference Example 80 (900 mg, 3.75 mmol) at room temperature, and the mixture was stirred at the same temperature for 30 minutes. The compound obtained in Reference Example 83 (930 mg, 3.75 mmol) was added to the mixture at room temperature, and the resulting mixture was stirred at room temperature for 20 minutes, and then heated at 90° C. for 6 hours. After the reaction mixture was cooled to room temperature, water and a saturated aqueous solution of sodium hydrogen carbonate were added to the reaction mixture. The resulting mixture was extracted three times with ethyl acetate. The organic layer thus obtained was washed with a 10% aqueous solution of sodium chloride, and then dried over anhydrous sodium sulfate. The solvent was distilled off under reduced pressure, and the resulting residue was purified by silica gel column chromatography (hexane:ethyl acetate=9:1-41:1, v/v) to give a mixture containing tert-butyl 4-(3-{1-[4-(cyclopropylcarbonyl)phenoxy]ethyl}-1,2,4-oxadiazol-5-yl)-2-fluorobenzoate. Subsequently, a methylene chloride (2 mL) solution of trifluoroacetic acid (2 mL) was added to a methylene chloride (4 mL) solution of the mixture thus obtained at room temperature, and the resulting mixture was stirred at the same temperature for 30 minutes. Trifluoroacetic acid (2 mL) was added to the mixture at room temperature, and the resulting mixture was stirred at the same temperature for 20 minutes. The solvent was distilled off under reduced pressure, and the resulting residue was purified by silica gel column chromatography (hexane:ethyl acetate=2:1→1:4, v/v) to give the title compound (655 mg, yield: 44%).

$^1$H-NMR (400 MHz, CDCl$_3$) δ ppm:
8.20-8.14 (1H, m), 8.03-7.92 (4H, m), 7.08 (2H, d, J=9 Hz), 5.72 (1H, q, J=7 Hz), 2.63-2.56 (1H, m), 1.87 (3H, d, J=6 Hz), 1.21-1.17 (2H, m), 1.01-0.96 (2H, m).

Reference Example 85

(4-{1-[5-(4-Amino-3-fluorophenyl)-1,2,4-oxadiazol-3-yl]ethoxy}phenyl)(cyclopropyl)methanone

[Chemical Formula 112]

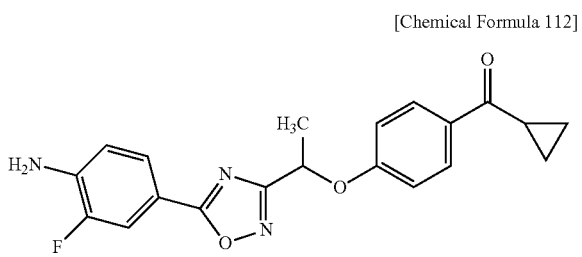 [SMILES: CC(Oc1ccc(C(=O)C2CC2)cc1)c1noc(-c2ccc(N)c(F)c2)n1]

Triethylamine (0.193 mL, 1.39 mmol) and diphenylphosphoryl azide (0.299 mL, 1.39 mmol) were added to a tert-butanol (6 mL) solution of the compound obtained in Reference Example 84 (499 mg, 1.26 mmol) at room temperature, and the mixture was heated at 80° C. for 6 hours. After the reaction mixture was cooled to room temperature, water was added to the reaction mixture, and the resulting mixture was extracted three times with ethyl acetate, and then dried over anhydrous sodium sulfate. The solvent was distilled off under reduced pressure, and the resulting residue was purified by silica gel column chromatography (hexane:ethyl acetate=9:1→1:1, v/v). Subsequently, a methylene chloride (1 mL) solution of trifluoroacetic acid (1 mL) was added to a methylene chloride (2 mL) solution of the compound thus obtained at room temperature, and the mixture was stirred at the same temperature for 30 minutes. Trifluoroacetic acid (1 mL) was added to the mixture at room temperature, and the resulting mixture was stirred at the same temperature for 30 minutes. The solvent was distilled off under reduced pressure, and the resulting residue was purified by silica gel column chromatography (hexane:ethyl acetate=9:1→1:2, v/v) to give the title compound (255 mg, yield: 55%).

$^1$H-NMR (400 MHz, CDCl$_3$) δ ppm:
7.98 (2H, d, J=9 Hz), 7.76-7.72 (2H, m), 7.08 (2H, d, J=9 Hz), 6.82 (1H, t, J=9 Hz), 5.66 (1H, q, J=7 Hz), 2.64-2.57 (1H, m), 1.84 (3H, d, J=6 Hz), 1.21-1.17 (2H, m), 1.02-0.95 (2H, m).

Reference Example 86

2-[4-(Cyclopropylcarbonyl)phenoxy]butanamide

[Chemical Formula 113]

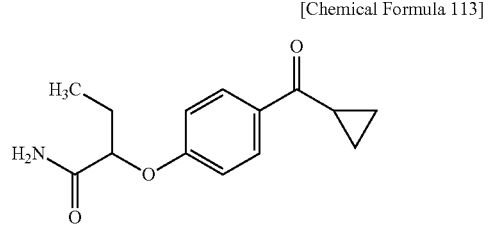 [SMILES: CCC(Oc1ccc(C(=O)C2CC2)cc1)C(N)=O]

Tripotassium phosphate (8.17 g, 38.5 mmol) and ethyl 2-bromobutyrate (4.77 mL, 32.6 mmol) were added to an acetone (24 mL) solution of cyclopropyl(4-hydroxyphenyl)methanone (4.80 g, 29.6 mmol) at room temperature, and the mixture was stirred for 4 hours under reflux. Tripotassium phosphate (1.57 g, 7.40 mmol) and ethyl 2-bromobutyrate (1.08 mL, 7.40 mmol) were added to the mixture at room temperature, and the resulting mixture was stirred for 3 hours under reflux. After the reaction mixture was cooled to room temperature, water was added to the reaction mixture, and the resulting mixture was extracted once with acetone. The solvent was distilled off under reduced pressure, and the resulting residue was purified by silica gel column chromatography (hexane:ethyl acetate=20:1→1:1, v/v). Subsequently, the compound thus obtained was dissolved in water (45 mL), then 5 M aqueous sodium hydroxide solution (8.78 mL, 44.4 mmol) was added to the mixture at room temperature, and the resulting mixture was stirred at the same temperature for 2 hours. Water and a saturated aqueous solution of ammonium chloride were added to the reaction mixture, and the mixture was extracted three times with ethyl acetate, and then dried over anhydrous sodium sulfate. The solvent was distilled off under reduced pressure. Carbonyldiimidazole (7.20 g, 44.4 mmol) was added to a tetrahydrofuran (150 mL) solution of the compound thus obtained (7.35 g, 29.5 mmol) at room temperature, and the mixture was stirred at the same temperature for 30 minutes. A 28% aqueous ammonia solution (30 mL, excess amount) was added to the mixture at room temperature, and the resulting mixture was stirred at the same temperature for 30 minutes. Water was added to the reaction mixture, and the resulting mixture was extracted three times with ethyl acetate, and then dried over anhydrous sodium sulfate. The solvent was distilled off under reduced pressure, and the resulting residue was purified by silica gel column chromatography (hexane:ethyl acetate=1:1→ethyl acetate, v/v) to give the title compound (6.41 g, yield: 87%).

$^1$H-NMR (400 MHz, CDCl$_3$) δ ppm:
8.02 (2H, d, J=9 Hz), 6.99 (2H, d, J=9 Hz), 6.28 (1H, bs), 5.74 (1H, bs), 4.62 (1H, dd, J=6, 5 Hz), 2.66-2.52 (1H, m), 2.10-1.95 (2H, m), 1.25-1.20 (2H, m), 1.10-1.00 (5H, m).

Reference Example 87

2-[4-(Cyclopropylcarbonyl)phenoxy]butanenitrile

[Chemical Formula 114]

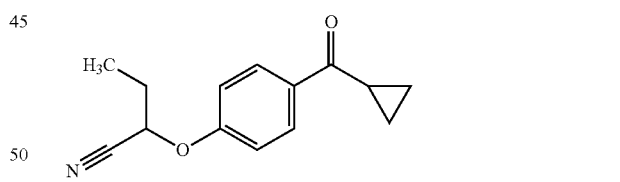

Trifluoroacetic anhydride (3.61 mL, 25.9 mmol) was added to a methylene chloride (130 mL) solution of the compound obtained in Reference Example 86 (6.41 g, 25.9 mmol) and pyridine (4.18 mL, 51.8 mmol) at 0° C., and the mixture was stirred at the same temperature for 30 minutes. Water and a saturated aqueous solution of ammonium chloride were added to the reaction mixture at 0° C., and the mixture was extracted three times with methylene chloride. The organic layer thus obtained was washed with 1 M hydrochloric acid and 1 M aqueous sodium hydroxide solution sequentially, and then dried over anhydrous sodium sulfate. The solvent was distilled off under reduced pressure, and the resulting residue was purified by silica gel column chromatography (hexane:ethyl acetate=9:1→2:1, v/v) to give the title compound (5.81 g, yield: 98%).

¹H-NMR (400 MHz, CDCl₃) δ ppm:
8.05 (2H, d, J=9 Hz), 7.07 (2H, d, J=9 Hz), 4.83 (1H, t, J=6 Hz), 2.67-2.60 (1H, m), 2.19-2.12 (2H, m), 1.28-1.17 (5H, m), 1.06-0.97 (2H, m).

Reference Example 88

(1Z)-2-[4-(Cyclopropylcarbonyl)phenoxy]-N'-hydroxybutanimidamide

[Chemical Formula 115]

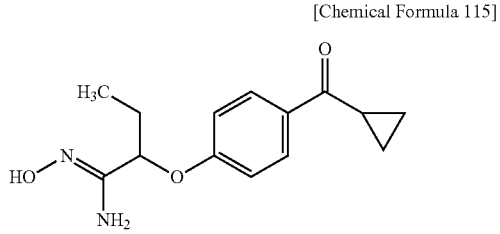 [SMILES: CCC(Oc1ccc(C(=O)C2CC2)cc1)/C(N)=N/O]

A 50% aqueous hydroxylamine solution (3.01 mL, 50.7 mmol) was added to an ethanol (120 mL) solution of the compound obtained in Reference Example 87 (5.81 g, 25.3 mmol) at room temperature, and the mixture was stirred at room temperature for 30 minutes. The solvent was distilled off under reduced pressure to give the title compound (6.61 g, yield: 95%).
¹H-NMR (500 MHz, CDCl₃) δ ppm:
7.98 (2H, d, J=9 Hz), 7.07 (2H, d, J=9 Hz), 4.70 (2H, s), 4.62-4.55 (1H, m), 3.72 (1H, dq, J=7, 6 Hz), 2.64-2.53 (1H, m), 2.08-1.82 (2H, m), 1.23-1.17 (2H, m), 1.09-0.92 (5H, m).

Reference Example 89 tert-Butyl 4-(3-{1-[4-(cyclopropylcarbonyl)phenoxy]propyl}-1,2,4-oxadiazol-5-yl)-2-fluorobenzoate

[Chemical Formula 116]

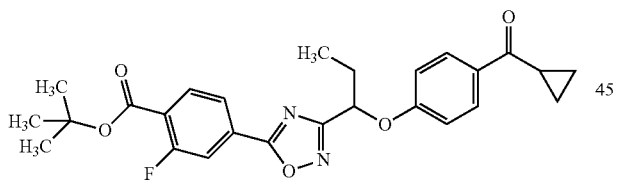

1-Hydroxybenzotriazole monohydrate (255 mg, 1.66 mmol) and N-(3-dimethylaminopropyl)-N'-ethylcarbodiimide hydrochloride (398 mg, 2.08 mmol) were added to an N,N-dimethylformamide (7 mL) solution of the compound obtained in Reference Example 80 (333 mg, 1.38 mmol) at room temperature, and the mixture was stirred at the same temperature for 30 minutes. The compound obtained in Reference Example 89 (363 mg, 1.38 mmol) was added to the mixture at room temperature, and the resulting mixture was stirred at room temperature for 20 minutes, and then heated at 90° C. for 6 hours. After the reaction mixture was cooled to room temperature, water and a saturated aqueous solution of sodium hydrogen carbonate were added to the reaction mixture. The resulting mixture was extracted three times with ethyl acetate, and the organic layer thus obtained was washed with a 10% aqueous solution of sodium chloride, then dried over anhydrous sodium sulfate. The solvent was distilled off under reduced pressure, and the resulting residue was purified by silica gel column chromatography (hexane:ethyl acetate=9:1→1:1, v/v) to give the title compound (330 mg, yield: 51%).
¹H-NMR (400 MHz, CDCl₃) δ ppm:
8.02-7.92 (4H, m), 7.88 (1H, d, J=9 Hz), 7.08 (2H, d, J=9 Hz), 5.46 (1H, t, J=7 Hz), 2.65-2.56 (1H, m), 2.36-2.12 (2H, m), 1.61 (9H, s), 1.23-1.17 (2H, m), 1.11 (3H, t, J=7 Hz), 1.02-0.96 (2H, m).

Reference Example 90

4-(3-{1-[4-(Cyclopropylcarbonyl)phenoxy]propyl}-1,2,4-oxadiazol-5-yl)-2-fluorobenzoic acid

[Chemical Formula 117]

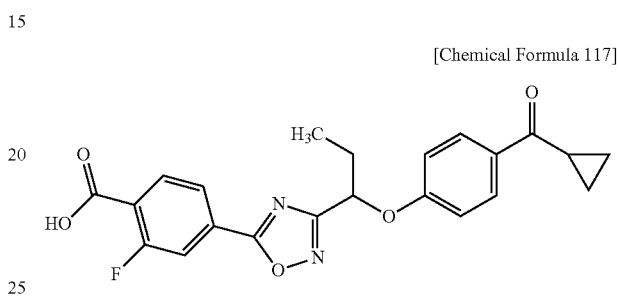

A methylene chloride (1 mL) solution of trifluoroacetic acid (1 mL) was added to a methylene chloride (3 mL) solution of the compound obtained in Reference Example 89 at room temperature, and the mixture was stirred at the same temperature for 30 minutes. Trifluoroacetic acid (1 mL) was added to the mixture at room temperature, and the resulting mixture was stirred at the same temperature for 30 minutes. The solvent was distilled off under reduced pressure, and the resulting residue was purified by silica gel column chromatography (hexane:ethyl acetate=2:1→1:4, v/v) to give the title compound (300 mg, yield: 53%).
¹H-NMR (500 MHz, CDCl₃) δ ppm:
8.17 (1H, dd, J=8, 7 Hz), 8.03-7.92 (4H, m), 7.08 (2H, d, J=9 Hz), 5.47 (1H, t, J=7 Hz), 2.63-2.56 (1H, m), 2.34-2.10 (2H, m), 1.22-1.15 (2H, m), 1.11 (3H, t, J=8 Hz), 1.02-0.95 (2H, m).

Reference Example 91

(4-{1-[5-(4-Amino-3-fluorophenyl)-1,2,4-oxadiazol-3-yl]propyl}phenyl)(cyclopropyl)methanone

[Chemical Formula 118]

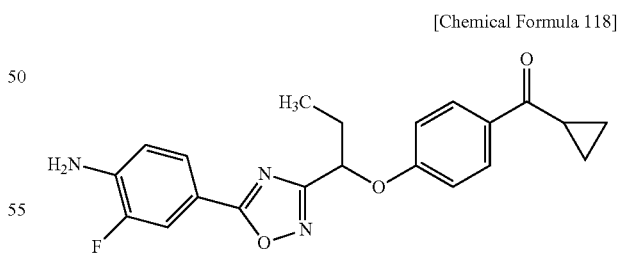

Triethylamine (0.112 mL, 0.804 mmol) and diphenylphosphoryl azide (0.173 mL, 0.804 mmol) were added to a tert-butanol (4 mL) solution of the compound obtained in Reference Example 90 (300 mg, 0.731 mmol) at room temperature, and the mixture was heated at 60° C. for 6 hours. After the reaction mixture was cooled to room temperature, water was added to the reaction mixture, and the resulting mixture was extracted three times with ethyl acetate, and then dried over anhydrous sodium sulfate. The solvent was distilled off under reduced pressure, and the resulting residue was purified by silica gel column chromatography (hexane:ethyl acetate=9:1→1:1, v/v). Subsequently, a methylene chloride (1 mL) solution of trifluoroacetic acid (1 mL) was added to a methylene chloride (2 mL) solution of the compound thus obtained at room temperature, and the mixture was stirred at the same temperature for 30 minutes. Trifluoroacetic acid (1 mL) was added to the mixture at room temperature, and the resulting mixture was stirred at the same temperature for 30 minutes. The solvent was distilled off under reduced pressure, and the resulting residue was purified by silica gel column chromatography (hexane:ethyl acetate=9:1→1:2, v/v) to give the title compound (128 mg, yield: 46%).

$^1$H-NMR (400 MHz, CDCl$_3$) δ ppm:
7.995 (2H, d, J=9 Hz), 7.80-7.73 (2H, m), 7.08 (2H, d, J=9 Hz), 6.82 (1H, t, J=9 Hz), 5.39 (1H, t, J=7 Hz), 4.24 (2H, s), 2.64-2.56 (1H, m), 2.34-2.10 (2H, m), 1.24-1.20 (2H, m), 1.09 (1H, t, J=7 Hz), 1.04-0.96 (2H, m).

Reference Example 92

2-{[6-(Cyclopropylcarbonyl)pyridin-3-yl]propanamide

[Chemical Formula 119]

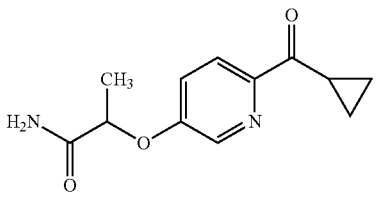

1,1'-Carbonyldiimidazole (788 mg, 4.86 mmol) was added to a tetrahydrofuran (8.0 mL) solution of the compound obtained in Reference Example 75 (953 mg, 4.05 mmol) at 0° C., and the mixture was stirred at the same temperature for 30 minutes. Subsequently, a 28% aqueous ammonia solution (1.0 mL) was added to the mixture, and further the resulting mixture was stirred at the same temperature for 15 minutes. Water was added to the reaction mixture, and the resulting mixture was extracted twice with ethyl acetate. The organic layer thus obtained was washed with brine, and then dried over anhydrous sodium sulfate. The solvent was distilled off under reduced pressure to give the crude title compound (1.09 g).

Reference Example 93

(1Z)-2-{[6-(Cyclopropylcarbonyl)pyridin-3-yl]oxy}-N-hydroxypropanimidamide

[Chemical Formula 120]

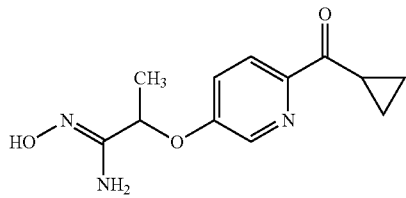

Trifluoroacetic anhydride (676 μL, 4.86 mmol) was added slowly to a dichloromethane (8.0 mL) solution of the compound obtained in Reference Example 92 (1.09 g) and pyridine (786 μL, 9.72 mmol) at 0° C., and the mixture was stirred at the same temperature for 15 minutes, and then further stirred at room temperature for 1.5 hours. Water was added to the reaction mixture, and the resulting mixture was extracted twice with ethyl acetate. The organic layer thus obtained was washed with 0.5 M sulfuric acid and brine, and then dried over anhydrous sodium sulfate. The solvent was distilled off under reduced pressure, and the resulting residue (1.20 g) thus obtained was dissolved in 2-propanol (8.0 mL). A 50% aqueous hydroxylamine solution (401 μL, 6.08 mmol) was added to the mixture at room temperature, and the resulting mixture was stirred at 60° C. for 20 minutes. The solvent was distilled off under reduced pressure to give the crude title compound (1.30 g).

Reference Example 94

4-[3-(1-{[6-(Cyclopropylcarbonyl)pyridin-3-yl]oxy}ethyl)-1,2,4-oxadiazol-5-yl]-2-fluorobenzoic acid

[Chemical Formula 121]

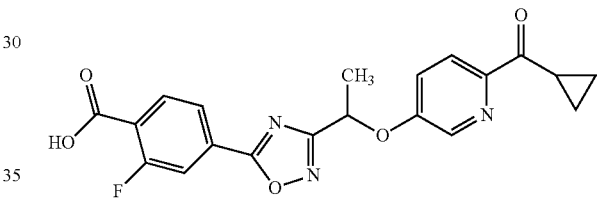

1-Hydroxybenzotriazole monohydrate (675 mg, 4.41 mmol) and N-(3-dimethylaminopropyl)-N'-ethylcarbodiimide hydrochloride (1.54 g, 8.02 mmol) were added to an N,N-dimethylformamide (10 mL) solution of 4-(methoxycarbonyl)-3-fluorobenzoic acid (J. Med. Chem. 2009, 52, 5950-5966.) (794 mg, 4.01 mmol) at room temperature, and the mixture was stirred at the same temperature for 30 minutes. Subsequently, an N,N-dimethylformamide (10 mL) solution of the crude (1Z)-2-{[6-(cyclopropylcarbonyl)pyridin-3-yl]oxy}-N-hydroxypropaneimidamide (999 mg) obtained in Reference Example 93 was added to the mixture, and the resulting mixture was stirred at the same temperature for 15 minutes, and then further stirred at 100° C. for 5 hours. After the reaction mixture was cooled to room temperature, water was added to the reaction mixture, and the resulting mixture was extracted twice with ethyl acetate. The organic layer thus obtained was washed with a saturated aqueous solution of sodium hydrogen carbonate and brine, and then dried over anhydrous sodium sulfate. The solvent was distilled off under reduced pressure, the resulting residue was purified by silica gel column chromatography (hexane:ethyl acetate=95:5→75:25, v/v) to give a compound, and the compound (457 mg, 1.11 mmol) thus obtained was dissolved in tetrahydrofuran (2.0 mL)-methanol (2.0 mL). Subsequently, 1 M aqueous sodium hydroxide solution (2.22 mL, 2.22 mmol) was added to the resulting mixture at room temperature, and the mixture was stirred at the same temperature for 15 minutes. The reaction mixture was concentrated under reduced pressure, then water was added to the reaction mixture, and the aqueous layer was washed with diethyl ether. 1

M Sulfuric acid was added to the resulting mixture to adjust the pH to 6, and then the mixture was extracted twice with ethyl acetate. The organic layer thus obtained was washed with brine, and then dried over anhydrous sodium sulfate. The solvent was distilled off under reduced pressure, and the resulting residue was washed with a hexane-diisopropyl ether (10:1, v/v) mixture to give the title compound (364 mg, yield: 83%).

$^1$H-NMR (400 MHz, CDCl$_3$) δ ppm:
8.48 (1H, d, J=3 Hz), 8.17 (1H, dd, J=8, 7 Hz), 8.02 (1H, d, J=9 Hz), 8.01 (1H, dd, J=8, 2 Hz), 7.95 (1H, dd, J=10, 2 Hz), 7.43 (1H, dd, J=9, 3 Hz), 5.75 (1H, q, J=6.5 Hz), 3.45-3.38 (1H, m), 1.91 (3H, d, J=7 Hz), 1.22-1.17 (2H, m), 1.09-1.03 (2H, m).

Reference Example 95 tert-Butyl 4-[3-(1-{[6-(cyclopropylcarbonyl)pyridin-3-yl]oxy}ethyl)-1,2,4-oxadiazol-5-yl]-2-fluorophenyl}carbamic acid

[Chemical Formula 122]

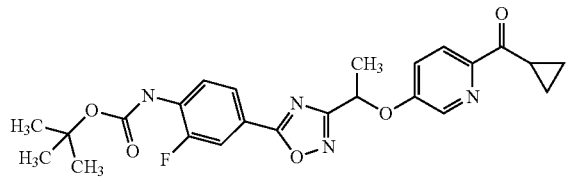

Diphenylphosphoryl azide (84.1 μL, 0.390 mmol) was added to a tert-butanol (1.5 mL) solution of the compound obtained in Reference Example 94 (155 mg, 0.390 mmol) and triethylamine (108 μL, 0.780 mmol) at room temperature, and the mixture was stirred at 90° C. for 3.5 hours. After the reaction mixture was cooled to room temperature, water was added to the reaction mixture, and the resulting mixture was extracted twice with ethyl acetate. The organic layer thus obtained was washed with a saturated aqueous solution of sodium hydrogen carbonate and brine, and then dried over anhydrous sodium sulfate. The solvent was distilled off under reduced pressure, and the resulting residue was purified by silica gel column chromatography (dichloromethane:ethyl acetate=100:0→90:10, v/v) to give the title compound (120 mg, yield: 66%).

$^1$H-NMR (400 MHz, CDCl$_3$) δ ppm:
8.47 (1H, d, J=3 Hz), 8.34 (1H, t, J=8 Hz), 8.00 (1H, d, J=9 Hz), 7.90 (1H, dd, J=8, 2 Hz), 7.83 (1H, dd, J=11, 2 Hz), 7.42 (1H, dd, J=9, 3 Hz), 6.98-6.94 (1H, m), 5.70 (1H, q, J=7 Hz), 3.45-3.39 (1H, m), 1.89 (3H, d, J=7 Hz), 1.54 (9H, s), 1.22-1.17 (2H, m), 1.09-1.03 (2H, m).

Reference Example 96

(5-{1-[5-(4-Amino-3-fluorophenyl)-1,2,4-oxadiazol-3-yl]ethoxy}pyridin-2-yl)(cyclopropyl)methanone

[Chemical Formula 123]

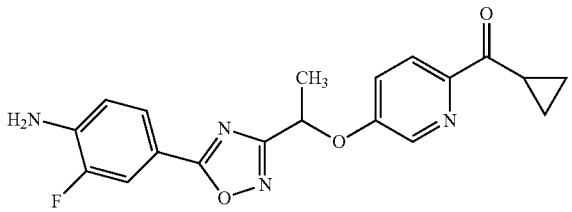

Trifluoroacetic acid (1.0 mL) was added to a dichloromethane (1.0 mL) solution of the compound obtained in Reference Example 95 (118 mg, 0.252 mmol) at room temperature, and the mixture was stirred at the same temperature for 1 hour. The reaction mixture was concentrated under reduced pressure, then a saturated aqueous solution of sodium hydrogen carbonate was added to the reaction mixture, and the resulting mixture was extracted twice with ethyl acetate. The organic layer thus obtained was washed with a saturated aqueous solution of sodium hydrogen carbonate and brine, and then dried over anhydrous sodium sulfate. The solvent was distilled off under reduced pressure, and the resulting residue was purified by silica gel column chromatography (hexane:ethyl acetate=80:20→50:50, v/v) to give the title compound (91.6 mg, yield: 99%).

H-NMR (400 MHz, CDCl$_3$) δ ppm:
8.47 (1H, d, J=3 Hz), 8.00 (1H, d, J=9 Hz), 7.77-7.71 (2H, m), 7.42 (1H, dd, J=9, 3 Hz), 6.82 (1H, t, J=9 Hz), 5.67 (1H, q, J=7 Hz), 4.25 (2H, s), 3.46-3.39 (1H, m), 1.87 (3H, d, J=7 Hz), 1.22-1.17 (2H, m), 1.08-1.03 (2H, m).

Reference Example 97

(2S)-2-(4-Methoxyphenoxy)butanamide

[Chemical Formula 124]

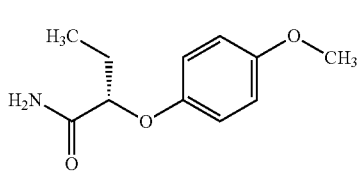

Sodium hydride (3.21 g, ca. 60% in oil, 80.6 mmol) was added to a 1,4-dioxane (100 mL) solution of 4-methoxyphenol (2.50 g, 20.1 mmol) at room temperature, and the mixture was stirred at room temperature for 10 minutes. (2S)-2-Chlorobutyric acid (2.95 g, 24.2 mmol) was added to the mixture at 100° C., and then the resulting mixture was heated at 100° C. for 30 minutes. After the reaction mixture was cooled to room temperature, water and 2 M hydrochloric acid were added to the reaction mixture. The resulting mixture was extracted three times with ethyl acetate, and the organic layer thus obtained was washed with water, and then dried over anhydrous sodium sulfate. The solvent was distilled off under reduced pressure, and thus a mixture containing (2S)-2-(4-methoxyphenoxy)butyric acid was obtained. Carbonyldiimidazole (4.89 g, 30.2 mmol) was added to a tetrahydrofuran (100 mL) solution of the mixture described above, and the resulting mixture was stirred at room temperature for 30 minutes. Subsequently, a 28% aqueous ammonia solution (50 mL, excess amount) was added to the mixture at room temperature, and the resulting mixture was stirred for 20 minutes. Water was added to the reaction mixture, and the resulting mixture was extracted three times with ethyl acetate. The organic layer thus obtained was washed with water, and then dried over anhydrous sodium sulfate. The solvent was distilled off under reduced pressure, and the resulting residue was purified by silica gel column chromatography (hexane:ethyl acetate=4:1-41:4, v/v) to give the title compound (3.66 g, yield: 87%).

$^1$H-NMR (400 MHz, CDCl$_3$) δ ppm:
6.95-6.84 (4H, m), 6.49-6.35 (1H, m), 5.53-5.36 (1H, m), 4.45 (1H, dd, J=7, 4 Hz), 3.80 (3H, s), 2.06-1.90 (2H, m), 1.08 (3H, t, J=7 Hz).

Reference Example 98

(2S)-2-(4-Methoxyphenoxy)butanenitrile

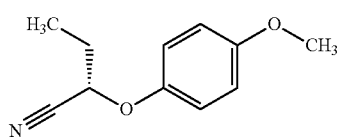

[Chemical Formula 125]

Trifluoroacetic anhydride (0.655 mL, 4.78 mmol) was added to a methylene chloride (5 mL) solution of the compound obtained in Reference Example 97 (1.00 g, 4.78 mmol) and pyridine (0.753 mL, 9.56 mmol) at 0° C., and the mixture was stirred at the same temperature for 20 minutes. After the mixture was stirred at room temperature for 1 hour, the reaction mixture was diluted with diethyl ether, and water and a saturated aqueous solution of ammonium chloride were added to the mixture. The resulting mixture was extracted three times with diethyl ether, and the organic layer thus obtained was washed with 1 M hydrochloric acid, and then dried over anhydrous sodium sulfate. The solvent was distilled off under reduced pressure, and the resulting residue was purified by silica gel column chromatography (hexane:ethyl acetate=9:1→1:1, v/v) to give the title compound (859 mg, yield: 94%).

$^1$H-NMR (500 MHz, CDCl$_3$) δ ppm:

7.01 (2H, d, J=9 Hz), 6.90 (2H, d, J=9 Hz), 4.65 (1H, t, J=7 Hz), 3.82 (3H, s), 2.10 (2H, dq, J=7, 7 Hz), 1.22 (3H, t, J=7 Hz).

Reference Example 99

(1Z,2S)—N'-Hydroxy-2-(4-methoxyphenoxy)butanimidamide

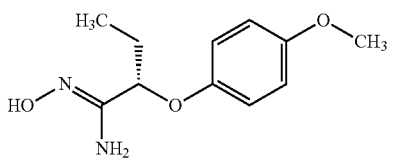

[Chemical Formula 126]

A 50% aqueous hydroxylamine solution (0.788 mL, 13.5 mmol) was added to an ethanol (20 mL) solution of the compound obtained in Reference Example 98 (859 mg, 4.49 mmol) at room temperature, and the mixture was stirred at 70° C. for 2 hours. After the reaction mixture was cooled to room temperature, the solvent was distilled off under reduced pressure to give the title compound (1.15 g, yield: quantitative).

$^1$H-NMR (400 MHz, CDCl$_3$) δ ppm:

6.95 (2H, d, J=9 Hz), 6.83 (2H, d, J=9 Hz), 4.70 (2H, bs), 4.38 (1H, dd, J=7, 6 Hz), 3.77 (3H, s), 2.02-1.80 (2H, m), 1.06 (3H, t, J=7 Hz).

Reference Example 100 tert-Butyl 2-fluoro-4-{3-[(1S)-1-(4-methoxyphenoxy)propyl]-1,2,4-oxadiazol-5-yl}benzoate

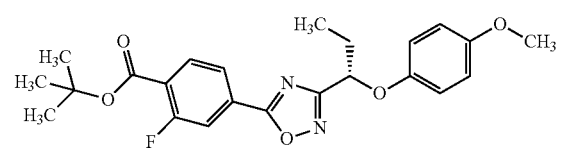

[Chemical Formula 127]

1-Hydroxybenzotriazole monohydrate (320 mg, 2.09 mmol) and N-(3-dimethylaminopropyl)-N'-ethylcarbodiimide hydrochloride (802 mg, 4.18 mmol) were added to an N,N-dimethylformamide (10 mL) solution of the compound obtained in Reference Example 80 (502 mg, 2.09 mmol) at room temperature, and the mixture was stirred at the same temperature for 30 minutes. The compound obtained in Reference Example 99 (469 mg, 2.09 mmol) was added to the mixture at room temperature, and the resulting mixture was stirred at room temperature for 20 minutes, and then heated at 90° C. for 8 hours. After the reaction mixture was cooled to room temperature, water was added to the reaction mixture. The mixture was extracted three times with ethyl acetate, then washed with a saturated aqueous solution of sodium hydrogen carbonate and a 10% aqueous solution of sodium chloride sequentially, and dried over anhydrous sodium sulfate. The solvent was distilled off under reduced pressure, and the resulting residue was purified by silica gel column chromatography (hexane:ethyl acetate=9:1→2:1, v/v) to give the title compound (349 mg, yield: 39%).

$^1$H-NMR (400 MHz, CDCl$_3$) δ ppm:

8.03-7.89 (3H, m), 6.97 (2H, d, J=9 Hz), 6.81 (2H, d, J=9 Hz), 5.25 (1H, dd, J=7, 6 Hz), 3.76 (3H, s), 2.30-2.07 (2H, m), 1.63 (9H, s), 1.10 (3H, t, J=7 Hz).

Reference Example 101 tert-Butyl 2-fluoro-4-{3-[(1S)-1-hydroxypropyl]-1,2,4-oxadiazol-5-yl}benzoate

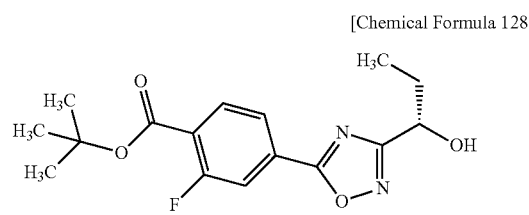

[Chemical Formula 128]

The compound obtained in Reference Example 100 (349 mg, 0.813 mmol) was dissolved in acetonitrile (8 mL) and water (8 mL), then ammonium cerium (IV) nitrate (1.34 g, 2.44 mmol) was added to the mixture at 0° C., and the resulting mixture was stirred at the same temperature for 30 minutes. Water was added to the reaction mixture, and the resulting mixture was extracted three times with diethyl ether. The organic layer thus obtained was washed three times with water, then further washed with a saturated aqueous solution of sodium hydrogen carbonate, and dried over anhydrous sodium sulfate. Methanol was added to the mixture, and the generated insoluble material was removed by filtration. The solvent was distilled off under reduced pressure, and the resulting residue was purified by silica gel column chromatography (hexane:ethyl acetate=9:1→1:2, v/v) to give the title compound (226 mg, yield: 86%).

¹H-NMR (400 MHz, CDCl₃) δ ppm:
8.02 (1H, dd, J=8, 7 Hz), 7.95 (1H, dd, J=8, 2 Hz), 7.89 (1H, dd, J=11, 1 Hz), 4.92-4.86 (1H, m), 2.40-2.32 (1H, m), 2.08-1.95 (2H, m), 1.62 (9H, s), 1.05 (3H, t, J=7 Hz).

Reference Example 102

4-(3-{(1R)-1-[4-(Cyclopropylcarbonyl)phenoxy]propyl}-1,2,4-oxadiazol-5-yl)-2-fluorobenzoic acid

[Chemical Formula 129]

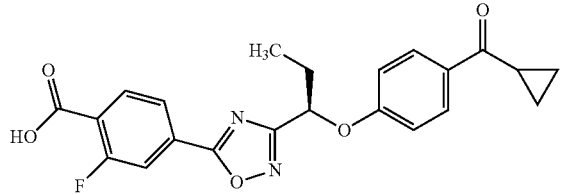

Triphenylphosphine (188 mg, 0.714 mmol) and di-tert-butyl azodicarboxylate (165 mg, 0.714 mmol) were added to a tetrahydrofuran (6 mL) solution of the compound obtained in Reference Example 101 (210 mg, 0.650 mmol) and cyclopropyl(4-hydroxyphenyl)methanone (105 mg, 0.650 mmol) at room temperature, and the mixture was stirred at the same temperature for 30 minutes. The solvent was distilled off under reduced pressure, and the resulting residue was purified by silica gel column chromatography (hexane:ethyl acetate=9:1→1:1, v/v). Subsequently, trifluoroacetic acid (1 mL) was added to a methylene chloride (3 mL) solution of the compound thus obtained at room temperature, and the mixture was stirred at the same temperature for 30 minutes. The solvent was distilled off under reduced pressure, and the resulting residue was purified by silica gel column chromatography (hexane:ethyl acetate=2:1→1:4, v/v) to give the title compound (153 mg, yield: 58%).

¹H-NMR (400 MHz, CDCl₃) δ ppm:
8.20-8.13 (1H, m), 8.04-7.92 (4H, m), 7.08 (2H, d, J=8 Hz), 5.50-5.44 (1H, m), 2.85-2.55 (1H, m), 2.38-2.10 (2H, m), 1.22-1.16 (2H, m), 1.11 (3H, t, J=7 Hz), 1.04-0.96 (2H, m).

Reference Example 103

4-[5-(Trifluoromethyl)-1,2,4-oxadiazol-3-yl]phenol

[Chemical Formula 130]

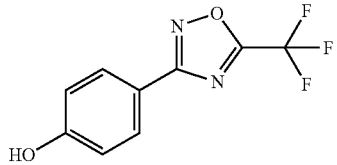

Pyridine (15.9 mL, 197 mmol) and trifluoroacetic anhydride (10.1 mL, 72.6 mmol) were added to an N,N-dimethylformamide (100 mL) solution of N',4-dihydroxybenzenecarboxyimidamide (WO 2011/016469) (10.0 g, 65.7 mmol) at 0° C., and the mixture was stirred at 0° C. for 15 minutes. After that, the mixture was heated to 80° C., and stirred for 2 hours. After the reaction mixture was cooled to room temperature, water and 2 M hydrochloric acid were added to the reaction mixture, and the resulting mixture was extracted twice with ethyl acetate. The organic layer thus obtained was washed with a 10% aqueous solution of sodium chloride, and then dried over anhydrous sodium sulfate. The solvent was distilled off under reduced pressure. The resulting residue was purified by silica gel column chromatography (hexane:ethyl acetate=95:5, v/v), and then washed with hexane to give the title compound (15.0 g, yield: 99%).

¹H-NMR (400 MHz, CDCl₃) δ ppm:
8.02 (2H, d, J=9 Hz), 6.96 (2H, d, J=9 Hz), 5.39 (1H, br s).

Reference Example 104

4-[3-(Trifluoromethyl)-1,2,4-oxadiazol-5-yl]phenol

[Chemical Formula 131]

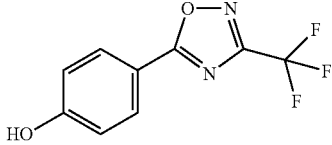

Potassium tert-butoxide (4.48 g, 40.0 mmol) was added to an N,N-dimethylformamide (20 mL) solution of hydroxylamine hydrochloride (2.78 g, 40.0 mmol) at room temperature, and the mixture was stirred for 15 minutes. The compound obtained in Reference Example 103 (2.30 g, 10.0 mmol) was added to the mixture at room temperature, and the mixture was stirred at the same temperature for 2.5 hours. Water and a 10% aqueous solution of sodium chloride were added to the reaction mixture, and the resulting mixture was extracted three times with ethyl acetate, and then dried over anhydrous sodium sulfate. The solvent was distilled off under reduced pressure, and the resulting residue was purified by silica gel column chromatography (hexane:ethyl acetate=4:1→1:4, v/v) to give the title compound (1.35 g, yield: 59%).

¹H-NMR (400 MHz, CDCl₃) δ ppm:
8.02 (2H, m), 7.02 (2H, d, J=9 Hz).

Reference Example 105

(1R)—N-Benzyl-1-[(2R)-1,4-dioxaspiro[4,5]deca-4-yl]ethanamine

[Chemical Formula 132]

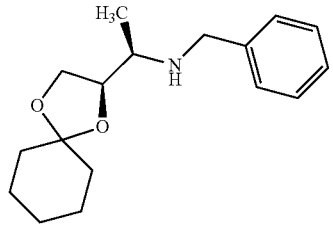

A toluene (100 mL) solution of anhydrous sodium sulfate (38.2 g, 269 mmol) and benzylamine (19.2 g, 179 mmol) were added to a toluene (100 mL) solution of 2,3-O-cyclohexylidene-L-glyceraldehyde (J. Org. Chem., 2005, 70, 6346-6352.) (30.5 g, 179 mmol) at room temperature, and the mixture was stirred at the same temperature for 1 hour, and then left to stand at the same temperature overnight. The resulting insoluble material was removed by filtration through a cotton plug, and then the solvent was distilled off under reduced pressure to give a crude product (49.2 g). The crude product was dissolved in tetrahydrofuran (400 mL), then boron trifluoride-diethyl ether complex (22.5 mL, 179 mmol) was added to the mixture at −78° C., and the resulting mixture was stirred at the same temperature for 10 minutes. Subsequently, 3.0 M methylmagnesium bromide-diethyl ether solution (89.6 mL, 269 mmol) was added to the mixture at −78° C. over 30 minutes, and then the resulting mixture was heated to 0° C. over 5 hours or more. The reaction mixture was poured into a saturated aqueous solution of sodium hydrogen carbonate (300 mL), and then the mixture was stirred at room temperature for 3 minutes. Subsequently, the insoluble material was removed by filtration through Celite. The solvent was distilled off under reduced pressure, and then the mixture was extracted twice with ethyl acetate. The organic layer thus obtained was washed with brine, and then dried over anhydrous sodium sulfate. The solvent was distilled off under reduced pressure, and the resulting residue was purified by silica gel column chromatography (hexane:diethyl ether=2:1, v/v) to give the title compound (37.8 g, yield: 77%).

$^1$H-NMR (400 MHz, CDCl$_3$) δ ppm:
7.37-7.29 (4H, m), 7.28-7.21 (1H, m), 4.05-3.98 (2H, m), 3.93-3.85 (2H, m), 3.74 (1H, d, J=13 Hz), 2.89-2.80 (1H, m), 1.71-1.29 (10H, m), 1.10 (3H, d, J=6 Hz).

Reference Example 106

(1R)-1-[(2R)-1,4-Dioxaspiro[4,5]deca-4-yl]ethanamine

[Chemical Formula 133]

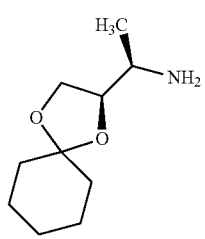

20% Palladium hydroxide on carbon (1.89 g) was added to an ethanol (300 mL) solution of the compound obtained in Reference Example 105 (37.8 g, 137 mmol) at room temperature, and the mixture was stirred at 60° C. for 2.5 hours in a hydrogen atmosphere. After the reaction mixture was cooled to room temperature, the insoluble material was removed by filtration through Celite. The solvent was distilled off under reduced pressure to give the title compound (26.7 g).

$^1$H-NMR (400 MHz, CDCl$_3$) δ ppm:
3.99 (1H, dd, J=7, 6 Hz), 3.93 (1H, td, J=6, 5 Hz), 3.80 (1H, dd, J=7, 6 Hz), 3.07 (1H, qd, J=7, 5 Hz), 1.67-1.30 (10H, m), 1.07 (3H, dd, J=7 Hz).

Example 1

4-{4-[(1R)-1-{[6-(Cyclopropylcarbonyl)pyridin-3-yl]oxy}ethyl]-2H-1,2,3-triazol-2-yl}-N-[(1R,2R)-2,3-dihydroxy-1-methylpropyl]-2-fluorobenzamide

[Chemical Formula 134]

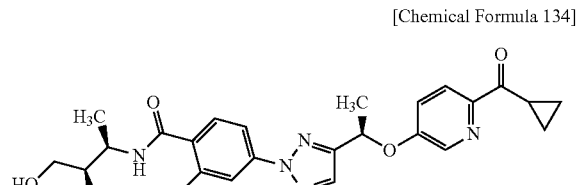

An N,N-dimethylformamide (2.2 mL) solution of the (1R)-1-[(2R)-1,4-dioxaspiro[4.5]deca-2-yl]ethanamine (206 mg, 1.11 mmol) obtained in Reference Example 106 was added to an N,N-dimethylformamide (4.4 mL) solution of the compound obtained in Reference Example 26 (220 mg, 0.555 mmol), N-(3-dimethylaminopropyl)-N'-ethylcarbodiimide hydrochloride (213 mg, 1.11 mmol), and 1-hydroxybenzotriazole monohydrate (85.0 mg, 0.555 mmol) at room temperature, and the mixture was stirred at the same temperature for 22.5 hours. Water was added to the reaction mixture, and the resulting mixture was extracted with ethyl acetate. The organic layer thus obtained was washed with water, and then dried over anhydrous sodium sulfate. The solvent was distilled off under reduced pressure, and the resulting residue was purified by silica gel column chromatography (33% ethyl acetate/hexane) to give 4-{4-[(1R)-1-{[6-(cyclopropylcarbonyl)pyridin-3-yl]oxy}ethyl]-2H-1,2,3-triazol-2-yl}-N-{(1R)-1-[(2R)-1,4-dioxaspiro[4.5]deca-2-yl]ethyl}-2-fluorobenzamide (308 mg, yield: 99%).

Acetic acid (4.8 mL) and water (1.2 mL) were added to the compound described above (306 mg, 0.543 mmol), and the mixture was stirred at 80° C. for 135 minutes. The mixture was returned to room temperature, and the solvent in the reaction mixture was distilled off under reduced pressure. A saturated aqueous solution of sodium hydrogen carbonate and water were added to the resulting residue, and the mixture was extracted with dichloromethane. The organic layer thus obtained was dried over anhydrous sodium sulfate. The resulting mixture was filtered, then solvent was distilled off under reduced pressure, and the resulting residue was purified by silica gel column chromatography (66%-99% ethyl acetate/hexane) to give the title compound (147 mg, yield: 56%).

$^1$H-NMR (400 MHz, CDCl$_3$) δ ppm:
8.42 (1H, d, J=2.7 Hz), 8.24-8.20 (1H, m), 8.01-7.97 (2H, m), 7.89-7.85 (1H, m), 7.83 (1H, s), 7.37-7.34 (1H, m), 6.88-6.83 (1H, m), 5.81-5.76 (1H, m), 4.26-4.21 (1H, m), 3.73-3.65 (2H, m), 3.51-3.47 (1H, m), 3.44-3.38 (1H, m), 3.23-3.19 (1H, m), 2.83-2.81 (1H, m), 1.84 (3H, d, J=6.3 Hz), 1.42 (3H, d, J=7.0 Hz), 1.22-1.18 (2H, m), 1.08-1.03 (2H, m);
MS (ES) m/z: 484 [M+H]$^+$.

Example 2

1-[4-(4-{1-[4-(Cyclopropylcarbonyl)phenoxy]propyl}-2H-1,2,3-triazol-2-yl)-2-fluorophenyl]-3-(2-hydroxyethyl)urea

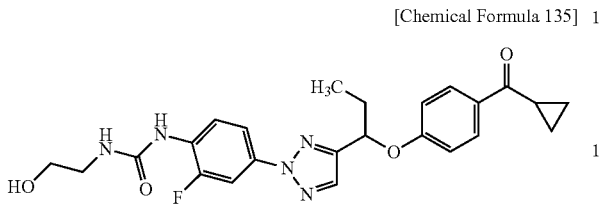

Triphosgene (78.0 mg, 0.263 mmol) was added to a tetrahydrofuran (4 mL) solution of the compound obtained in Reference Example 27 (200 mg, 0.526 mmol) and N,N-diisopropylethylamine (0.179 mL, 1.05 mmol) at room temperature. The mixture was stirred at room temperature for 5 minutes, and then 2-aminoethanol (63.0 μL, 1.05 mmol) was added to the mixture. After the resulting mixture was stirred at room temperature for 30 minutes, water was added to the reaction mixture, and the resulting mixture was extracted with ethyl acetate. The organic layer thus obtained was dried over anhydrous sodium sulfate. The solvent was distilled off under reduced pressure, and the resulting residue was purified by silica gel column chromatography (66%-99% ethyl acetate/hexane) to give the title compound (188 mg, yield: 77%).

$^1$H-NMR (400 MHz, CDCl$_3$) δ ppm:
8.23-8.19 (1H, m), 7.95 (2H, d, J=8.6 Hz), 7.80-7.75 (2H, m), 7.67 (1H, s), 7.09 (1H, br s), 7.01 (2H, d, J=9.0 Hz), 5.52-5.46 (2H, m), 3.81-3.78 (2H, m), 3.48-3.44 (2H, m), 2.63-2.56 (2H, m), 2.22-2.02 (2H, m), 1.19-1.16 (2H, m), 1.09-1.05 (3H, m), 0.99-0.97 (2H, m);

MS (ES) m/z: 468 [M+H]$^+$.

Example 3

1-(4-{4-[(1R)-1-{[6-(Cyclopropylcarbonyl)pyridin-3-yl]oxy}ethyl]-2H-1,2,3-triazol-2-yl}-2-fluorophenyl)-3-(2-hydroxyethyl)urea

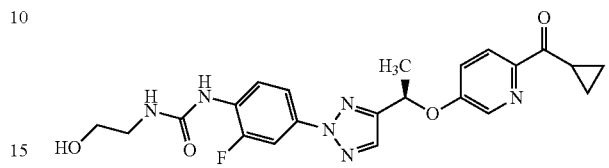

Triphosgene (75.9 mg, 0.256 mmol) was added to a tetrahydrofuran (5 mL) solution of the compound obtained in Reference Example 28 (188 mg, 0.512 mmol) and N,N-diisopropylethylamine (0.174 mL, 1.02 mmol) at room temperature. The mixture was stirred at room temperature for 5 minutes, and then 2-aminoethanol (61.3 μL, 1.02 mmol) was added to the mixture. The resulting mixture was stirred at room temperature for 4 hours, then water was added to the reaction mixture, and the resulting mixture was extracted with ethyl acetate. The organic layer thus obtained was dried over anhydrous sodium sulfate. The solvent was distilled off under reduced pressure, and the resulting residue was purified by silica gel column chromatography (66%-99% ethyl acetate/hexane) to give the title compound (79.1 mg, yield: 34%).

$^1$H-NMR (400 MHz, CDCl$_3$) δ ppm:
8.42 (1H, d, J=2.7 Hz), 8.25-8.21 (1H, m), 7.99 (1H, d, J=8.6 Hz), 7.82-7.76 (2H, m), 7.74 (1H, s), 7.38-7.35 (1H, m), 6.89 (1H, br s), 5.79-5.74 (1H, m), 5.28-5.24 (1H, m), 3.82-3.80 (2H, m), 3.50-3.46 (2H, m), 3.44-3.38 (1H, m), 2.35 (1H, m), 1.83 (3H, d, J=6.7 Hz), 1.21-1.18 (2H, m), 1.08-1.03 (2H, m);

MS (ES) m/z: 455 [M+H]$^+$.

By using a compound obtained in a Reference Example or a compound obtained in an Example, the compounds in the following Tables were obtained by reference to the above Examples.

TABLE 1

| Example | Compound name | Structural formula | NMR |
|---|---|---|---|
| 4 | 4-(4-{1-[4-(Cyclopropylcarbonyl)phenoxy]propyl}-2H-1,2,3-triazol-2-yl)-2-fluoro-N-[(1R)-2-hydroxy-1-methylethyl]benzamide | | $^1$H-NMR (400 MHz, CDCl$_3$) δ ppm: 8.25-8.21 (1H, m), 7.99-7.95 (3H, m), 7.87-7.84 (1H, m), 7.76 (1H, s), 7.02-7.00 (2H, m), 6.91-6.86 (1H, m), 5.52-5.49 (1H, m), 4.34 (1H, m), 3.84-3.79 (1H, m), 3.71-3.66 (1H, m), 2.62-2.53 (2H, m), 2.21-2.06 (2H, m), 1.33 (3H, d, J = 7.0 Hz), 1.20-1.17 (2H, m), 1.10-1.07 (3H, m), 0.99-0.97 (2H, m). MS (FAB) m/z: 467 [M + H]$^+$. |

TABLE 1-continued

| Example | Compound name | Structural formula | NMR |
|---|---|---|---|
| 5 | 4-(4-{1-[4-(Cyclopropyl-carbonyl)phenoxy]propyl}-2H-1,2,3-triazol-2-yl)-2-fluoro-N-[(3S)-2-oxopyrrolidin-3-yl]benzamide | | ¹H-NMR (400 MHz, CDCl₃) δ ppm: 8.25-8.20 (1H, m), 7.99-7.94 (3H, m), 7.89-7.85 (1H, m), 7.76 (1H, s), 7.31-7.26 (1H, m), 7.02-6.99 (2H, m), 5.87 (1H, m), 5.52-5.49 (1H, m), 4.62-4.56 (1H, m), 3.50-3.46 (2H, m), 2.97-2.90 (1H, m), 2.62-2.56 (1H, m), 2.23-2.04 (3H, m), 1.21-1.17 (2H, m), 1.10-1.07 (3H, m), 1.00-0.96 (2H, m); MS (ES) m/z: 492 [M + H]⁺. |
| 6 | 4-(4-{1-[4-(Cyclopropyl-carbonyl)phenoxy]ethyl}-2H-1,2,3-triazol-2-yl)-2-fluoro-N-[(1R)-2-hydroxy-1-methylethyl]benzamide | | ¹H-NMR (400 MHz, CDCl₃) δ ppm: 8.25-8.21 (1H, m), 7.99-7.96 (3H, m), 7.87-7.84 (1H, m), 7.80 (1H, s), 7.03-7.01 (2H, m), 6.92-6.87 (1H, m), 5.78-5.73 (1H, m), 4.35 (1H, m), 3.84-3.79 (1H, m), 3.71-3.66 (1H, m), 2.62-2.57 (2H, m), 1.80 (3H, d, J = 6.3 Hz), 1.33 (3H, d, J = 6.6 Hz), 1.20-1.18 (2H, m), 1.00-0.97 (2H, m); MS (FAB) m/z: 453 [M + H]⁺. |
| 7 | 4-(4-{(1R)-1-[4-(Cyclopropyl-carbonyl)phenoxy]propyl}-2H-1,2,3-triazol-2-yl)-2-fluoro-N-[(1R)-2-hydroxy-1-methylethyl]benzamide | | ¹H-NMR (400 MHz, CDCl₃) δ ppm: 8.25-8.21 (1H, m), 7.99-7.95 (3H, m), 7.87-7.84 (1H, m), 7.76 (1H, s), 7.02-7.00 (2H, m), 6.91-6.86 (1H, m), 5.52-5.49 (1H, m), 4.34 (1H, m), 3.84-3.79 (1H, m), 3.71-3.66 (1H, m), 2.62-2.53 (2H, m), 2.21-2.06 (2H, m), 1.33 (3H, d, J = 6.7 Hz), 1.20-1.17 (2H, m), 1.10-1.07 (3H, m), 0.99-0.97 (2H, m); MS (ES) m/z: 467 [M + H]⁺. |

TABLE 2

| Example | Compound name | Structural formula | NMR |
|---|---|---|---|
| 8 | 4-{4-[(1R)-1-{[6-(Cyclopropylcarbonyl)pyridin-3-yl]oxy}ethyl]-2H-1,2,3-triazol-2-yl}-2-fluoro-N-[(1R)-2-hydroxy-1-methylethyl]benzamide | | ¹H-NMR (400 MHz, CDCl₃) δ ppm: 8.43 (1H, d, J = 2.3 Hz), 8.25-8.21 (1H, m), 8.01-7.96 (2H, m), 7.87-7.84 (1H, m), 7.83 (1H, s), 7.37-7.34 (1H, m), 6.91-6.87 (1H, m), 5.81-5.76 (1H, m), 4.37-4.32 (1H, m), 3.83-3.80 (1H, m), 3.71-3.66 (1H, m), 3.44-3.38 (1H, m), 2.55 (1H, m), 1.84 (3H, d, J = 6.7 Hz), 1.33 (3H, d, J = 6.7 Hz), 1.23-1.18 (2H, m), 1.08-1.04 (2H, m); MS (ES) m/z: 454 [M + H]⁺. |
| 9 | 4-{4-[(1R)-1-{[6-(Cyclopropylcarbonyl)pyridin-3-yl]oxy}ethyl]-2H-1,2,3-triazol-2-yl}-N-[(2S)-2,3-dihydroxypropyl]-2-fluorobenzamide | | ¹H-NMR (400 MHz, CDCl₃) δ ppm: 8.43 (1H, d, J = 2.3 Hz), 8.26-8.21 (1H, m), 8.01-7.97 (2H, m), 7.89-7.86 (1H, m), 7.83 (1H, s), 7.37-7.34 (1H, m), 7.21-7.15 (1H, m), 5.81-5.76 (1H, m), 3.95-3.91 (1H, m), 3.75-3.61 (4H, m), 3.44-3.38 (1H, m), 2.94-2.93 (1H, m), 2.79-2.76 (1H, m), 1.84 (3H, d, J = 6.7 Hz), 1.22-1.18 (2H, m), 1.08-1.04 (2H, m); MS (ES) m/z: 470 [M + H]⁺. |
| 10 | 4-{4-[(1R)-1-{[6-(Cyclopropylcarbonyl)pyridin-3-yl]oxy}ethyl]-2H-1,2,3-triazol-2-yl}-2-fluoro-N-[(3S)-2-oxopyrrolidin-3-yl]benzamide | | ¹H-NMR (400 MHz, CDCl₃) δ ppm: 8.43 (1H, d, J = 2.7 Hz), 8.25-8.21 (1H, m), 8.01-7.96 (2H, m), 7.89-7.85 (1H, m), 7.83 (1H, s), 7.37-7.34 (1H, m), 7.30-7.26 (5H, m), 5.83-5.76 (2H, m), 4.62-4.56 (1H, m), 3.50-3.38 (3H, m), 2.97-2.90 (1H, m), 2.18-2.07 (1H, m), 1.84 (3H, d, J = 6.7 Hz), 1.23-1.18 (2H, m), 1.08-1.04 (2H, m); MS (ES) m/z: 479 [M + H]⁺. |

TABLE 2-continued

| Example | Compound name | Structural formula | NMR |
|---|---|---|---|
| 11 | 1-[4-(4-{1-[4-(Cyclopropylcarbonyl)phenoxy]propyl}-2H-1,2,3-triazol-2-yl)-2-fluorophenyl]urea | | $^{1}$H-NMR (400 MHz, CDCl$_3$) δ ppm: 8.24-8.20 (1H, m), 7.97-7.94 (2H, m), 7.83-7.78 (2H, m), 7.69 (1H, s), 7.03-6.99 (2H, m), 6.78-6.77 (1H, m), 5.50-5.47 (1H, m), 4.79 (2H, s), 2.63-2.56 (1H, m), 2.20-2.04 (2H, m), 1.20-1.17 (2H, m), 1.09-1.06 (3H, m), 1.00-0.96 (2H, m); MS (ES) m/z: 424 [M + H]$^{+}$. |

Example 12

4-(5-{1-[4-(Cyclopropylcarbonyl)phenoxy]propyl}-2H-tetrazol-2-yl)-2-fluoro-N-[(1R)-2-hydroxy-1-methylethyl]benzamide

[Chemical Formula 137]

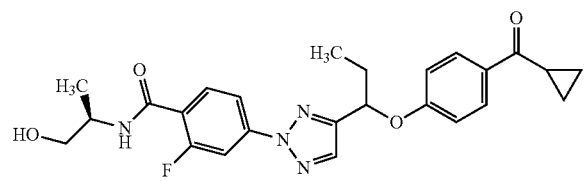

D-Alaninol (82.6 μL, 1.07 mmol) was added to an N,N-dimethylformamide (6 mL) solution of the compound obtained in Reference Example 35 (292 mg, 0.712 mmol), N-(3-dimethylaminopropyl)-N'-ethylcarbodiimide hydrochloride (273 mg, 1.42 mmol), and 1-hydroxybenzotriazole monohydrate (109 mg, 0.712 mmol) at room temperature, and the mixture was stirred at the same temperature for 17 hours. Water was added to the reaction mixture, and the resulting mixture was extracted with ethyl acetate. The organic layer thus obtained was washed with water, and then dried over anhydrous sodium sulfate. The solvent was distilled off under reduced pressure, and the resulting residue was purified by silica gel column chromatography (66% ethyl acetate/hexane) to give the title compound (221 mg, yield: 66%).

$^{1}$H-NMR (400 MHz, CDCl$_3$) δ ppm:
8.32-8.28 (1H, m), 8.08-8.05 (1H, m), 7.99-7.93 (3H, m), 7.09-7.05 (2H, m), 6.92-6.87 (1H, m), 5.67-5.64 (1H, m), 4.35 (1H, m), 3.85-3.80 (1H, m), 3.72-3.66 (1H, m), 2.62-2.56 (1H, m), 2.39-2.19 (3H, m), 1.33 (3H, d, J=6.6 Hz), 1.20-1.16 (2H, m), 1.13-1.09 (3H, m), 1.01-0.96 (2H, m);
MS (FAB) m/z: 468 [M+H]$^{+}$.

By using a compound obtained in a Reference Example or a compound obtained in an Example, the compounds in the following Tables were obtained by reference to the above Examples.

TABLE 3

| Example | Compound name | Structural formula | NMR |
|---|---|---|---|
| 13 | N-Cyclopropyl-4-(5-{1-[4-(cyclopropylcarbonyl)phenoxy]propyl}-2H-tetrazol-2-yl)-2-fluorobenzamide | | $^{1}$H-NMR (400 MHz, CDCl$_3$) δ ppm: 8.34-8.30 (1H, m), 8.07-8.04 (1H, m), 7.98-7.91 (3H, m), 7.08-7.05 (2H, m), 6.82-6.79 (1H, m), 5.66-5.63 (1H, m), 3.00-2.93 (1H, m), 2.62-2.55 (1H, m), 2.40-2.19 (2H, m), 1.20-1.16 (2H, m), 1.13-1.09 (3H, m), 1.00-0.96 (2H, m), 0.94-0.89 (2H, m), 0.68-0.64 (2H, m); MS (ES) m/z: 450 [M + H]$^{+}$. |

TABLE 3-continued

| Example | Compound name | Structural formula | NMR |
|---|---|---|---|
| 14 | N-Cyclopropyl-4-[5-(1-{[6-(cyclopropylcarbonyl)pyridin-3-yl]oxy}ethyl)-2H-tetrazol-2-yl]-2-fluorobenzamide | | $^1$H-NMR (400 MHz, CDCl$_3$) δ ppm: 8.46-8.46 (1H, m), 8.35-8.31 (1H, m), 8.07-7.91 (3H, m), 7.44-7.42 (1H, m), 6.83-6.80 (1H, m), 5.95-5.90 (1H, m), 3.41 (1H, m), 2.96 (1H, m), 1.96 (3H, d, J = 6.6 Hz), 1.19-1.18 (2H, m), 1.07-1.05 (2H, m), 0.93-0.91 (2H, m), 0.67-0.66 (2H, m); MS (ES) m/z: 437 [M + H]$^+$. |

Example 15

4-(5-{1-[4-(Cyclopropylcarbonyl)phenoxy]ethyl}-1,3-thiazol-2-yl)-2-fluoro-N-[(1R)-2-hydroxy-1-methylethyl]benzamide

[Chemical Formula 138]

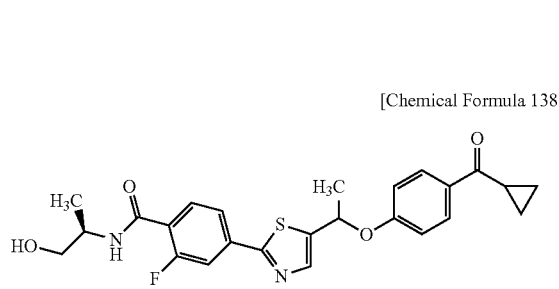 [SMILES: CC(Oc1ccc(C(=O)C2CC2)cc1)c1cnc(-c2ccc(C(=O)N[C@H](C)CO)c(F)c2)s1]

D-Alaninol (0.123 mL, 1.59 mmol) was added to an N,N-dimethylformamide (8.7 mL) solution of the compound obtained in Reference Example 44 (435 mg, 1.06 mmol), N-(3-dimethylaminopropyl)-N'-ethylcarbodiimide hydrochloride (405 mg, 2.11 mmol), and 1-hydroxybenzotriazole monohydrate (162 mg, 1.06 mmol) at room temperature, and the mixture was stirred at the same temperature for 17 hours. Water was added to the reaction mixture, and the resulting mixture was extracted with ethyl acetate. The organic layer thus obtained was washed with water, and then dried over anhydrous sodium sulfate. The solvent was distilled off under reduced pressure, and the resulting residue was purified by silica gel column chromatography (ethyl acetate) to give the title compound (372 mg, yield: 75%).

$^1$H-NMR (400 MHz, CDCl$_3$) δ ppm:

8.16-8.12 (1H, m), 8.00-7.97 (2H, m), 7.81 (1H, s), 7.74 (1H, s), 7.72-7.71 (1H, m), 7.02-6.98 (2H, m), 6.93-6.88 (1H, m), 5.81-5.77 (1H, m), 4.35-4.31 (1H, m), 3.83-3.78 (1H, m), 3.70-3.65 (1H, m), 2.63-2.56 (2H, m), 1.83 (3H, d, J=6.6 Hz), 1.31 (3H, d, J=7.0 Hz), 1.21-1.18 (2H, m), 1.02-0.97 (2H, m).

MS (ES) m/z: 469 [M+H]$^+$.

Example 16

4-[5-(1-{[6-(Cyclopropylcarbonyl)pyridin-3-yl]oxy}ethyl)-1,3-thiazol-2-yl]-2-fluoro-N-[(1R)-2-hydroxy-1-methylethyl]benzamide

[Chemical Formula 139]

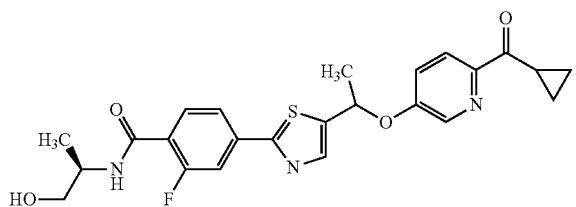 [SMILES: CC(Oc1ccc(C(=O)C2CC2)cc1)c1noc(-c2ccc(C(=O)N[C@H](C)CO)c(F)c2)n1]

A 1 M aqueous sodium hydroxide solution (2.0 mL) was added to a tetrahydrofuran (2.0 mL)-methanol (2.0 mL) solution of the compound obtained in Reference Example 45 (77.3 mg, 0.181 mmol) at room temperature, and the mixture was stirred at the same temperature for 15 minutes. Water was added to the reaction mixture, subsequently, 1 M sulfuric acid was added to the reaction mixture to adjust the pH to 4, and then the resulting mixture was extracted twice with ethyl acetate. The organic layer thus obtained was washed with brine, and then dried over anhydrous sodium sulfate. The solvent was distilled off under reduced pressure, and the resulting residue (83.9 mg) thus obtained was dissolved in N,N-dimethylformamide (1.0 mL). 1-Hydroxybenzotriazole monohydrate (33.3 mg, 0.218 mmol) and N-(3-dimethylaminopropyl)-N'-ethylcarbodiimide hydrochloride (41.7 mg, 0.218 mmol) were added to the mixture at room temperature, and the resulting mixture was stirred at the same temperature for 30 minutes. Subsequently, a N,N-dimethylformamide (1.0 mL) solution of (R)-2-amino-1-propanol (40.8 mg, 0.544 mmol) was added to the resulting mixture at 0° C., and the mixture was stirred at the same temperature for 1 hour, and then further stirred at room temperature for 16 hours. Water was added to the reaction mixture, and the resulting mixture was extracted twice with ethyl acetate. The organic layer thus obtained was washed with a saturated aqueous solution of sodium hydrogen carbonate and brine, and then dried over anhydrous sodium sulfate. The solvent was distilled off under reduced pressure, and the resulting residue was purified by silica gel column chromatography (hexane:ethyl acetate=50:50→0:100, v/v) to give the title compound (74.6 mg, yield: 88%).

¹H-NMR (400 MHz, CDCl₃) δ ppm:
8.40 (1H, d, J=3 Hz), 8.15 (1H, t, J=8 Hz), 8.00 (1H, d, J=9 Hz), 7.83 (1H, s), 7.75-7.71 (2H, m), 7.32 (1H, dd, J=9, 3 Hz), 6.93-6.85 (1H, m), 5.82 (1H, q, J=6 Hz), 4.38-4.29 (1H, m), 3.83-3.77 (1H, m), 3.71-3.64 (1H, m), 3.45-3.37 (1H, m), 2.53 (1H, t, J=6 Hz), 1.86 (3H, d, J=6 Hz), 1.32 (3H, d, J=7 Hz), 1.22-1.17 (2H, m), 1.09-1.03 (2H, m);

MS (ES) m/z: 470 [M+H]⁺.

Example 17

5-Isopropyl-3-[4-(1-{2-[4-(methylsulfonyl)phenyl]-1,3-thiazol-5-yl}propoxy)phenyl]-1,2,4-oxadiazol

[Chemical Formula 140]

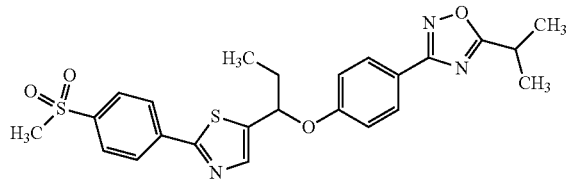

Triphenylphosphine (523 mg, 1.99 mmol) and di-tert-butyl azodicarboxylate (459 mg, 1.99 mmol) were added to a tetrahydrofuran (10 mL) solution of the compound obtained in Reference Example 47 (529 mg, 1.99 mmol) and 4-(5-isopropyl-1,2,4-oxadiazol-3-yl)phenol (WO 2011/016470) (407 mg, 1.99 mmol) at room temperature, and the mixture was stirred at the same temperature for 1 hour. Subsequently, a 4 M hydrogen chloride-1,4-dioxane solution (5.0 mL) was added to the resulting mixture, and the mixture was stirred at the same temperature for 18 hours. Water was added to the reaction mixture, and the resulting mixture was extracted twice with ethyl acetate. The organic layer thus obtained was washed with brine, and then dried over anhydrous sodium sulfate. The solvent was distilled off under reduced pressure, then the resulting residue was purified by silica gel column chromatography (hexane:ethyl acetate=90:10→60:40, v/v) to give a compound, and the compound (684 mg) thus obtained was dissolved in dichloromethane (14 mL). Subsequently, m-chloroperbenzoic acid (762 mg, 2.87 mmol) was added to the resulting mixture at 0° C. The mixture was stirred at the same temperature for 15 minutes, and then further stirred at room temperature for 12 hours. A saturated aqueous solution of sodium hydrogen carbonate was added to the reaction mixture, and the resulting mixture was extracted twice with dichloromethane. The organic layer thus obtained was washed with 1.5 M aqueous sodium sulfite solution, and then dried over anhydrous sodium sulfate. The solvent was distilled off under reduced pressure, and the resulting residue was purified by silica gel column chromatography (hexane:ethyl acetate=75:25→50:50, v/v) to give the title compound (389 mg, yield: 40%).

¹H-NMR (500 MHz, CDCl₃) δ ppm:
8.09 (2H, d, J=8 Hz), 7.99 (2H, d, J=8 Hz), 7.97 (2H, d, J=9 Hz), 7.82 (1H, s), 7.02 (2H, d, J=9 Hz), 5.49 (1H, dd, J=7, 6 Hz), 3.28-3.22 (1H, m), 3.07 (3H, s), 2.26-2.17 (1H, m), 2.09-2.00 (1H, m), 1.43 (6H, d, J=7 Hz), 1.09 (3H, t, J=7 Hz).

MS (ES) m/z: 484 [M+H]⁺.

Example 18

4-[4-(1-{[6-(Cyclopropylcarbonyl)pyridin-3-yl]oxy}ethyl)-1,3-oxazol-2-yl]-2-fluoro-N-[(1R)-2-hydroxy-1-methylethyl]benzamide

[Chemical Formula 141]

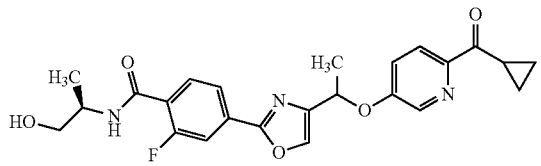

1-Hydroxybenzotriazole monohydrate (116 mg, 0.757 mmol) and N-(3-dimethylaminopropyl)-N'-ethylcarbodiimide hydrochloride (145 mg, 0.757 mmol) were added to an N,N-dimethylformamide (3.2 mL) solution of the compound obtained in Reference Example 55 (250 mg, 0.631 mmol) at room temperature, and the mixture was stirred at the same temperature for 15 minutes. Subsequently, an N,N-dimethylformamide (1.0 mL) solution of (R)-2-amino-1-propanol (142 mg, 1.89 mmol) was added at 0° C., and the mixture was further stirred at the same temperature for 10.5 minutes. Water was added to the reaction mixture, and the resulting mixture was extracted twice with ethyl acetate. The organic layer thus obtained was washed with a saturated aqueous solution of sodium hydrogen carbonate and brine, and then dried over anhydrous sodium sulfate. The solvent was distilled off under reduced pressure, and the resulting residue was purified by silica gel column chromatography (hexane:ethyl acetate=50:50→0:100, v/v) to give the title compound (235 mg, yield: 82%).

¹H-NMR (400 MHz, CDCl₃) δ ppm:
8.43 (1H, d, J=2 Hz), 8.19 (1H, t, J=8 Hz), 8.01 (1H, d, J=9 Hz), 7.92 (1H, dd, J=8, 1 Hz), 7.80 (1H, dd, J=12, 1 Hz), 7.68 (1H, s), 7.36 (1H, dd, J=9, 2 Hz), 6.96-6.88 (1H, m), 5.56 (1H, q, J=7 Hz), 4.39-4.30 (1H, m), 3.84-3.78 (1H, m), 3.71-3.65 (1H, m), 3.45-3.40 (1H, m), 2.51 (1H, t, J=5 Hz), 1.80 (3H, d, J=7 Hz), 1.32 (3H, d, J=7 Hz), 1.22-1.19 (2H, m), 1.09-1.04 (2H, m).

MS (ES) m/z: 454 [M+H]⁺.

Example 19

N-Cyclopropyl-4-[4-(1-{[6-(cyclopropylcarbonyl)pyridin-3-yl]oxy}ethyl)-1,3-oxazol-2-yl]-2-fluorobenzamide

[Chemical Formula 142]

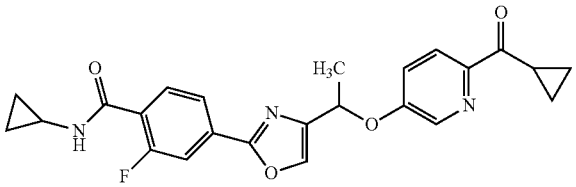

1-Hydroxybenzotriazole monohydrate (30.3 mg, 0.180 mmol) and N-(3-dimethylaminopropyl)-N'-ethylcarbodiimide hydrochloride (56.9 mg, 0.270 mmol) were added to an N,N-dimethylformamide (2 mL) solution of the compound obtained in Reference Example 55 (78.4 mg, 0.180 mmol) at room temperature, and the mixture was stirred at the same temperature for 30 minutes. Subsequently, cyclopropylamine (20.0 µL, 0.340 mmol) was added to the mixture, and the resulting mixture was further stirred at the same temperature for 30 minutes. Water, a saturated aqueous solution of sodium hydrogen carbonate, and a 10% aqueous solution of sodium chloride were added to the mixture. The resulting mixture was extracted three times with ethyl acetate, and dried over anhydrous sodium sulfate. The solvent was distilled off under reduced pressure, and the resulting residue was purified by silica gel column chromatography (hexane:ethyl acetate=2: 1→1:4, v/v) to give the title compound (69.0 mg, yield: 80%).

¹H-NMR (400 MHz, CDCl₃) δ ppm:
8.42 (1H, d, J=3 Hz), 8.21 (1H, dd, J=8, 8 Hz), 8.01 (1H, d, J=9 Hz), 7.91 (1H, dd, J=8, 2 Hz), 7.78 (1H, dd, J=13, 2 Hz), 7.67 (1H, s), 7.36 (1H, dd, J=9, 3 Hz), 6.90-6.80 (1H, m), 5.56 (1H, q, J=7 Hz), 3.47-3.40 (1H, m), 3.00-2.92 (1H, m), 1.79 (3H, d, J=6 Hz), 1.23-1.18 (2H, m), 1.10-1.04 (2H, m), 0.93-0.88 (2H, m), 0.68-0.62 (2H, m).

MS (ES) m/z: 436 [M+H]⁺.

Example 20

1-{4-[4-(1-{[6-(Cyclopropylcarbonyl)pyridin-3-yl]oxy}ethyl)-1,3-oxazol-2-yl]-2-fluorophenyl}-3-(2-hydroxyethyl)urea

[Chemical Formula 143]

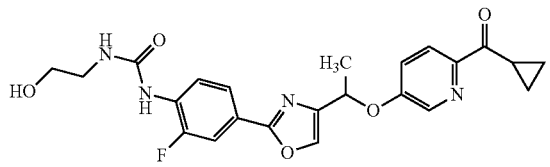

Diisopropylethylamine (25.8 µL, 0.148 mmol) and triphosgene (10.9 mg, 37.0 µmol) were added to a tetrahydrofuran (1 mL) solution of the compound obtained in Reference Example 57 (27.2 mg, 74.0 µmol) at room temperature, and the mixture was stirred at room temperature for 20 minutes. Ethanolamine (20.0 µL, 0.285 mmol) was added to the mixture at room temperature, and the resulting mixture was stirred at the same temperature for 30 minutes. Water was added to the reaction mixture, and the resulting mixture was extracted three times with ethyl acetate. The organic layer thus obtained was washed with a saturated aqueous solution of sodium hydrogen carbonate, and then dried over anhydrous sodium sulfate. The solvent was distilled off under reduced pressure, and the resulting residue was purified by silica gel column chromatography (hexane:ethyl acetate=2: 1→ethyl acetate, v/v) to give the title compound (22.7 mg, yield: 67%).

¹H-NMR (400 MHz, CDCl₃) δ ppm:
8.42 (1H, d, J=2 Hz), 8.27 (1H, dd J=9, 8 Hz), 8.00 (1H, d, J=9 Hz), 7.76 (1H, d, J=9 Hz), 7.70 (1H, dd, J=12, 2 Hz), 7.58 (1H, s), 7.36 (1H, dd, J=9, 3 Hz), 7.15-7.04 (1H, m), 5.53 (1H, q, J=6 Hz), 5.42-5.36 (1H, m), 3.85-3.76 (2H, m), 3.50-3.38 (3H, m), 2.46-2.39 (1H, m), 1.78 (3H, d, J=7 Hz), 1.23-1.17 (2H, m), 1.09-1.02 (2H, m).

MS (FAB) m/z: 455 [M+H]⁺.

By using a compound obtained in a Reference Example or a compound obtained in an Example, the compounds in the following Tables were obtained by reference to the above Examples.

TABLE 4

| Example | Compound name | Structural formula | NMR |
|---|---|---|---|
| 21 | 4-(4-{1-[4-(Cyclopropylcarbonyl)phenoxy]ethyl}-1,3-oxazol-2-yl)-2-fluoro-N-[(1R)-2-hydroxy-1-methylethyl]benzamide | | ¹H-NMR (400 MHz, CDCl₃) δ ppm: 8.19 (1H, dd, J = 8, 8 Hz), 7.99 (2H, d, J = 9 Hz), 7.92 (1H, d, J = 8 Hz), 7.80 (1H, d, J = 12 Hz), 7.64 (1H, s), 7.02 (2H, d, J = 7 Hz), 6.96-6.87 (1H, m), 5.54 (1H, q, J = 7 Hz), 4.40-4.30 (1H, m), 3.86-3.79 (1H, m), 3.71-3.66 (1H, m), 2.65-2.58 (1H, m), 2.53-2.48 (1H, m), 1.76 (3H, d, J = 6 Hz), 1.32 (3H, d, J = 7 Hz), 1.22-1.17 (2H, m), 1.02-0.97 (2H, m). MS (ES) m/z: 453 [M + H]⁺. |

TABLE 4-continued

| Example | Compound name | Structural formula | NMR |
|---|---|---|---|
| 22 | 4-(4-{1-[4-(Cyclopropyl-carbonyl)phenoxy]ethyl}-1,3-oxazol-2-yl)-2-fluoro-N-[2-hydroxy-1-(hydroxymethyl)ethyl]benzamide | | $^1$H-NMR (400 MHz, CDCl$_3$) δ ppm: 8.19 (1H, dd, J = 8, 8 Hz), 7.99 (2H, d, J = 9 Hz), 7.92 (1H, dd, J = 8, 2 Hz), 7.81 (1H, dd, J = 13, 2 Hz), 7.64 (1H, s), 7.56-7.48 (1H, m), 7.02 (2H, dd, J = 7, 2 Hz), 5.54 (1H, q, J = 6 Hz), 4.28-4.21 (1H, m), 4.05-3.90 (4H, m), 2.66-2.59 (1H, m), 2.53-2.46 (2H, m), 1.76 (3H, d, J = 6 Hz), 1.23-1.18 (2H, m), 1.02-0.97 (2H, m). MS (ES) m/z: 469 [M + H]$^+$. |
| 23 | 1-[4-(4-{1-[4-(Cyclopropyl-carbonyl)phenoxy]ethyl}-1,3-oxazol-2-yl)-2-fluorophenyl]urea | | $^1$H-NMR (400 MHz, DMSO-d$_6$) δ ppm: 8.64 (1H, d, J = 2 Hz), 8.36 (1H, dd, J = 9, 8 Hz), 8.21 (1H, s), 8.00 (2H, d, J = 9 Hz), 7.71-7.65 (2H, m), 7.15 (2H, d, J = 9 Hz), 6.36 (2H, s), 5.71 (1H, q, J = 6 Hz), 2.83 (1H, dddd, J = 6 Hz), 1.65 (3H, d, J = 7 Hz), 0.97 (4H, d, J = 6 Hz). MS (ES) m/z: 410 [M + H]$^+$. |

TABLE 5

| Example | Compound name | Structural formula | NMR |
|---|---|---|---|
| 24 | 1-[4-(4-{1-[4-(Cyclopropyl-carbonyl)phenoxy]ethyl}-1,3-oxazol-2-yl)-2-fluorophenyl]-3-(2-hydroxyethyl)urea | | $^1$H-NMR (400 MHz, CDCl$_3$) δ ppm: 8.27 (1H, dd, J = 9, 8 Hz), 7.98 (2H, d, J = 9 Hz), 7.79-7.71 (2H, m), 7.55 (1H, s), 7.02 (2H, d, J = 9 Hz), 6.98-6.89 (1H, m), 5.51 (1H, q, J = 6 Hz), 5.25-5.19 (1H, m), 3.81 (2H, dd, J = 6, 5 Hz), 3.48 (2H, dd, J = 6, 5 Hz), 2.65-2.58 (1H, m), 2.29-2.24 (1H, m), 1.75 (3H, d, J = 7 Hz), 1.23-1.18 (2H, m), 1.02-0.96 (2H, m). MS (ES) m/z: 454 [M + H]$^+$. |
| 25 | 1-{4-[4-(1-{[6-(Cyclopropyl-carbonyl)pyridin-3-yl]oxy}ethyl)-1,3-oxazol-2-yl]-2-fluorophenyl}urea | | $^1$H-NMR (400 MHz, CDCl$_3$) δ ppm: 8.42 (1H, d, J = 2 Hz), 8.28 (1H, dd, J = 8, 8 Hz), 8.00 (1H, d, J = 9 Hz), 7.78 (1H, d, J = 9 Hz), 7.73 (1H, d, J = 11 Hz), 7.59 (1H, s), 7.36 (1H, dd, J = 9, 2 Hz), 6.94 (1H, s), 5.54 (1H, q, J = 6 Hz), 4.84 (2H, s), 3.47-3.38 (1H, m), 1.78 (3H, d, J = 6 Hz), 1.24-1.18 (2H, m), 1.09-1.03 (2H, m). MS (ES) m/z: 411 [M + H]$^+$. |

Examples 26

4-{5-[(1R)-1-{[6-(Cyclopropylcarbonyl)pyridin-3-yl]oxy}ethyl]-1,2,4-oxadiazol-3-yl}-2-fluoro-N-[(1R)-2-hydroxy-1-methylethyl]benzamide

[Chemical Formula 144]

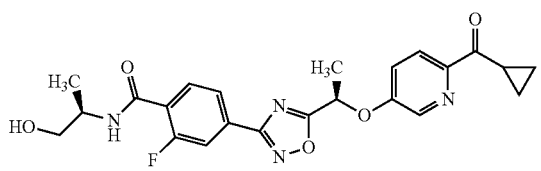

1-Hydroxybenzotriazole monohydrate (46.2 mg, 0.302 mmol) and N-(3-dimethylaminopropyl)-N'-ethylcarbodiimide hydrochloride (57.9 mg, 0.302 mmol) were added to an N,N-dimethylformamide (1.3 mL) solution of the compound obtained in Reference Example 59 (100 mg, 0.252 mmol) at room temperature, and the mixture was stirred at the same temperature for 30 minutes. Subsequently, an N,N-dimethylformamide (1.0 mL) solution of (R)-2-amino-1-propanol (56.7 mg, 0.755 mmol) was added to the mixture at 0° C., and the resulting mixture was further stirred at the same temperature for 1 hour. Water was added to the reaction mixture, and the resulting mixture was extracted twice with ethyl acetate. The organic layer thus obtained was washed with a saturated aqueous solution of sodium hydrogen carbonate and brine, and then dried over anhydrous sodium sulfate. The solvent was distilled off under reduced pressure, and the resulting residue was purified by silica gel column chromatography (hexane:ethyl acetate=50:50→0:100, v/v) to give the title compound (102 mg, yield: 89%).

$^1$H-NMR (400 MHz, CDCl$_3$) δ ppm:

8.47 (1H, d, J=3 Hz), 8.21 (1H, t, J=8 Hz), 8.03 (1H, d, J=9 Hz), 7.98 (1H, dd, J=8, 1 Hz), 7.85 (1H, dd, J=12, 1 Hz), 7.39 (1H, dd, J=9, 3 Hz), 6.97-6.85 (1H, m), 5.78 (1H, J=7 Hz), 4.40-4.29 (1H, m), 3.81 (1H, dd, J=11, 3 Hz), 3.68 (1H, dd, J=11, 6 Hz), 3.47-3.37 (1H, m), 2.49 (1H, br s), 1.95 (3H, d, J=7 Hz), 1.32 (3H, d, J=7 Hz), 1.24-1.18 (2H, m), 1.10-1.04 (2H, m);

MS (ES) m/z: 455 [M+H]$^+$.

By using a compound obtained in a Reference Example or a compound obtained in an Example, the compounds in the following Tables were obtained by reference to the above Examples.

TABLE 6

| Example | Compound name | Structural formula | NMR |
|---|---|---|---|
| 27 | 4-{5-[(1R)-1-{[6-(Cyclopropyl-carbonyl)pyridin-3-yl]oxy}ethyl]-1,2,4-oxadiazol-3-yl}-2-fluoro-N-[2-hydroxy-1-(hydroxymethyl)ethyl]benzamide | | $^1$H-NMR (400 MHz, CDCl$_3$) δ ppm: 8.47 (1H, d, J = 3 Hz), 8.20 (1H, t, J = 8 Hz), 8.03 (1H, d, J = 9 Hz), 7.98 (1H, dd, J = 8, 1 Hz), 7.85 (1H, dd, J = 12, 1 Hz), 7.56-7.46 (1H, m), 7.39 (1H, dd, J = 9, 3 Hz), 5.79 (1H, q, J = 7 Hz), 4.28-4.20 (1H, m), 4.04-3.98 (2H, m), 3.97-3.88 (2H, m), 3.46-3.38 (1H, m), 2.58 (2H, br s), 1.96 (3H, d, J = 7 Hz), 1.23-1.19 (2H, m), 1.10-1.05 (2H, m); MS (ES) m/z: 471 [M + H]$^+$. |
| 28 | N-Cyclopropyl-4-{5-[(1R)-1-{[6-(cyclopropyl-carbonyl)pyridin-3-yl]oxy}ethyl]-1,2,4-oxadiazol-3-yl}-2-fluorobenzamide | | $^1$H-NMR (400 MHz, CDCl$_3$) δ ppm: 8.46 (1H, d, J = 3 Hz), 8.23 (1H, t, J = 8 Hz), 8.03 (1H, d, J = 9 Hz), 7.97 (1H, dd, J = 8, 1 Hz), 7.82 (1H, dd, J = 12, 1 Hz), 7.39 (1H, dd, J = 9, 3 Hz), 6.89-6.81 (1H, m), 5.78 (1H, q, J = 7 Hz), 3.46-3.39 (1H, m), 3.00-2.92 (1H, m), 1.96 (3H, d, J = 7 Hz), 1.23-1.19 (2H, m), 1.10-1.04 (2H, m), 0.94-0.88 (2H, m), 0.68-0.63 (2H, m); MS (ES) m/z: 437 [M + H]$^+$. |
| 29 | 2-Fluoro-N-[(1R)-2-hydroxy-1-methylethyl]-4-(5-{1-[(6-isobutyrylpyridin-3-yl)oxy]propyl}-1,2,4-oxadiazol-3-yl)benzamide hydrochloride | | $^1$H-NMR (500 MHz, CDCl$_3$) δ ppm: 8.42 (1H, d, J = 3 Hz), 8.21 (1H, t, J = 8 Hz), 8.04 (1H, d, J = 9 Hz), 7.98 (1H, dd, J = 8, 2 Hz), 7.85 (1H, dd, J = 12, 2 Hz), 7.36 (1H, dd, J = 9, 3 Hz), 6.94-6.87 (1H, m), 5.54 (1H, dd, J = 7, 6 Hz), 4.37-4.31 (1H, m), 4.07-4.00 (1H, m), 3.81 (1H, dd, J = 11, 4 Hz), 3.68 (1H, dd, J = 11, 6 Hz), 2.39-2.24 (2H, m), 1.32 (3H, d, J = 7 Hz), 1.18 (6H, d, J = 7 Hz), 1.16 (3H, t, J = 7 Hz); MS (ES) m/z: 471 [M + H]$^+$. |

TABLE 7

| Example | Compound name | Structural formula | NMR |
|---|---|---|---|
| 30 | 4-{5-[(1R)-1-{[6-(1,1-Difluoro-3-methylbutyl)pyridin-3-yl]oxy}propyl]-1,2,4-oxadiazol-3-yl}-2-fluoro-N-(2-hydroxyethyl)benzamide | | ¹H-NMR (500 MHz, CDCl₃) δ ppm: 8.42 (1H, d, J = 3 Hz), 8.23 (1H, t, J = 8 Hz), 7.99 (1H, dt, J = 8, 1 Hz), 7.86 (1H, dd, J = 12, 1 Hz), 7.57 (1H, d, J = 9 Hz), 7.35 (1H, dd, J = 9, 3 Hz), 7.24-7.16 (1H, m), 5.48 (1H, dd, J = 7, 6 Hz), 3.88 (2H, t, J = 5 Hz), 3.69 (2H, q, J = 5 Hz), 2.37-2.12 (5H, m), 1.92-1.80 (1H, m), 1.15 (3H, t, J = 7 Hz), 0.94 (6H, d, J = 7 Hz); MS (ES) m/z: 493 [M + H]⁺. |
| 31 | 4-{5-[(1R)-1-{[6-(Cyclopropyl-carbonyl)pyridin-3-yl]oxy}propyl]-1,2,4-oxadiazol-3-yl}-2-fluoro-N-[(1R)-2-hydroxy-1-methylethyl]benzamide | | ¹H-NMR (400 MHz, CDCl₃) δ ppm: 8.46 (1H, d, J = 3 Hz), 8.21 (1H, t, J = 8 Hz), 8.02 (1H, d, J = 9 Hz), 7.97 (1H, dd, J = 8, 2 Hz), 7.84 (1H, dd, J = 12, 2 Hz), 7.37 (1H, dd, J = 9, 3 Hz), 6.92-6.89 (1H, m), 5.55 (1H, dd, J = 7, 6 Hz), 4.38-4.31 (1H, m), 3.81 (1H, dd, J = 11, 4 Hz), 3.68 (1H, dd, J = 11, 6 Hz), 3.45-3.39 (1H, m), 2.46 (1H, br s), 2.40-2.23 (2H, m), 1.32 (3H, d, J = 7 Hz), 1.21-1.20 (2H, m), 1.16 (3H, t, J = 7 Hz), 1.08-1.06 (2H, m); MS (FAB) m/z: 469 [M + H]⁺. |

Examples 32

1-{4-[5-(1-{[6-(Cyclopropylcarbonyl)pyridin-3-yl]oxy}ethyl)-1,2,4-oxadiazol-3-yl]-2-fluorophenyl}-3-(2-hydroxyethyl)urea

[Chemical Formula 145]

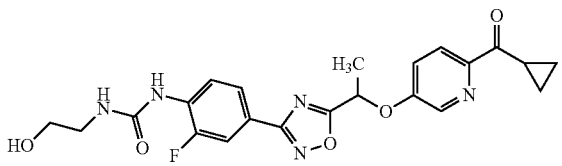

Triethylamine (75.7 μL, 0.543 mmol), and triphosgene (40.3 mg, 0.136 mmol) were added to a tetrahydrofuran (2.7 mL) solution of the compound obtained in Reference Example 76 (100 mg, 0.271 mmol) at 0° C., and the mixture was stirred at the same temperature for 15 minutes. Subsequently, a tetrahydrofuran (1.0 mL) solution of 2-aminoethanol (85.6 mg, 1.36 mmol) was added to the mixture, and then the resulting mixture was further stirred at the same temperature for 15 minutes. Water was added to the reaction mixture, and the resulting mixture was extracted twice with ethyl acetate. The organic layer thus obtained was washed with brine, and then dried over anhydrous sodium sulfate. The solvent was distilled off under reduced pressure, and the resulting residue was washed with hexane-dichloromethane (2:1, v/v) to give the title compound (105 mg, yield: 85%).

¹H-NMR (400 MHz, DMSO-d₆) δ ppm:
8.76 (1H, d, J=3 Hz), 8.57 (1H, d, J=3 Hz), 8.39 (1H, dd, J=9, 8 Hz), 7.97 (1H, d, J=9 Hz), 7.75-7.68 (3H, m), 6.93 (1H, t, J=6 Hz), 6.28 (1H, q, J=7 Hz), 4.79 (1H, t, J=5 Hz), 3.46 (2H, q, J=5 Hz), 3.43-3.38 (1H, m), 3.18 (2H, td, J=6, 5 Hz), 1.84 (3H, d, J=7 Hz), 1.09-0.98 (4H, m).

MS (ES) m/z: 456 [M+H]⁺.

By using a compound obtained in a Reference Example or a compound obtained in an Example, the compounds in the following Tables were obtained by reference to the above Examples.

TABLE 8

| Example | Compound name | Structural formula | NMR |
|---|---|---|---|
| 33 | 1-[4-(5-{(1R)-1-[4-(Cyclopropyl-carbonyl)phen-oxy]propyl}-1,2,4-oxadiazol-3-yl)-2-fluorophenyl] urea | | ¹H-NMR (500 MHz, CDCl₃) δ ppm: 8.30 (1H, dd, J = 9, 8 Hz), 7.98 (2H, d, J = 9 Hz), 7.87-7.83 (1H, m), 7.78 (1H, dd, J = 12, 2 Hz), 7.03 (2H, d, J = 9 Hz), 6.82 (1H, d, J = 4 Hz), 5.49 (1H, dd, J = 7, 6 Hz), 4.75 (2H, s), 2.63-2.56 (1H, m), 2.35-2.17 (2H, m), 1.21-1.17 (2H, m), 1.13 (3H, t, J = 7 Hz), 1.02-0.96 (2H, m); MS (ES) m/z: 425 [M + H]⁺. |
| 34 | 1-[4-(5-{(1R)-1-[4-(Cyclopropyl-carbonyl)phen-oxy]propyl}-1,2,4-oxadiazol-3-yl)-2-fluorophenyl]-3-[2-hydroxy-1-(hydroxymethyl) ethyl]urea | | ¹H-NMR (500 MHz, CDCl₃) δ ppm: 8.16 (1H, t, J = 8 Hz), 7.94 (2H, d, J = 9 Hz), 7.80 (1H, s), 7.68 (1H, d, J = 8 Hz), 7.60 (1H, d, J = 12 Hz), 7.00 (2H, d, J = 9 Hz), 6.38-6.30 (1H, m), 5.45 (1H, dd, J = 7, 6 Hz), 3.93-3.70 (7H, m), 2.60-2.52 (1H, m), 2.28-2.13 (2H, m), 1.19-1.13 (2H, m), 1.09 (3H, t, J = 7.3 Hz), 1.00-0.94 (2H, m); MS (ES) m/z: 499 [M + H]⁺. |
| 35 | 1-{4-[5-(1-{[6-(Cyclopropyl-carbonyl)pyri-din-3-yl]oxy}ethyl)-1,2,4-oxadiazol-3-yl]-2-fluorophenyl} urea | | ¹H-NMR (400 MHz, DMSO-d₆) δ ppm: 8.70 (1H, d, J = 3 Hz), 8.57 (1H, d, J = 3 Hz), 8.40 (1H, t, J = 9 Hz), 7.97 (1H, d, J = 9 Hz), 7.75-7.69 (3H, m), 6.38 (2H, s), 6.28 (1H, q, J = 7 Hz), 3.43-3.38 (1H, m), 1.84 (3H, d, J = 7 Hz), 1.09-0.99 (4H, m). MS (ES) m/z: 412 [M + H]⁺. |

TABLE 9

| Example | Compound name | Structural formula | NMR |
|---|---|---|---|
| 36 | 1-[2-Fluoro-4-(5-{1-[4-(5-isopropyl-1,2,4-oxadiazol-3-yl)phenoxy]propyl}-1,2,4-oxazol-3-yl)phenyl]-3-(2-hydroxyethyl)urea | | $^1$H-NMR (400 MHz, CDCl$_3$) δ ppm: 8.28 (1H, dd, J = 8, 8 Hz), 8.00 (2H, d, J = 8 Hz), 7.83 (1H, d, J = 9 Hz), 7.76 (1H, d, J = 12 Hz), 7.06 (2H, d, J = 7 Hz), 5.47 (1H, t, J = 6 Hz), 5.43-5.34 (1H, m), 3.80 (2H, dt, J = 5, 5 Hz), 3.47 (2H, dt, J = 5, 5 Hz), 3.25 (1H, dq, J = 7, 7 Hz), 2.47-2.37 (1H, m), 2.34-2.16 (2H, m), 1.43 (6H, d, J = 7 Hz), 1.13 (3H, t, J = 7 Hz). MS (ES) m/z: 511 [M + H]$^+$. |
| 37 | 1-(2-Fluoroethyl)-3-[2-fluoro-4-(5-{1-[4-(5-isopropyl-1,2,4-oxadiazol-3-yl)phenoxy]propyl}-1,2,4-oxadiazol-3-yl)phenyl]urea | | $^1$H-NMR (400 MHz, CDCl$_3$) δ ppm: 8.29 (1H, dd, J = 8, 8 Hz), 7.99 (2H, d, J = 9 Hz), 7.84 (1H, d, J = 9 Hz), 7.77 (1H, dd, J = 12, 1 Hz), 7.06 (2H, d, J = 9 Hz), 6.78 (1H, bs), 5.47 (1H, t, J = 6 Hz), 5.23 (1H, bs), 4.61 (1H, dd, J = 5, 5 Hz), 4.51 (1H, dd, J = 5, 4 Hz), 3.65 (2H, dt, J = 5, 5 Hz), 3.59 (1H, dt, J = 5, 5 Hz), 3.25 (1, dq, J = 7, 7 Hz), 2.31-2.17 (2H, m), 1.43 (6H, d, J = 7 Hz), 1.13 (3H, t, J = 7 Hz). MS (FAB) m/z: 513 [M + H]$^+$. |

TABLE 9-continued

| Example | Compound name | Structural formula | NMR |
|---|---|---|---|
| 38 | 1-[2-Fluoro-4-(5-{1-[4-(5-isopropyl-1,2,4-oxadiazol-3-yl)phenoxy]propyl}-1,2,4-oxadiazol-3-yl)phenyl]-3-[(2S)-2-hydroxypropyl]urea | | $^1$H-NMR (400 MHz, CDCl$_3$) δ ppm: 8.29 (1H, dd, J = 8, 8 Hz), 8.00 (2H, d, J = 9 Hz), 7.84 (1H, d, J = 9 Hz), 7.77 (1H, d, J = 12 Hz), 7.06 (2H, d, J = 9 Hz), 5.47 (1H, t, J = 7 Hz), 5.30 (1H, bs), 4.06-3.96 (1H, m), 3.53-3.44 (1H, m), 3.31-3.10 (2H, m), 2.34-2.16 (3H, m), 1.43 (6H, d, J = 7 Hz), 1.25 (3H, d, J = 6 Hz), 1.13 (3H, t, J = 7 Hz). MS (FAB) m/z: 525 [M + H]$^+$. |

TABLE 10

| Example | Compound name | Structural formula | NMR |
|---|---|---|---|
| 39 | 2-({[2-Fluoro-4-(5-{1-[4-(5-isopropyl-1,2,4-oxadiazol-3-yl)phenoxy]propyl}-1,2,4-oxadiazol-3-yl)phenyl]carbamoyl}amino)ethyl methyl carbonate | | $^1$H-NMR (500 MHz, CDCl$_3$) δ ppm: 8.29 (1H, dd, J = 8, 8 Hz), 8.00 (2H, d, J = 9 Hz), 7.84 (1H, d, J = 9 Hz), 7.77 (1H, dd, J = 12, 2 Hz), 7.06 (2H, d, J = 9 Hz), 6.74-6.68 (1H, m), 5.47 (1H, t, J = 7 Hz), 5.21-5.17 (1H, m), 4.29 (2H, t, J = 5 Hz), 3.82 (3H, s), 3.61 (2H, dt, J = 5, 5 Hz), 3.25 (1H, dq, J = 7, 7 Hz), 2.33-2.17 (2H, m), 1.43 (6H, d, J = 7 Hz), 1.13 (3H, t, J = 7 Hz). MS (FAB) m/z: 569 [M + H]$^+$. |

TABLE 10-continued

| Example | Compound name | Structural formula | NMR |
|---|---|---|---|
| 40 | 2-({[2-Fluoro-4-(5-{1-[4-(5-isopropyl-1,2,4-oxadiazol-3-yl)phenoxy]propyl}-1,2,4-oxadiazol-3-yl)phenyl]carbamoyl}amino)ethyl ethyl carbamate | | $^1$H-NMR (400 MHz, CDCl$_3$) δ ppm: 8.30 (1H, dd, J = 9, 8 Hz), 8.00 (2H, d, J = 9 Hz), 7.83 (1H, d, J = 8 Hz), 7.76 (1H, d, J = 12 Hz), 7.06 (2H, d, J = 9 Hz), 6.80-6.74 (1H, m), 5.47 (1H, t, J = 6 Hz), 5.43-5.37 (1H, m), 4.78-4.70 (1H, m), 4.27-4.18 (2H, m), 3.59-3.51 (2H, m), 3.28-3.16 (3H, m), 2.32-2.15 (2H, m), 1.43 (6H, d, J = 7 Hz), 1.16-1.08 (6H, m). MS (FAB) m/z: 582 [M + H]$^+$. |

TABLE 10-continued

| Example | Compound name | Structural formula | NMR |
|---|---|---|---|
| 41 | 1-[2-Fluoro-4-(5-{(1R)-1-[4-(5-isopropyl-1,2,4-oxadiazol-3-yl)phenoxy]propyl}-1,2,4-oxadiazol-3-yl)phenyl]-3-methylurea | | $^1$H-NMR (400 MHz, CDCl$_3$) δ ppm: 8.31 (1H, dd, J = 9, 8 Hz), 8.00 (2H, d, J = 9 Hz), 7.84 (1H, d, J = 8 Hz), 7.76 (1H, d, J = 12, 2 Hz), 7.06 (2H, d, J = 9 Hz), 6.66-6.59 (1H, m), 5.47 (1H, t, J = 7 Hz), 4.80-4.68 (1H, m), 3.25 (1H, dq, J = 7, 7 Hz), 2.90 (3H, s), 2.32-2.18 (2H, m), 1.43 (6H, d, J = 7 Hz), 1.13 (3H, t, J = 7 Hz). MS (ES) m/z: 481 [M + H]$^+$. |

Example 42

4-[3-(1-{[6-(Cyclopropylcarbonyl)pyridin-3-yl]oxy}ethyl)-1,2,4-oxadiazol-5-yl]-2-fluoro-N-[2-hydroxy-1-(hydroxymethyl)ethyl]benzamide

[Chemical Formula 146]

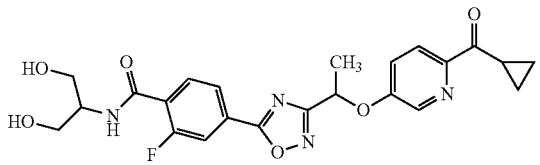

1-Hydroxybenzotriazole monohydrate (32.4 mg, 0.211 mmol) and N-(3-dimethylaminopropyl)-N'-ethylcarbodiimide hydrochloride (40.5 mg, 0.211 mmol) were added to an N,N-dimethylformamide (1.0 mL) solution of the compound obtained in Reference Example 94 (70.0 mg, 0.176 mmol) at room temperature, and the mixture was stirred at the same temperature for 30 minutes. Subsequently, an N,N-dimethylformamide (1.0 mL) solution of 2-amino-1,3-propanediol (48.2 mg, 0.528 mmol) was added to the mixture at 0° C., and the resulting mixture was further stirred at the same temperature for 1.5 hours. Water was added to the reaction mixture, and the resulting mixture was extracted twice with ethyl acetate. The organic layer thus obtained was washed with a saturated aqueous solution of sodium hydrogen carbonate and brine, and then dried over anhydrous sodium sulfate. The solvent was distilled off under reduced pressure, and the resulting residue was purified by silica gel column chromatography (dichloromethane:methanol=100:0→90:10, v/v) to give the title compound (73.7 mg, yield: 89%).

$^1$H-NMR (400 MHz, CDCl$_3$) δ ppm:
8.47 (1H, d, J=3 Hz), 8.26 (1H, dd, J=9, 8 Hz), 8.04 (1H, dd, J=8, 1 Hz), 8.01 (1H, d, J=9 Hz), 7.93 (1H, dd, J=12, 1 Hz), 7.57-7.46 (1H, m), 7.43 (1H, dd, J=9, 3 Hz), 5.74 (1H, q, J=7 Hz), 4.28-4.22 (1H, m), 4.04-3.99 (2H, m), 3.97-3.91 (2H, m), 3.45-3.39 (1H, m), 2.46 (2H, dd, J=7, 5 Hz), 1.91 (3H, d, J=7 Hz), 1.22-1.17 (2H, m), 1.09-1.03 (2H, m);
MS (ES) m/z: 471 [M+H]$^+$.

Example 43

1-{4-[3-(1-{[6-(Cyclopropylcarbonyl)pyridin-3-yl]oxy}ethyl)-1,2,4-oxadiazol-5-yl]-2-fluorophenyl}-3-(2-hydroxyethyl)urea

[Chemical Formula 147]

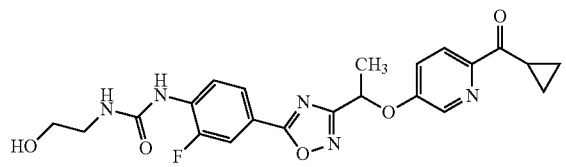

Triethylamine (35.0 μL, 0.251 mmol), and triphosgene (18.6 mg, 0.0627 mmol) were added to a tetrahydrofuran (1.0 mL) solution of the compound obtained in Reference Example 96 (46.2 mg, 0.125 mmol) at 0° C., and the mixture was stirred at the same temperature for 15 minutes. Subsequently, a tetrahydrofuran (1.0 mL) solution of 2-aminoethanol (23.7 mg, 0.376 mmol) was added to the mixture, and then the resulting mixture was further stirred at the same temperature for 15 minutes. Water was added to the reaction mixture, and the resulting mixture was extracted twice with ethyl acetate. The organic layer thus obtained was washed with brine, and then dried over anhydrous sodium sulfate. The solvent was distilled off under reduced pressure, and the resulting residue was washed with a hexane-dichloromethane (2:1, v/v) to give the title compound (49.4 mg, yield: 87%).

$^1$H-NMR (400 MHz, DMSO-$d_6$) δ ppm:

8.92 (1H, d, J=3 Hz), 8.52 (1H, d, J=3 Hz), 8.48 (1H, t, J=8 Hz), 7.94 (1H, d, J=9 Hz), 7.91-7.85 (2H, m), 7.67 (1H, dd, J=9, 3 Hz), 7.01 (1H, t, J=5 Hz), 6.08 (1H, q, J=7 Hz), 4.80 (1H, t, J=5 Hz), 3.6 (2H, td, J=6, 5 Hz), 3.42-3.37 (1H, m), 3.19 (2H, td, J=6, 5 Hz), 1.77 (3H, d, J=7 Hz), 1.07-0.98 (4H, m);

MS (ES) m/z: 456 [M+H]$^+$.

By using a compound obtained in a Reference Example or a compound obtained in an Example, the compounds in the following Tables were obtained by reference to the above Examples.

TABLE 11

| Example | Compound name | Structural formula | NMR |
|---|---|---|---|
| 44 | 4-(3-{1-[4-(Cyclopropyl-carbonyl)phenoxy]ethyl}-1,2,4-oxadiazol-5-yl)-2-fluoro-N-[(1R)-2-hydroxy-1-methylethyl]benz-amide | | $^1$H-NMR (400 MHz, CDCl$_3$) δ ppm: 8.29-8.23 (1H, m), 8.04 (1H, d, J = 8 Hz), 7.99 (2H, d, J = 9 Hz), 7.92 (1H, d, J = 12 Hz), 7.09 (2H, d, J = 9 Hz), 6.97-6.88 (1H, m), 5.75-5.68 (1H, m), 4.35 (1H, bs), 3.87-3.78 (1H, m), 3.72-3.66 (1H, m), 2.65-2.56 (1H, m), 2.38-2.32 (1H, m), 1.87 (3H, d, J = 6 Hz), 1.33 (3H, d, J = 7 Hz), 1.22-1.18 (2H, m), 1.03-0.96 (2H, m). MS (ES) m/z: 454 [M + H]$^+$. |
| 45 | 4-(3-{1-[4-(Cyclopropyl-carbonyl)phenoxy]ethyl}-1,2,4-oxadiazol-5-yl)-2-fluoro-N-[2-hydroxy-1-(hydroxymethyl)ethyl]benzamide | | $^1$H-NMR (400 MHz, CDCl$_3$) δ ppm: 8.25 (1H, d, J = 8 Hz), 8.04 (1H, d, J = 8 Hz), 7.99 (2H, d, J = 9 Hz), 7.93 (1H, d, J = 12 Hz), 7.57-7.49 (1H, s), 7.09 (2H, d, J = 9 Hz), 5.78-5.69 (1H, m), 4.25 (1H, bs), 4.06-3.90 (4H, m), 2.65-2.58 (1H, m), 2.50-2.43 (2H, m), 1.87 (3H, d, J = 6 Hz), 1.123-1.18 (2H, m), 1.04-0.96 (2H, m). MS (ES) m/z: 470 [M + H]$^+$. |

TABLE 11-continued

| Example | Compound name | Structural formula | NMR |
|---|---|---|---|
| 46 | 1-[4-(3-{1-[4-(Cyclopropyl-carbonyl)phenoxy]ethyl}-1,2,4-oxadiazol-5-yl)-2-fluorophenyl]-3-(2-hydroxyethyl)urea | | ¹H-NMR (400 MHz, CDCl₃) δ ppm: 8.39 (1H, dd, J = 9, 8 Hz), 7.98 (2H, d, J = 9 Hz), 7.88 (1H, d, J = 9 Hz), 7.80 (1H, d, J = 12 Hz), 7.08 (2H, d, J = 9 Hz), 5.68 (1H, q, J = 7 Hz), 5.60-5.48 (1H, m), 3.85-3.78 (2H, m), 3.51-3.45 (2H, m), 2.65-2.58 (1H, m), 2.48-2.32 (1H, m), 1.84 (3H, d, J = 6 Hz), 1.24-1.17 (2H, m), 1.04-0.97 (2H, m). MS (ES) m/z: 455 [M + H]⁺. |

TABLE 12

| Example | Compound name | Structural formula | NMR |
|---|---|---|---|
| 47 | 1-[4-(3-{1-[4-(Cyclopropyl-carbonyl)phenoxy]ethyl}-1,2,4-oxadiazol-5-yl)-2-fluorophenyl]urea | | ¹H-NMR (400 MHz, CDCl₃) δ ppm: 8.41 (1H, dd, J = 8, 7 Hz), 7.97 (2H, d, J = 9 Hz), 7.90 (1H, d, J = 9 Hz), 7.82 (1H, d, J = 11 Hz), 7.16-7.05 (3H, m), 5.68 (1H, q, J = 7 Hz), 4.90 (2H, s), 2.65-2.58 (1H, m), 1.84 (3H, d, J = 7 Hz), 1.22-1.17 (2H, m), 1.02-0.96 (2H, m). MS (ES) m/z: 411 [M + H]⁺. |
| 48 | 1-[4-(3-{1-[4-(Cyclopropyl-carbonyl)phenoxy]propyl}-1,2,4-oxadiazol-5-yl)-2-fluorophenyl]-3-(2-hydroxyethyl)urea | | ¹H-NMR (400 MHz, CDCl₃) δ ppm: 8.39 (1H, dd, J = 8, 8 Hz), 7.97 (2H, d, J = 9 Hz), 7.88 (1H, d, J = 9 Hz), 7.80 (1H, d, J = 11 Hz), 7.08 (2H, d, J = 9 Hz), 5.59-5.49 (1H, m), 5.41 (1H, t, J = 7 Hz), 3.85-3.77 (2H, m), 3.47 (2H, dt, J = 5, 5 Hz), 2.62-2.56 (1H, m), 2.44-2.12 (3H, m), 1.22-1.13 (2H, m), 1.10 (3H, t, J = 7 Hz), 1.04-0.96 (2H, m). MS (ES) m/z: 469 [M + H]⁺. |

TABLE 12-continued

| Example | Compound name | Structural formula | NMR |
|---|---|---|---|
| 49 | 1-[4-(3-{1-[4-(Cyclopropyl-carbonyl)phenoxy]propyl}-1,2,4-oxadiazol-5-yl)-2-fluorophenyl]urea | | $^1$H-NMR (400 MHz, CDCl$_3$) δ ppm: 8.42 (1H, dd, J = 8, 8 Hz), 7.97 (2H, d, J = 9 Hz), 7.90 (1H, d, J = 8 Hz), 7.81 (1H, dd, J = 11, 2 Hz), 7.20-7.17 (1H, m), 7.08 (2H, d, J = 9 Hz), 5.41 (1H, t, J = 7 Hz), 4.94 (2H, s), 2.64-2.56 (1H, m), 2.32-2.13 (2H, m), 1.22-1.15 (2H, m), 1.09 (3H, t, J = 7 Hz), 1.04-0.96 (2H, m). MS (ES) m/z: 425 [M + H]$^+$. |

TABLE 13

| Example | Compound name | Structural formula | NMR |
|---|---|---|---|
| 50 | 4-[3-(1-{[6-(Cyclopropylcarbonyl)pyridin-3-yl]oxy}ethyl)-1,2,4-oxadiazol-5-yl]-2-fluoro-N-[(1R)-2-hydroxy-1-methylethyl]benzamide | | $^1$H-NMR (400 MHz, CDCl$_3$) δ ppm: 8.47 (1H, d, J = 3 Hz), 8.26 (1H, t, J = 8 Hz), 8.03 (1H, dd, J = 8, 1 Hz), 8.01 (1H, d, J = 9 Hz), 7.91 (1H, dd, J = 12, 1 Hz), 7.42 (1H, dd, J = 9, 3 Hz), 6.97-6.85 (1H, m), 5.74 (1H, q, J = 6 Hz), 4.39-4.29 (1H, m), 3.85-3.77 (1H, m), 3.73-3.64 (1H, m), 3.46-3.38 (1H, m), 2.34 (1H, t, J = 6 Hz), 1.90 (3H, d, J = 6 Hz), 1.33 (3H, d, J = 7 Hz), 1.22-1.17 (2H, m), 1.09-1.03 (2H, m); MS (ES) m/z: 455 [M + H]$^+$. |

TABLE 13-continued

| Example | Compound name | Structural formula | NMR |
|---|---|---|---|
| 51 | N-Cyclopropyl-4-[3-(1-{[6-(cyclopropylcarbonyl)pyridin-3-yl]oxy}ethyl)-1,2,4-oxadiazol-5-yl]-2-fluorobenzamide | | $^1$H-NMR (400 MHz, CDCl$_3$) δ ppm: 8.47 (1H, d, J = 3 Hz), 8.28 (1H, t, J = 8 Hz), 8.03 (1H, d, J = 8, 2 Hz), 8.01 (1H, d, J = 9 Hz), 7.89 (1H, dd, J = 12, 2 Hz), 7.42 (1H, dd, J = 9, 3 Hz), 6.87-6.80 (1H, m), 5.74 (1H, q, J = 7 Hz), 3.45-3.38 (1H, m), 2.99-2.93 (1H, m), 1.90 (3H, d, J = 7 Hz), 1.22-1.17 (2H, m), 1.08-1.03 (2H, m), 0.94-0.89 (2H, m), 0.69-0.63 (2H, m). MS (ES) m/z: 437 [M + H]$^+$. |
| 52 | 1-{4-[3-(1-{[6-(Cyclopropylcarbonyl)pyridin-3-yl]oxy}ethyl)-1,2,4-oxadiazol-5-yl]-2-fluorophenyl}urea | | $^1$H-NMR (400 MHz, DMSO-d$_6$) δ ppm: 8.85 (1H, d, J = 3 Hz), 8.52 (1H, d, J = 3 Hz), 8.48 (1H, dd, J = 9, 8 Hz), 7.94 (1H, d, J = 9 Hz), 7.90-7.85 (2H, m), 7.68 (1H, dd, J = 9, 3 Hz), 6.46 (2H, s), 6.09 (1H, q, J = 7 Hz), 3.42-3.37 (1H, m), 1.77 (3H, d, J = 7 Hz), 1.07-0.98 (4H, m); MS (ES) m/z: 412 [M + H]$^+$. |

TABLE 14

| Example | Compound name | Structural formula | NMR |
|---|---|---|---|
| 53 | 4-(3-{(1R)-1-[4-(Cyclopropyl-carbonyl)phenoxy]propyl}-1,2,4-oxadiazol-5-yl)-2-fluoro-N-[(1R)-2-hydroxy-1-methylethyl]benzamide | | $^1$H-NMR (500 MHz, CDCl$_3$) δ ppm: 8.25 (1H, dd, J = 11, 8 Hz), 8.02 (1H, d, J = 8 Hz), 7.98 (2H, d, J = 9 Hz), 7.91 (1H, d, J = 11 Hz), 7.08 (2H, d, J = 9 Hz), 6.96-6.88 (1H, m), 5.46 (1H, t, J = 7 Hz), 4.34 (1H, bs), 3.84-3.79 (1H, m), 3.71-3.66 (1H, m), 2.63-2.56 (1H, m), 2.43-2.22 (3H, m), 1.32 (3H, d, J = 7 Hz), 1.19-1.15 (2H, m), 1.11 (3H, t, J = 7 Hz), 0.98-0.95 (2H, m). MS (ES) m/z: 468 [M + H]$^+$. |
| 54 | 4-(3-{(1R)-1-[4-(Cyclopropyl-carbonyl)phenoxy]propyl}-1,2,4-oxadiazol-5-yl)-2-fluoro-N-[2-hydroxy-1-(hydroxymethyl)ethyl]benzamide | | $^1$H-NMR (400 MHz, CDCl$_3$) δ ppm: 8.25 (1H, dd, J = 8, 8 Hz), 8.04 (1H, d, J = 8 Hz), 7.98 (2H, d, J = 9 Hz), 7.93 (1H, d, J = 11 Hz), 7.57-7.48 (1H, m), 7.08 (2H, d, J = 9 Hz), 5.46 (1H, t, J = 7 Hz), 4.25 (1H, bs), 4.05-3.90 (4H, m), 2.64-2.56 (1H, m), 2.51-2.45 (2H, m), 2.34-2.12 (2H, m), 1.20-1.17 (2H, m), 1.11 (3H, t, J = 7 Hz), 1.02-0.97 (2H, m). MS (ES) m/z: 484 [M + H]$^+$. |
| 55 | 2-Fluoro-N-[2-hydroxy-1-(hydroxymethyl)ethyl]-4-{3-[(1R)-1-{4-[3-(trifluoromethyl)-1,2,4-oxadiazol-5-yl]phenoxy}propyl]-1,2,4-oxadiazol-5-yl}benzamide | | $^1$H-NMR (400 MHz, CDCl$_3$) δ ppm: 8.25 (1H, dd, J = 8, 8 Hz), 8.11 (2H, d, J = 9 Hz), 8.04 (1H, d, J = 9 Hz), 7.93 (1H, d, J = 12 Hz), 7.56-7.47 (1H, m), 7.18 (2H, d, J = 9 Hz), 5.48 (1H, t, J = 7 Hz), 4.28-4.23 (1H, m), 4.04-3.90 (4H, m), 2.40-2.17 (4H, m), 1.12 (3H, t, J = 7 Hz). MS (ES) m/z: 552 [M + H]$^+$. |

Formulation Example 5 g of each of the compounds obtained in the Examples, 90 g of lactose, 34 g of corn starch, 20 g of crystalline cellulose, and 1 g of magnesium stearate were mixed with a blender, and then the mixture was tableted with a tableting machine. Thereby, tablets were obtained.

Test Example 1

Mouse oGTT (Oral Glucose Tolerance Test)

Each compound was suspended in a 0.5 w/v % methyl cellulose solution by grinding in an agate mortar at a concentration of 1 mg/mL. Male C57/BL6J mice (Charles River Laboratories Japan, Inc.) were purchased at 6 to 8 weeks of age, and then used at 9 to 13 weeks of age. The mice were fasted between 17:00 and 18:00 one day before the test day, and the test was started after 16 to 17 hours of the fasting. Five mice were used for each group. After collecting blood from the tail vein, a suspension of the compound was administered orally at a dosage of 10 mg/kg. The 0.5 w/v % methyl cellulose solution was administered to a negative control group. Blood was collected from the tail vein 25 minutes after the administration of the compound, and then a 30 w/v % glucose solution was administered orally at a volume of 10 mL/kg 30 minutes after the compound administration. Blood was collected from the tail vein 15, 30, 60 and 120 minutes after the glucose administration. Each of the blood samples was centrifuged to obtain the plasma, and the plasma glucose level (mg/dL) was measured with a glucose analyzer (Glucoloader-GXT, A&T Corp.). The plasma glucose AUC (mg/dL·min) in each mouse was calculated using the plasma glucose levels at 5 minutes before and 15, 30, 60 and 120 minutes after the glucose administration. The arithmetic mean of the AUC was calculated for each group and the percentage decrease in plasma glucose AUC (%) compared with the negative control group was calculated as an index of the efficacy.

As a result, all of the obtained compounds showed a 4% or more percentage decrease in plasma glucose AUC.

Test Example 2

Rat oGTT and Measurement of Plasma Compound Concentration

Each compound is suspended in a vehicle (0.5 w/v % methyl cellulose or 20 w/v % cyclodextrin solution) at a concentration of 1 to 10 mg/mL to prepare a suspension. As necessary, the prepared suspension is diluted with the above-described vehicle in a stepwise fashion, and multiple doses of the suspension are prepared. Male Zucker fatty rats (Charles River Laboratories Japan, Inc.) or Zucker diabetic fatty (ZDF) rats (Charles River Laboratories Japan, Inc.) can be used at 10 to 18 weeks of age. Two days before the oGTT, plasma glucose, body weight, and plasma insulin concentrations are measured, and rats are equally allocated to each group (n=5 to 8) based on these parameters. The rats are fasted from around 15:00 one day before the oGTT day. On the oGTT day, the suspension prepared by the method described above is administered orally to the rats at a volume of 1 to 5 mL/kg, and 30 minutes after the dosing, a 25 to 50 w/v % glucose solution is administered orally at a volume of 4 to 5 mL/kg. Blood is collected from the tail vein before the administration of the compound, 5 minutes before the administration of glucose, and 30, 60, 120, and 180 minutes after the administration of glucose. The obtained blood samples are centrifuged to separate the plasma, and the plasma glucose level is measured with a glucose analyzer (Glucoloader-GXT, A&T Corp.). The plasma glucose AUC in each rat is calculated using the plasma glucose levels before and after the glucose administration. The arithmetic mean of the AUC is calculated in each group and the percentage decrease in the AUC (%) compared with the vehicle-administered group is calculated as an index of the efficacy.

The plasma samples obtained by the method described above are used for measurement of the plasma concentration of the test compound. In order to quantify the plasma concentration of the test compound, blood is additionally collected 4 to 8 hours and 24 hours after the administration of the compound. The plasma is subjected to protein removal, and applied to a liquid chromatography/mass analyzer to quantify the plasma concentration of the test compound.

Test Example 3

Assessment for the Protective Effect on Pancreatic β Cells

The protective effect of the test compound on pancreatic β cells can be confirmed with reference to the method described in Junko Ogawa, et al., Life Sciences, Vol. 65, No. 12, pp. 1287-1296 (1999).

Industrial Applicability

The compounds of the present invention or pharmaceutically acceptable salts thereof are capable of treating and/or preventing type 1 diabetes, type 2 diabetes, gestational diabetes, hyperglycemia due to other factors, impaired glucose tolerance, diabetes-associated diseases, diabetic complications and the like, and are therefore useful as an active ingredient of a pharmaceutical composition for protecting β cells or the pancreas.

The invention claimed is:

1. A compound of formula (VII):

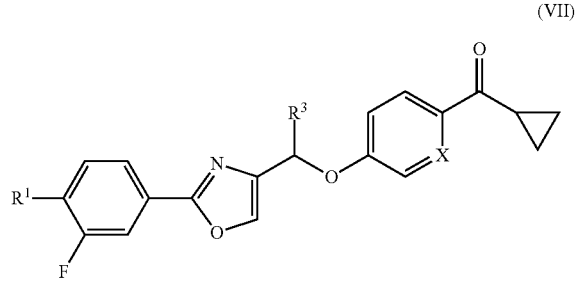

or a pharmaceutically acceptable salt thereof, wherein
X is CH or N
$R^1$ is —C(=O)—NH—$R^5$ or —NH—C(=O)—NH—$R^5$,
$R^3$ is —CH$_3$,
and
$R^5$ is —H, or is a C1-C6 alkyl group or a C3-C6 cycloalkyl group, each of which may be independently substituted with 1 to 3 —OH.

2. A compound selected from the group consisting of:
4-[4-(1-{[6-(cyclopropylcarbonyl)pyridin-3-yl]oxy}ethyl)-1,3-oxazol-2-yl]-2-fluoro-N-[(1R)-2-hydroxy-1-methylethyl]benzamide;
N-cyclopropyl-4-[4-(1-{[6-(cyclopropylcarbonyl)pyridin-3-yl]oxy}ethyl)-1,3-oxazol-2-yl]-2-fluorobenzamide;

1-{4-[4-(1-{[6-(cyclopropylcarbonyl)pyridin-3-yl]oxy}ethyl)-1,3-oxazol-2-yl]-2-fluorophenyl}-3-(2-hydroxyethyl)urea;

4-(4-{1-[4-(cyclopropylcarbonyl)phenoxy]ethyl}-1,3-oxazol-2-yl)-2-fluoro-N-[(1R)-2-hydroxy-1-methylethyl]benzamide;

4-(4-{1-[4-(cyclopropylcarbonyl)phenoxy]ethyl}-1,3-1,3-oxazol-2-yl)-2-fluoro-N-[2-hydroxy-1-(hydroxymethyl)ethyl]benzamide; and 1-[4-(4-{1-[4-(cyclopropylcarbonyl)phenoxy]ethyl}-1,3-oxazol-2-yl)-2-fluorophenyl]urea;

or a pharmaceutically acceptable salt thereof.

3. A pharmaceutical composition comprising the compound of claim 1, or a pharmaceutically acceptable salt thereof, and a pharmaceutically acceptable additive.

4. A method of treating type 1 diabetes or type 2 diabetes comprising administering to a mammal the compound of claim 1 or a pharmaceutically acceptable salt thereof.

5. The method of claim 4, wherein the mammal is a human.

6. A method of treating type 1 diabetes or type 2 diabetes comprising administering to a mammal the compound of claim 2 or a pharmaceutically acceptable salt thereof.

7. The method of claim 6, wherein the mammal is a human.

8. A pharmaceutical composition comprising the compound of claim 2, or a pharmaceutically acceptable salt thereof, and a pharmaceutically acceptable additive.

\* \* \* \* \*

UNITED STATES PATENT AND TRADEMARK OFFICE
CERTIFICATE OF CORRECTION

PATENT NO. : 9,233,958 B2
APPLICATION NO. : 14/372832
DATED : January 12, 2016
INVENTOR(S) : Yamanoi et al.

Page 1 of 1

It is certified that error appears in the above-identified patent and that said Letters Patent is hereby corrected as shown below:

In the Claims

In claim 2, at column 119 lines 7-9, delete "4-(4-{1-[4-(cyclopropylcarbonyl)phenoxy]ethyl}-1,3-1,3-oxazol-2-yl)-2-fluoro-N-[2-hydroxy-1-(hydroxymethyl)ethyl]benzamide" and insert therefor -- "4-(4-{1-[4-(cyclopropylcarbonyl)phenoxy]ethyl}-1,3-oxazol-2-yl)-2-fluoro-N-[2-hydroxy-1-(hydroxymethyl)ethyl]benzamide" --.

Signed and Sealed this
Twelfth Day of July, 2016

Michelle K. Lee
*Director of the United States Patent and Trademark Office*